US008703482B2

(12) United States Patent
Oshimura et al.

(10) Patent No.: US 8,703,482 B2
(45) Date of Patent: Apr. 22, 2014

(54) HUMAN ARTIFICIAL CHROMOSOME (HAC) VECTOR

(75) Inventors: Mitsuo Oshimura, Tottori (JP);
Motonobu Katoh, Tottori (JP); Kazuma Tomizuka, Gunma (JP); Yoshimi Kuroiwa, Gunma (JP); Minoru Kakeda, Gunma (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 176 days.

(21) Appl. No.: 12/900,165

(22) Filed: Oct. 7, 2010

(65) Prior Publication Data

US 2012/0093785 A1    Apr. 19, 2012

Related U.S. Application Data

(62) Division of application No. 10/530,207, filed as application No. PCT/JP03/12734 on Oct. 3, 2003, now abandoned.

(30) Foreign Application Priority Data

Oct. 4, 2002    (JP) ................................. 2002-292853

(51) Int. Cl.
*A61K 48/00*    (2006.01)
*C07H 21/00*    (2006.01)
*C12N 15/85*    (2006.01)

(52) U.S. Cl.
USPC .......................... 435/320.1; 514/44; 536/23.1

(58) Field of Classification Search
USPC .......................... 435/320.1; 514/44; 536/23.1
See application file for complete search history.

(56) References Cited

U.S. PATENT DOCUMENTS 5,942,435 A    8/1999    Wheeler

FOREIGN PATENT DOCUMENTS

EP    1106061 A1    6/2001
WO    02/070648 A2    9/2002

OTHER PUBLICATIONS

Korean Office Action dated Oct. 18, 2010, as issued in Korean Patent Application No. 10-2005-7005701.
Kuroiwa, Yoshimi et al., "Manipulation of human minichromosomes to carry greater than megabase-sized chromosome inserts", Nature Biotechnology, vol. 18, pp. 1086-1090, Oct. 18, 2000.
Grimes, Brenda R., et al., "Alpha-Satellite DNA and Vector Composition Influence Rates of Human Artificial Chromosome Formation", Molecular Therapy, vol. 5, No. 6, pp. 798-805, May 2002.
T. Shinohara et al, "Stability of transferred human chromosome fragments in cultured cells and in mice," Chromosome Research, 2000, vol. 8, pp. 713-725.

Rasheed et al, "Characterization of a Newly Derived Human Sarcoma Cell Line (HT-1080)," Cancer, 1974, vol. 33, pp. 1027-1033.
R. Moreadith et al, "Gene targeting in embryonic stem cells: the new physiology and metabolism," J Mol Med, 1997, vol. 75, pp. 208-216.
L. Mullins et al, "Perspective Series: Molecular Medicine in Genetically Engineered Animals: Transgenesis in the Rat and Larger Animals," Journal of Clinical Investigation, 1996, vol. 97, No. 7, pp. 1557-1560.
M. Pera et al, "Human embryonic stem cells," Journal of Cell Science, 2000, vol. 113, pp. 5-10.
Hattori et al, "The DNA sequence of human chromosome 21," Nature, 2000, vol. 405, No. 6784, pp. 311-319.
European Search Report dated May 18, 2006 for counterpart application PCT/JP0312734 to parent U.S. Appl. No. 10/530,207.
Y. Kuroiwa et al, "Efficient modification of a human chromosome by telomere-directed truncation in high homologous recombination-proficient chicken DT40 cells," Nucleic Acids. Res., 1998, vol. 26, No. 14, pp. 3447-3448.
Y. Kuroiwa et al, "Manipulation of human minichromosomes to carry greater than megabase-sized chromosome inserts," Nature Biotechnology, 2000, vol. 18, No. 10, pp. 1086-1090.
Y. Kuroiwa et al, "Cloned transchromosomic calves producing human immunoglobin," Nature Biotechnology, 2002, vol. 20, No. 9, pp. 889-894.
W. Mills et al, "Generation of an approximately 2.4 Mb human X centromere-based minichromosome by targeted telomere-associated chromosome fragmentation in DT40" Human Molecular Genetics, 1999, vol. 8, No. 5, pp. 751-761.
Z. Larin et al, "Advances in human artificial chromosome technology," Trends. Genet., 2002, vol. 18, No. 6, pp. 313-319.
M. Ikeno et al, "Generation of human artificial chromosomes expressing naturally controlled guanosine triphosphate cyclohydrolase I gene," Genes Cells, 2002, vol. 7, No. 10, pp. 1021-1032.
BR. Grimes et al, "Alpha-satellite DNA and vector composition influence rates of human artificial chromosome formation," Mol. Ther., 2002, vol. 5, No. 6, pp. 798-805.
H. Masumuto et al, "Centromere Kinetochore no Kino Kozo Hito Jinko Senshokutai o Mochiita Kino Kaiseki," Protein, Nucleic Acid and Enzyme, 1999, vol. 44, No. 12, pp. 1665-1673.
K. Tomizuka et al, "Double trans-chomosomic mice: maintenance of two individual human chromosome fragments containing Ig heavy and kappa loci and expression of fully human antibodies," Proc. Natl. Acad. Sci. USA, 2000, vol. 97. No. 2, pp. 722-727
JW. Yang et al, "Human mini-chromosomes with minimal centromeres," Hum. Mol. Genet. 2000, vol. 9, No. 12, pp. 1891-1902.
JM. Robl et al., "Artificial chromosome vectors and expression of complex proteins in transgenic animals," Theriogenology, 2003, vol. 59, No. 1, pp. 107-113.
R. Saffery et al, "Strategies for engineering human chromosomes with theraputic potential," The Journal of Gene Medicine, 2002, vol. 4, pp. 5-13.
M. Katoh et al, "Construction of a novel human artificial chromosome vector for gene delivery," Biochemical and Biophysical Research Communications, 2004, vol. 321, pp. 280-290.
International Search Report dated Jan. 20, 2004 for counterpart application PCT/JP0312734 to parent U.S. Appl. No. 10/530,207. .

(Continued)

*Primary Examiner* — Kevin Hill
(74) *Attorney, Agent, or Firm* — Sughrue Mion, PLLC

(57) ABSTRACT

The present invention relates to a human artificial chromosome (HAC) vector and a method for producing the same. The present invention further relates to a method for introducing foreign DNA using a human artificial chromosome vector and a method for producing a cell which expresses foreign DNA. Furthermore, the present invention relates to a method for producing a protein.

5 Claims, 22 Drawing Sheets
(12 of 22 Drawing Sheet(s) Filed in Color)

(56) References Cited

OTHER PUBLICATIONS

European Search Report dated Feb. 15, 2006 for counterpart application PCT/JP0312734 to parent U.S. Appl. No. 10/530,207.

H. Masumoto et al, "Assay of centromere function using a human artificial chromosome," 1998, Chromosoma vol. 107, pp. 406-416.

Japanese Office Action issued Sep. 20, 2011 for counterpart Japanese application 2009-185530.

Fig. 19

| PCR markers | CHO(#21) ΔqGFP#7 | E14(#21)neo 1 | E14(#21)neo 11 | E14(#21)neo 13 | E14(#21)neo 14 | E14(#21)neo 20 | CHO(#21) Hyg8 | E14(#21)Hyg 1 | E14(#21)Hyg 2 |
|---|---|---|---|---|---|---|---|---|---|
| PCHB | + | + | − | − | − | + | − | − | − |
| D21S187 | + | + | − | − | − | − | − | − | − |
| #21p76957/ 77555 | − | − | − | − | − | − | − | − | − |
| HygroF/ HygroR | + | + | − | − | − | − | + | + | + |
| Hyg968/ #21p96705 | + | + | − | − | − | − | + | + | + |
| #21p91203/ 91976 | + | + | + | + | − | − | + | + | + |
| Spe31203/Bam36192 | + | + | − | + | − | − | + | + | + |
| D21S275 | + | + | − | − | − | + | + | − | + |
| <centromere> | | | | | | | | | |
| PRED65F/ PRED65R | + | + | − | − | − | − | + | + | − |
| PRED3F/ PRED3R | + | + | − | − | − | − | + | + | − |
| #21qEcoF/ #21qEcoR | + | + | − | − | − | − | + | + | + |
| Left455F/ Left638R | + | + | − | + | − | − | + | + | + |
| Right958F/ Right1152R | + | + | − | − | + | − | + | + | + |
| #21qBaF/ #21qBaR | + | + | − | − | + | − | + | + | + |

SEQUENCE LISTING

```
<160> NUMBER OF SEQ ID NOS: 62

<210> SEQ ID NO 1
<211> LENGTH: 37
<212> TYPE: DNA
<213> ORGANISM: Artificial
<220> FEATURE:
<223> OTHER INFORMATION: synthetic oligonucleotide

<400> SEQUENCE: 1
cgcggatcca gagagagcct ggaatgcctg gtagtgt                               37

<210> SEQ ID NO 2
<211> LENGTH: 37
<212> TYPE: DNA
<213> ORGANISM: Artificial
<220> FEATURE:
<223> OTHER INFORMATION: synthetic oligonucleotide

<400> SEQUENCE: 2
cgcggatccc cagtgccctg agatcttgtg atttctc                               37

<210> SEQ ID NO 3
<211> LENGTH: 20
<212> TYPE: DNA
<213> ORGANISM: Artificial
<220> FEATURE:
<223> OTHER INFORMATION: synthetic oligonucleotide

<400> SEQUENCE: 3
gcctggcatc ttcctcaata                                                  20

<210> SEQ ID NO 4
<211> LENGTH: 20
<212> TYPE: DNA
<213> ORGANISM: Artificial
<220> FEATURE:
<223> OTHER INFORMATION: synthetic oligonucleotide

<400> SEQUENCE: 4
ttgcatgcct gtggtactgt                                                  20

<210> SEQ ID NO 5
<211> LENGTH: 20
```

```
<212> TYPE: DNA
<213> ORGANISM: Artificial
<220> FEATURE:
<223> OTHER INFORMATION: synthetic oligonucleotide

<400> SEQUENCE: 5
tcacaatcat gggctttgaa                                              20

<210> SEQ ID NO 6
<211> LENGTH: 20
<212> TYPE: DNA
<213> ORGANISM: Artificial
<220> FEATURE:
<223> OTHER INFORMATION: synthetic oligonucleotide

<400> SEQUENCE: 6
cacgcaacca tttgttcatt                                              20

<210> SEQ ID NO 7
<211> LENGTH: 20
<212> TYPE: DNA
<213> ORGANISM: Artificial
<220> FEATURE:
<223> OTHER INFORMATION: synthetic oligonucleotide

<400> SEQUENCE: 7
tcacagccag cagaggattc                                              20

<210> SEQ ID NO 8
<211> LENGTH: 20
<212> TYPE: DNA
<213> ORGANISM: Artificial
<220> FEATURE:
<223> OTHER INFORMATION: synthetic oligonucleotide

<400> SEQUENCE: 8
cacctgcaca atggctcaac                                              20

<210> SEQ ID NO 9
<211> LENGTH: 29
<212> TYPE: DNA
<213> ORGANISM: Artificial
<220> FEATURE:
<223> OTHER INFORMATION: synthetic oligonucleotide

<400> SEQUENCE: 9
ccggaattcc tctgggtttc tggtgaagc                                    29

<210> SEQ ID NO 10
<211> LENGTH: 29
<212> TYPE: DNA
<213> ORGANISM: Artificial
<220> FEATURE:
<223> OTHER INFORMATION: synthetic oligonucleotide

<400> SEQUENCE: 10
ccggaattct gtagatcctg ccattgtgg                                    29

<210> SEQ ID NO 11
<211> LENGTH: 29
<212> TYPE: DNA
<213> ORGANISM: Artificial
<220> FEATURE:
<223> OTHER INFORMATION: synthetic oligonucleotide

<400> SEQUENCE: 11
cgcggatcct tggctccaaa aggtaccac                                    29
```

<210> SEQ ID NO 12
<211> LENGTH: 29
<212> TYPE: DNA
<213> ORGANISM: Artificial
<220> FEATURE:
<223> OTHER INFORMATION: synthetic oligonucleotide

<400> SEQUENCE: 12
cgcggatccc tatcctcgcc actgtgtcc                              29

<210> SEQ ID NO 13
<211> LENGTH: 25
<212> TYPE: DNA
<213> ORGANISM: Artificial
<220> FEATURE:
<223> OTHER INFORMATION: synthetic oligonucleotide

<400> SEQUENCE: 13
gttgcagaaa agtagactgt agcaa                                  25

<210> SEQ ID NO 14
<211> LENGTH: 25
<212> TYPE: DNA
<213> ORGANISM: Artificial
<220> FEATURE:
<223> OTHER INFORMATION: synthetic oligonucleotide

<400> SEQUENCE: 14
tctaaggaac aaatctaggt catgg                                  25

<210> SEQ ID NO 15
<211> LENGTH: 20
<212> TYPE: DNA
<213> ORGANISM: Artificial
<220> FEATURE:
<223> OTHER INFORMATION: synthetic oligonucleotide

<400> SEQUENCE: 15
gggctagcca ttaaagctga                                        20

<210> SEQ ID NO 16
<211> LENGTH: 20
<212> TYPE: DNA
<213> ORGANISM: Artificial
<220> FEATURE:
<223> OTHER INFORMATION: synthetic oligonucleotide

<400> SEQUENCE: 16
aaagggaata agggcgacac                                        20

<210> SEQ ID NO 17
<211> LENGTH: 24
<212> TYPE: DNA
<213> ORGANISM: Artificial
<220> FEATURE:
<223> OTHER INFORMATION: synthetic oligonucleotide

<400> SEQUENCE: 17
ggtttgtcca aactcatcaa tgta                                   24

<210> SEQ ID NO 18
<211> LENGTH: 27
<212> TYPE: DNA
<213> ORGANISM: Artificial
<220> FEATURE:
<223> OTHER INFORMATION: synthetic oligonucleotide -continued

<400> SEQUENCE: 18
gtcaattcac taattcctat tcccagt                                27

<210> SEQ ID NO 19
<211> LENGTH: 20
<212> TYPE: DNA
<213> ORGANISM: Artificial
<220> FEATURE:
<223> OTHER INFORMATION: synthetic oligonucleotide

<400> SEQUENCE: 19
caacagcatc cccatctctg                                        20

<210> SEQ ID NO 20
<211> LENGTH: 20
<212> TYPE: DNA
<213> ORGANISM: Artificial
<220> FEATURE:
<223> OTHER INFORMATION: synthetic oligonucleotide

<400> SEQUENCE: 20
gctcaagatg cccctgttct                                        20

<210> SEQ ID NO 21
<211> LENGTH: 28
<212> TYPE: DNA
<213> ORGANISM: Artificial
<220> FEATURE:
<223> OTHER INFORMATION: synthetic oligonucleotide

<400> SEQUENCE: 21
ggccgaattc cgtattaccg ccatgcat                               28

<210> SEQ ID NO 22
<211> LENGTH: 27
<212> TYPE: DNA
<213> ORGANISM: Artificial
<220> FEATURE:
<223> OTHER INFORMATION: synthetic oligonucleotide

<400> SEQUENCE: 22
ccgggatccc acaactagaa tgcagtg                                27

<210> SEQ ID NO 23
<211> LENGTH: 28
<212> TYPE: DNA
<213> ORGANISM: Artificial
<220> FEATURE:
<223> OTHER INFORMATION: synthetic oligonucleotide

<400> SEQUENCE: 23
gcactagtct ggcactcctg cataaaca                               28

<210> SEQ ID NO 24
<211> LENGTH: 30
<212> TYPE: DNA
<213> ORGANISM: Artificial
<220> FEATURE:
<223> OTHER INFORMATION: synthetic oligonucleotide

<400> SEQUENCE: 24
ctaaggatcc atttcagcct gtgggaatca                             30

<210> SEQ ID NO 25
<211> LENGTH: 20

```
<212> TYPE: DNA
<213> ORGANISM: Artificial
<220> FEATURE:
<223> OTHER INFORMATION: synthetic oligonucleotide

<400> SEQUENCE: 25
ctggcactcc tgcataaaca                                              20

<210> SEQ ID NO 26
<211> LENGTH: 20
<212> TYPE: DNA
<213> ORGANISM: Artificial
<220> FEATURE:
<223> OTHER INFORMATION: synthetic oligonucleotide

<400> SEQUENCE: 26
tctgtgttcc ccttctctga                                              20

<210> SEQ ID NO 27
<211> LENGTH: 24
<212> TYPE: DNA
<213> ORGANISM: Artificial
<220> FEATURE:
<223> OTHER INFORMATION: synthetic oligonucleotide

<400> SEQUENCE: 27
aagtactcgc cgatagtgga aacc                                         24

<210> SEQ ID NO 28
<211> LENGTH: 24
<212> TYPE: DNA
<213> ORGANISM: Artificial
<220> FEATURE:
<223> OTHER INFORMATION: synthetic oligonucleotide

<400> SEQUENCE: 28
agttagccta cctttggcc atcc                                          24

<210> SEQ ID NO 29
<211> LENGTH: 39
<212> TYPE: DNA
<213> ORGANISM: Artificial
<220> FEATURE:
<223> OTHER INFORMATION: synthetic oligonucleotide

<400> SEQUENCE: 29
cgggatccct cgagcgagac atgataagat acattgatg                         39

<210> SEQ ID NO 30
<211> LENGTH: 39
<212> TYPE: DNA
<213> ORGANISM: Artificial
<220> FEATURE:
<223> OTHER INFORMATION: synthetic oligonucleotide

<400> SEQUENCE: 30
ggaagatctt cctaatcagc cataccacat ttgtagagg                         39

<210> SEQ ID NO 31
<211> LENGTH: 39
<212> TYPE: DNA
<213> ORGANISM: Artificial
<220> FEATURE:
<223> OTHER INFORMATION: synthetic oligonucleotide

<400> SEQUENCE: 31
cggaattccg gacattgatt attgactagt tattaatag                         39
```

<210> SEQ ID NO 32
<211> LENGTH: 36
<212> TYPE: DNA
<213> ORGANISM: Artificial
<220> FEATURE:
<223> OTHER INFORMATION: synthetic oligonucleotide

<400> SEQUENCE: 32
cgggatcccg ggtgtcttct atggaggtca aaacag                        36

<210> SEQ ID NO 33
<211> LENGTH: 35
<212> TYPE: DNA
<213> ORGANISM: Artificial
<220> FEATURE:
<223> OTHER INFORMATION: synthetic oligonucleotide

<400> SEQUENCE: 33
cgggatcccg gccaccatgg gggtgcacga atgtc                         35

<210> SEQ ID NO 34
<211> LENGTH: 33
<212> TYPE: DNA
<213> ORGANISM: Artificial
<220> FEATURE:
<223> OTHER INFORMATION: synthetic oligonucleotide

<400> SEQUENCE: 34
cgctcgagcg ctatctgtcc cctgtcctgc agg                           33

<210> SEQ ID NO 35
<211> LENGTH: 35
<212> TYPE: DNA
<213> ORGANISM: Artificial
<220> FEATURE:
<223> OTHER INFORMATION: synthetic oligonucleotide

<400> SEQUENCE: 35
ggaattccgg gcccacgcgt gacattgatt attga                         35

<210> SEQ ID NO 36
<211> LENGTH: 35
<212> TYPE: DNA
<213> ORGANISM: Artificial
<220> FEATURE:
<223> OTHER INFORMATION: synthetic oligonucleotide

<400> SEQUENCE: 36
ggaattcctg atcataatca gccataccac atttg                         35

<210> SEQ ID NO 37
<211> LENGTH: 26
<212> TYPE: DNA
<213> ORGANISM: Artificial
<220> FEATURE:
<223> OTHER INFORMATION: synthetic oligonucleotide

<400> SEQUENCE: 37
tttgcatgtc tttagttcta tgatga                                   26

<210> SEQ ID NO 38
<211> LENGTH: 23
<212> TYPE: DNA
<213> ORGANISM: Artificial
<220> FEATURE:
<223> OTHER INFORMATION: synthetic oligonucleotide

```
<400> SEQUENCE: 38
aggtcggtct tgacaaaaag aac                                            23

<210> SEQ ID NO 39
<211> LENGTH: 17
<212> TYPE: DNA
<213> ORGANISM: Artificial
<220> FEATURE:
<223> OTHER INFORMATION: synthetic oligonucleotide

<400> SEQUENCE: 39
caggaaacag ctatgac                                                   17

<210> SEQ ID NO 40
<211> LENGTH: 26
<212> TYPE: DNA
<213> ORGANISM: Artificial
<220> FEATURE:
<223> OTHER INFORMATION: synthetic oligonucleotide

<400> SEQUENCE: 40
tttgcatgtc tttagttcta tgatga                                         26

<210> SEQ ID NO 41
<211> LENGTH: 23
<212> TYPE: DNA
<213> ORGANISM: Artificial
<220> FEATURE:
<223> OTHER INFORMATION: synthetic oligonucleotide

<400> SEQUENCE: 41
aggtcggtct tgacaaaaag aac                                            23

<210> SEQ ID NO 42
<211> LENGTH: 23
<212> TYPE: DNA
<213> ORGANISM: Artificial
<220> FEATURE:
<223> OTHER INFORMATION: synthetic oligonucleotide

<400> SEQUENCE: 42
ctacccgtga tattgctgaa gag                                            23

<210> SEQ ID NO 43
<211> LENGTH: 21
<212> TYPE: DNA
<213> ORGANISM: Artificial
<220> FEATURE:
<223> OTHER INFORMATION: synthetic oligonucleotide

<400> SEQUENCE: 43
atttgcactg ccggtagaac t                                              21

<210> SEQ ID NO 44
<211> LENGTH: 19
<212> TYPE: DNA
<213> ORGANISM: Artificial
<220> FEATURE:
<223> OTHER INFORMATION: synthetic oligonucleotide

<400> SEQUENCE: 44
ctgctgcgca cgtgggaag                                                 19

<210> SEQ ID NO 45
<211> LENGTH: 20
```

```
<212> TYPE: DNA
<213> ORGANISM: Artificial
<220> FEATURE:
<223> OTHER INFORMATION: synthetic oligonucleotide

<400> SEQUENCE: 45
ggtctggcag gtgacaccac                                              20

<210> SEQ ID NO 46
<211> LENGTH: 35
<212> TYPE: DNA
<213> ORGANISM: Artificial
<220> FEATURE:
<223> OTHER INFORMATION: synthetic oligonucleotide

<400> SEQUENCE: 46
gaagatcttc atcgatcggc caccatgccg cgcgc                             35

<210> SEQ ID NO 47
<211> LENGTH: 20
<212> TYPE: DNA
<213> ORGANISM: Artificial
<220> FEATURE:
<223> OTHER INFORMATION: synthetic oligonucleotide

<400> SEQUENCE: 47
tcactcggtc cacgcgtcct                                              20

<210> SEQ ID NO 48
<211> LENGTH: 20
<212> TYPE: DNA
<213> ORGANISM: Artificial
<220> FEATURE:
<223> OTHER INFORMATION: synthetic oligonucleotide

<400> SEQUENCE: 48
agtgccagcc gaagtctgcc                                              20

<210> SEQ ID NO 49
<211> LENGTH: 19
<212> TYPE: DNA
<213> ORGANISM: Artificial
<220> FEATURE:
<223> OTHER INFORMATION: synthetic oligonucleotide

<400> SEQUENCE: 49
gcagctgaac agtgccttc                                               19

<210> SEQ ID NO 50
<211> LENGTH: 20
<212> TYPE: DNA
<213> ORGANISM: Artificial
<220> FEATURE:
<223> OTHER INFORMATION: synthetic oligonucleotide

<400> SEQUENCE: 50
aggacgcgtg gaccgagtga                                              20

<210> SEQ ID NO 51
<211> LENGTH: 27
<212> TYPE: DNA
<213> ORGANISM: Artificial
<220> FEATURE:
<223> OTHER INFORMATION: synthetic oligonucleotide

<400> SEQUENCE: 51
ccatcctaat acgactcact atagggc                                      27
```

```
<210> SEQ ID NO 52
<211> LENGTH: 35
<212> TYPE: DNA
<213> ORGANISM: Artificial
<220> FEATURE:
<223> OTHER INFORMATION: synthetic oligonucleotide

<400> SEQUENCE: 52
ccgagcgtct cacctcgagg gtgaaggcac tgttc                            35

<210> SEQ ID NO 53
<211> LENGTH: 24
<212> TYPE: DNA
<213> ORGANISM: Artificial
<220> FEATURE:
<223> OTHER INFORMATION: synthetic oligonucleotide

<400> SEQUENCE: 53
atggactacg tcgtgggagc caga                                       24

<210> SEQ ID NO 54
<211> LENGTH: 35
<212> TYPE: DNA
<213> ORGANISM: Artificial
<220> FEATURE:
<223> OTHER INFORMATION: synthetic oligonucleotide

<400> SEQUENCE: 54
gtcgacgcta gctcagtcca ggatggtctt gaagt                            35

<210> SEQ ID NO 55
<211> LENGTH: 20
<212> TYPE: DNA
<213> ORGANISM: Artificial
<220> FEATURE:
<223> OTHER INFORMATION: synthetic oligonucleotide

<400> SEQUENCE: 55
gcgaagaatc tcgtgctttc                                            20

<210> SEQ ID NO 56
<211> LENGTH: 20
<212> TYPE: DNA
<213> ORGANISM: Artificial
<220> FEATURE:
<223> OTHER INFORMATION: synthetic oligonucleotide

<400> SEQUENCE: 56
ataggtcagg ctctcgctga                                            20

<210> SEQ ID NO 57
<211> LENGTH: 20
<212> TYPE: DNA
<213> ORGANISM: Artificial
<220> FEATURE:
<223> OTHER INFORMATION: synthetic oligonucleotide

<400> SEQUENCE: 57
gccatccacg ctgttttgac                                            20

<210> SEQ ID NO 58
<211> LENGTH: 20
<212> TYPE: DNA
<213> ORGANISM: Artificial
<220> FEATURE:
<223> OTHER INFORMATION: synthetic oligonucleotide
```

```
<400> SEQUENCE: 58
gcatcagagc agccgattgt                                              20

<210> SEQ ID NO 59
<211> LENGTH: 22
<212> TYPE: DNA
<213> ORGANISM: Artificial
<220> FEATURE:
<223> OTHER INFORMATION: synthetic oligonucleotide

<400> SEQUENCE: 59
acacttttga caaacacacc ag                                           22

<210> SEQ ID NO 60
<211> LENGTH: 21
<212> TYPE: DNA
<213> ORGANISM: Artificial
<220> FEATURE:
<223> OTHER INFORMATION: synthetic oligonucleotide

<400> SEQUENCE: 60
tcaacaatga aaggggatgt c                                            21

<210> SEQ ID NO 61
<211> LENGTH: 20
<212> TYPE: DNA
<213> ORGANISM: Artificial
<220> FEATURE:
<223> OTHER INFORMATION: synthetic oligonucleotide

<400> SEQUENCE: 61
tgaatgaact gcaggacgag                                              20

<210> SEQ ID NO 62
<211> LENGTH: 20
<212> TYPE: DNA
<213> ORGANISM: Artificial
<220> FEATURE:
<223> OTHER INFORMATION: synthetic oligonucleotide

<400> SEQUENCE: 62
atactttctc ggcaggagca                                              20
```

HUMAN ARTIFICIAL CHROMOSOME (HAC) VECTOR

CROSS REFERENCE TO RELATED APPLICATIONS

The present application is a divisional of U.S. application Ser. No. 10/530,207, filed Feb. 13, 2006 (abandoned), which is the U.S. National Phase of PCT/JP03/12734 filed Oct. 3, 2003 which claims priority from Japanese Patent Application No. 2002/292853 filed Oct. 4, 2002. Each of the foregoing applications is incorporated by reference herein in its entirety.

TECHNICAL FIELD

The present invention relates to a human artificial chromosome (HAC) vector and a method for producing the same. The present invention further relates to a method for introducing foreign DNA using a human artificial chromosome vector and a method for producing a cell which expresses foreign DNA. Furthermore, the present invention relates to a method for producing a protein.

BACKGROUND ART

A vector for introducing and expressing an foreign gene in mammalian cells is not only an essential tool for the study of basic life science, but it has also played an important role in applying the results to practical use in industry (for example, large-scale production of drugs) and clinical practice (for example, gene therapy). Progress in genetic engineering technology after the later half of the 1970's facilitated the isolation and amplification of particular gene DNA fragments (gene cloning) using *Escherichia coli* and yeast. Cloned DNA has been used conventionally for gene transfer to mammalian cells. In common practice, an artificial expression unit containing the coding region of a gene to be expressed (cDNA) linked with a promoter and a poly A addition site which are functional in mammalian cells has been prepared, or *E. coli* plasmid (a maximum of about 20 kb, cyclic), cosmid (a maximum of about 40 kb, cyclic), a bacteria artificial chromosome (BAC, maximum 200 kb, cyclic), and a yeast artificial chromosome (YAC, maximum 1 Mb, linear) which contain a genomic DNA fragment containing an original promoter and a poly A addition site as well as the coding region have been prepared in cyclic or linear form, and these have been transferred into cells by transfection or injection. When the introduced vector DNA has no origin of replication derived from a mammal, expression of the introduced gene will become transient because it is incapable of replication in the host cells and will be omitted during cell divisions. If the vector has an origin of replication, it produces a number of copies in the cells temporarily; however, they will be omitted gradually in the absence of selection pressure due to unequal partition to daughter cells during cell divisions. Therefore, expression is transient in this case as well. It is possible to select cell lines which express introduced genes in a constitutive manner by introducing a drug resistant gene simultaneously and applying drug selection pressure, though the introduced gene is incorporated into the chromosome of the host cell (integration). Integration affects both the introduced gene and the host chromosomes. Genes in the host chromosome may be destroyed (Pravtcheva et al., Genomics (USA), Vol. 30, p. 529-544, 1995). For the introduced gene, the number of copies may not be controlled, the copies may be inactivated (Garrick et al., Nature Genet. (USA), Vol. 18, p. 56-59, 1998) or affected by the control sequence on the host chromosome into which the gene has been integrated (Dobie et al., P.N.A.S. (USA), Vol. 93, p. 6659-6664, 1996; Alami et al., Hum. Mol. Genet. (UK), Vol. 9, p. 631-636, 2000). Thus, there is a need for the development of a method of introducing a given number of gene copies without destroying the host chromosome. A solution to such problems is to construct an artificial chromosome capable of autonomous replication/partition in host cells from animals including humans and to introduce genes into animal cells using this as a vector.

(1) Construction of a Human Artificial Chromosome (HAC)

Construction of human artificial chromosomes (hereinafter referred to as "HAC") available in animal cells has been attempted in order to generate a vector to express foreign genes and, in biological terms, to identify the structure required for autonomous replication/partition in cells. There are three types of approaches to constructing HACs, i.e. (A) bottom up approach, (B) use of spontaneous chromosome fragments and (C) top-down approach (a natural chromosome is trimmed).

(A) Bottom Up Approach

The DNA sequence which is necessary for autonomous replication/partition has been identified in *E. coli* and yeast, and an artificial chromosome that provides for a given number of copies in host cells has been established (BAC or YAC). Similarly, an attempt has been made to use the bottom up approach to establish a HAC by introducing a cloned DNA fragment of a known sequence into animal cells and assembling the DNA fragment. A drug resistant gene derived from a YAC which contains an alphoid sequence of about 100 kb, which is a component of the human chromosome centromere, and a human telomere sequence were added and introduced into human fibrosarcoma cell line HT1080 (Ikenno et al., Nature Biotech. (USA), Vol. 16, p. 431-439, 1998). For the drug resistance cell clone, artificial chromosomes capable of autonomous replication/partition have been established; however, it is not that the introduced DNA sequence itself is maintained in the cell, but that reconstitution by amplification has occurred, and the sequence structure maintained by the cell is not clear.

In addition, the objective of the above research was to establish a HAC, and no research has been done to insert foreign genes.

(B) Use of Spontaneous Chromosome Fragments

A chromosome itself is an aggregate of genes, and possesses the elements required for autonomous replication/partition. Microcell mediated chromosome transfer has allowed for using a chromosome or fragments thereof as a tool for gene transfer in order to introduce a giant gene on the order of Mb, which exceeds the capacity of existing cloning vectors such as YAC. Fragments of human chromosomes 14, 2 and 22 including an antibody gene were transferred into mouse embryonic stem cells, and results showed that chimeras were produced, the antibody gene was expressed in the mice, the human chromosome fragments were retained stably in the chimeras and transmitted to the following generations through germ lines (Tomizuka et al., Nature Genet. (USA), Vol. 16, p. 133-143, 1997; Tomizuka et al., P.N.A.S. (USA), Vol. 97, p. 722-727, 2000). This example demonstrated the effectiveness of using the chromosome carrying the gene to be expressed as a vector. However, it is not realistic to modify chromosomes for every target gene. Desirably, a chromosome vector serving as a base structure is provided into which a target gene is easily inserted in order to take advantage of chromosome fragments as a vector and increase their versatility.

To that end, an attempt was made to use natural chromosome fragments to express foreign genes. The introduction and functional expression of the IL-2 gene (cDNA) or CFTR gene (human genome DNA) using an irradiated chromosome fragment (5.5 Mb) derived from human chromosome 1 as a vector has been reported (see for example, Guiducci et al., Hum. Mol. Genet. (UK), Vol. 8, p. 1417-1424, 1999; Auriche et al., EMBO Rep. (UK), Vol. 2, p. 102-107, 2002.) Hamster fibroblasts (CHO) were used as the host. In introducing a target gene into the fragmented minichromosome, alphoid DNA was used based on the hope that it would be inserted into the centromere domain of human chromosome 1; however, no particular insertion site or the copy number was identified. IL-2 dependent mouse lymphoblast cells became multiplicable in the IL-2-independent manner as a result of cell fusion with the CHO cell that retained IL-2 minichromosome, indicating functional complementarity. In addition, release of chlorine ion by stimulation with cAMP was observed in the CHO cell which retained the CFTR minichromosome, and the release of chlorine ion was suppressed by addition of a CFTR inhibitor. These showed systems for the insertion/expression of foreign genes using chromosome fragments as a vector, but the structure was not made clear and the insertion of foreign DNA was not controlled.

Chromosome fragments (2-3 Mb) derived from an irradiated hybrid cell were retained stably in hamster cells, which contained the centromere and a portion of the long arm of human chromosome 1, and the SDHC (succinate dehydrogenase complex, subunit C) gene. The G418 resistance gene was inserted by homologous recombination at the SDHC region. X-ray cell fusion was performed with mouse cells (L and 3T3), giving G418 resistance hybrid cells (Au et al., Cytogenet. Cell Genet. (Switzerland), Vol. 86, p. 194-203, 1999). This HAC has unknown structure because it uses natural chromosome fragments. Homologous recombination was used to introduce foreign genes into the HAC in a site-specific manner, though this approach had low insertion efficiency and was unsuitable for general purposes. Because the micronucleate cell fusion method was not used, host chromosomes were also present in addition to the target chromosome fragment. This only suggested the idea of expressing foreign genes using chromosomes as a vector.

In addition, by random insertion of a loxP site into a natural chromosome fragment (cyclic), a foreign gene (hygromycin resistance gene) was inserted using reconstitution of the drug resistance gene (hprt) as an indicator (Voet et al., Genome Res. (USA), Vol. 11, p. 124-136, 2001). This circular chromosome includes the centromere of human chromosome 20 and a portion of chromosome 1 (p22 region); however, its sequence has not been identified because it is a natural fragment. A foreign gene was introduced by site-specific recombination with a Cre/loxP system, though its constitution is unknown because the insertion of loxP into the chromosome is randomly occurred. Meanwhile, transfer into mouse ES cells, production of chimeras, and transmission to the progeny by microcell fusion have been shown. Although the method of inserting a target gene into an artificial chromosome is simple excepting that a natural chromosome fragment was used and loxP sites were randomly inserted, using an aberrant chromosome from a patient (mild mental retardation) is problematic in terms of safety and impractical.

(C) Top Down Approach

When a natural chromosome fragment is transferred into cells, many genes from the transferred chromosome fragment other than the target gene will be expressed at the same time. In an experiment of mouse ES cells, it is known that stability varies depending on the human chromosome used, and the contribution of cells retaining introduced chromosome fragments in chimeras decreases as the chromosome fragment increases in size. It is supposed that extra genetic expression disturbs propagation of host cells retaining chromosome fragments. Therefore it is thought that introduced chromosome fragments may be retained at higher rates by removing extra genes through modification of chromosomes.

A technology to shorten a chromosome by introducing a cloned telomere sequence by homologous recombination (telomere truncation) has been described as a method for deleting part of a chromosome (Itzhaki et al., Nature Genet. (USA), Vol. 2, p. 283-287, 1992). However, somatic cells of most animal species have extremely low homologous recombination frequency so that a lot of effort is required to obtain recombinants. Use of chicken cell line DT40 with high frequency homologous recombination as a host enabled efficient chromosome modification (Kuroiwa et al., Nucleic Acids Res. (UK), Vol. 26, p. 3447-8, 1998). The human X chromosome was transferred into the DT40 cell line by the microcell fusion method followed by telomere truncation (Mills et al., Hum. Mol. Genet. (UK), Vol. 8, p. 751-761, 1999). A linear minichromosome of 2.4 Mb was established by removing the short and long arms. The minichromosome was retained stably in hamster and human cells, though the copy number varied. Although stability of HACs was confirmed, no foreign gene was introduced so as to use them as a vector.

In addition, the human Y-chromosome in hamster cells was shortened by telomere truncation to establish a minichromosome of about 4 Mb which was retained stably in host cells (Heller et al., P.N.A.S. (USA), Vol. 93, p. 7125-7130, 1996). This minichromosome was transferred into mouse ES cells by the microcell fusion method, but was unstable. When chimeric mice were generated because the derivative minichromosome which integrated the mouse centromere sequence by chromosome reconstitution acquired stability in ES cells (Shen et al., Hum. Mol. Genet. (UK), Vol. 6, p. 1375-1382, 1997), germ line transmission was confirmed (Shen et al., Curr. Biol. (UK), Vol. 10, p. 31-34, 2000). A chimeric chromosome was shown to be retained in mice, but its structure is unknown because of chromosome reconstitution and no research was done for the introduction/expression of foreign genes.

(2) Insertion of Foreign Genes into HACs

Similarly important to the establishment of HACs as vectors as described above is the establishment of a method for introducing a target gene into the HAC. However, as described above, the establishment of HACs itself has not yet been completed, and for the introduction of foreign genes, only random insertion of drug resistant genes has been suggested; besides no detailed analysis has been done.

Stability in mice and germ line transmission have been confirmed for the spontaneous fragment SC20 from human chromosome 14, which was isolated to generate a mouse retaining the human antibody heavy chain gene. A method (chromosome cloning) of cloning chromosome regions (regions of human chromosomes 2 and 22 including the antibody light chain genes) of the Mb order by reciprocal translocation was established which used the Cre/loxP system (Kuroiwa et al., Nature Biotech. (USA), Vol. 18, p. 1086-1090, 2000). This method was aimed at establishing the HAC of defined structure that contained no unnecessary genes, and it is effective when applied to giant genes of a size exceeding the capacity of other cloning vectors (for example, YAC), such as antibody genes.

In either case, no HAC vector system has been established to date which satisfies the conditions: 1) the structure has been identified and unnecessary genes have been removed, 2) the HAC vector can be maintained stably in cultured cells and individuals, and 3) foreign DNA can be easily introduced into it.

DISCLOSURE OF THE INVENTION

It is an object of the invention to provide a human artificial chromosome vector which is retained stably in cells, allows for easy insertion of large-size foreign genes and is introduced into cells, and a method for producing the same.

To solve the above problems, the inventors have conducted intensive study to 1) establish a chromosome vector which are free from extra genes and can be retained stably in animal cells and 2) establish an expression system by providing a cloning site for the chromosome vector and inserting a target gene into the cloning site as an expression cassette. Specifically, a modified chromosome was prepared from human chromosome 21 by removing a known gene from its long arm, the stability of DT40 hybrid cells retaining the modified chromosome in long-term subculture was confirmed, a loxP sequence and an hCMV promoter were inserted into the proximal region of the long arm on the modified chromosome in a site-specific manner, the GFP gene was introduced into the modified chromosome using the Cre/loxP system, and expression of GFP was confirmed. The inventors found from the results that the problems described above might be solved by establishing a HAC vector based on fragments from human chromosome 21 and completed the present invention.

The present invention is summarized as follows.

In the first aspect of the present invention, the invention provides a human artificial chromosome vector comprising a fragment of human chromosome 21 or a fragment of human chromosome 14 from which the distal region of the long arm and/or the distal region of the short arm was deleted.

In one embodiment of the invention, the size of the fragment of human chromosome 21 is about 2-16 Mb, and preferably about 2-6 Mb.

In another embodiment of the invention, the distal region of the long arm of human chromosome 21 is deleted, for example within the 21q11 region, and preferably at AL163204.

In another embodiment of the invention, the distal region of the short arm of human chromosome 21 is deleted, for example within the 21p region, and preferably at AL163201.

In another embodiment of the invention, the size of the fragment of human chromosome 14 is about 20 Mb, preferably about 19 Mb or less, more preferably 18 Mb or less.

In another embodiment of the invention, the distal region of the long arm of human chromosome 14 is deleted, for example within the 14q region, preferably at AL157858, more preferably at AL512310.

In addition, the distal region of the short arm of human chromosome 14 is deleted, for example within the 14p region, preferably within the 14p12 region, more preferably at a position selected from the group consisting of OR4H12, OR4Q4, RNR2, OR4L1, RNU6C, FDPSL3, K12T, C14orf57, OR6S1, M195, OR4K14, MGC27165, LCH, OR10G3, OR4K3, OR4E2, H1RNA, ATP5C2, OR11H6 and OR4M1.

In yet another embodiment, the human artificial chromosome vector according to the present invention has a recognition site for site-specific recombination enzyme inserted at the proximal region of the long arm and/or the proximal region of the short arm of human chromosome 21 or human chromosome 14. In a preferred embodiment, the recognition site for site-specific recombination enzyme is inserted into a more proximal region than AL163203 in the proximal region of the long arm of human chromosome 21 or into a more proximal region than AL157858 in the proximal region of the long arm of human chromosome 14, more preferably into a more proximal region than the deletion site of AL512310 or into a more proximal region than the deletion site within the 14p12 region of the proximal region of the short arm of human chromosome 14. In addition, in a preferred embodiment, the site-specific recombination enzyme is Cre enzyme, and the recognition site for the site-specific recombination enzyme is the loxP sequence.

In another embodiment according to the present invention, the deletion of the distal region of the long arm and/or the distal region of the short arm is by substitution with an artificial telomere sequence.

In the second aspect of the present invention, the invention provides a method for producing a human artificial chromosome vector comprising the steps of:

(a) obtaining cells that retain human chromosome 21 or human chromosome 14;

(b) deleting a distal region of the long arm and/or a distal region of the short arm of the human chromosome 21 or human chromosome 14; and (c) inserting a recognition site for a site-specific recombination enzyme into a proximal region of the long arm and/or a proximal region of the short arm of the human chromosome 21 or human chromosome 14.

In one embodiment of the invention, in step (a), the cells that retain human chromosome 21 or human chromosome 14 have high homologous recombination efficiency. In a preferred embodiment, the cells with high homologous recombination efficiency are derived from chicken DT40 cells.

In one embodiment of the invention, in step (b), the distal region of the long arm and/or the distal region of the short arm of human chromosome 21 or human chromosome 14 are deleted by substitution with an artificial telomere sequence. In a preferred embodiment, the distal region of the long arm of human chromosome 21 is deleted at AL163204 and the distal region of the short arm is removed at AL163201. In another preferred embodiment, the distal region of the long arm of human chromosome 14 is removed within the 14q region and the distal region of the short arm is deleted within the 14p12 region. In yet another preferred embodiment, the distal region of the long arm of human chromosome 14 is deleted at AL157858, more preferably at AL512310, and the distal region of the short arm is deleted at a position selected from the group consisting of OR4H12, OR4Q4, RNR2, OR4L1, RNU6C, FDPSL3, K12T, C14orf57, OR6S1, M195, OR4K14, MGC27165, LCH, OR10G3, OR4K3, OR4E2, H1RNA, ATP5C2, OR11H6 and OR4M1.

In yet another embodiment, in step (c), the site-specific recombination enzyme is Cre enzyme, and the recognition site for the site-specific recombination enzyme is the LoxP sequence.

In yet another aspect, the recognition site for site-specific recombination enzyme may be inserted, for example, into a more proximal region than AL163203 in the proximal region of the long arm of human chromosome 21 or into a more proximal region than AL157858 of human chromosome 14, more preferably into a more proximal region than the deletion site of AL512310 or into a more proximal region than the deletion site within the 14p12 region of the proximal region of the short arm of human chromosome 14.

In the third aspect of the present invention, the invention provides a human artificial chromosome vector obtainable by the method described above.

In the fourth aspect, the present invention provides cells that retain the human artificial chromosome vector above.

In the fifth aspect of the present invention, the invention provides the method for producing a human artificial chromosome vector containing foreign DNA, further comprising step (d) below in the method described above:

(d) inserting foreign DNA into human chromosome 21 or human chromosome 14 in the presence of a site-specific recombination enzyme.

In the sixth aspect, the present invention represents a human artificial chromosome vector containing foreign DNA obtainable by the method described above.

In the seventh aspect, the invention provides cells that retain a human artificial chromosome vector comprising foreign DNA.

In the eight aspect, the invention provides a pharmaceutical composition which contains the cells that retain a human artificial chromosome vector comprising foreign DNA. The foreign DNA described above may be a gene encoding erythropoietin (EPO), thrombopoietin (TPO), blood coagulation factor, von Willebrand factor (vWF), dystrophin, dopamine synthase, insulin, insulin-like growth factor (IGF), insulin-like growth factor binding protein (IGFBP), antibody, telomerase, granulocyte colony stimulating factor, granulocyte/macrophage colony stimulating factor, immunoglobulin, growth hormone, interleukin 2, interleukin 3, interleukin 4, interleukin 5, interleukin 6, interleukin 7, interleukin 8, interleukin 9, interleukin 10, interleukin 11, interleukin 12, interleukin 15, CD40 ligand, interferon, adenosine deaminase, alpha-1 antitrypsin, ornithine transcarbamylase, purine nucleotide phosphorylase, growth inhibiting factor (GIF), tumor necrosis factor (TNF), leukemia inhibitory factor (LIF), oncostatin M, Flt3 ligand (Flt3L), stroma derived factor (SDF), stem cell growth factor (SCF), fibroblast growth factor (FGF), epidermal growth factor (EGF), vascular endothelial growth factor (VEGF), angiopoietin, nerve growth factor (NGF), bone morphogenetic factor (BMP), activin, transforming growth factor (TGF) and Wnt.

In the ninth aspect, the invention provides a method for introducing foreign DNA into a recipient cell comprising the steps of:

(a) obtaining donor cells that retain human chromosome 21 or human chromosome 14;

(b) deleting a distal region of the long arm and/or a distal region of the short arm of the human chromosome 21 or human chromosome 14;

(c) inserting a recognition site for a site-specific recombination enzyme into a proximal region of the long arm and/or a proximal region of the short arm of the human chromosome 21 or human chromosome 14;

(d) inserting foreign DNA into the human chromosome 21 or human chromosome 14 in the presence of a site-specific recombination enzyme;

(e) preparing microcells from the donor cells that retain the human chromosome 21 or human chromosome 14;

(f) fusing the microcells and recipient cells; and (g) confirming the introduction of the foreign DNA into the fused recipient cells.

In one embodiment of the invention, the recipient cells described above are animal cells, preferably mammalian cells. In addition, the recipient cells described above may be pluripotent cells, for example, embryonic stem cells (ES cell), and mesenchymal stem cells and tissue stem/precursor cells.

In the tenth aspect, the invention provides a method for producing cells that express foreign DNA comprising the steps of:

(a) obtaining donor cells that retain human chromosome 21 or human chromosome 14;

(b) deleting a distal region of the long arm and/or a distal region of the short arm of the human chromosome 21 or human chromosome 14;

(c) inserting a recognition site for a site-specific recombination enzyme into a proximal region of the long arm and/or a proximal region of the short arm of the human chromosome 21 or human chromosome 14.

(d) inserting foreign DNA into the human chromosome 21 or human chromosome 14 under the expression of a site-specific recombination enzyme.

(e) preparing microcells from the donor cells that retain the human chromosome 21 or human chromosome 14;

(f) fusing the microcells and recipient cells; and (g) selecting cells expressing the foreign DNA among the fused recipient cells.

In one embodiment of the invention, the recipient cells described above are animal cells, preferably mammalian cells. In addition, the recipient cells described above may be pluripotent cells, for example, embryonic stem cells (ES cell), and mesenchymal stem cells and tissue stem/precursor cells.

In the 11th aspect of the present invention, the invention provides a method for producing a protein comprising the steps of:

(a) obtaining donor cells that retain human chromosome 21 or human chromosome 14;

(b) deleting a distal region of the long arm and/or a distal region of the short arm of the human chromosome 21 or human chromosome 14;

(c) inserting a recognition site for a site-specific recombination enzyme into a proximal region of the long arm and/or a proximal region of the short arm of the human chromosome 21 or human chromosome 14.

(d) inserting foreign DNA encoding a protein into the human chromosome 21 or human chromosome 14 described above under the expression of a site-specific recombination enzyme;

(e) preparing microcells from the donor cells that retain the human chromosome 21 or human chromosome 14;

(f) fusing the microcells and recipient cells;

(g) incubating the fused recipient cells in culture media; and (h) collecting the protein from the resultant culture.

In one embodiment of the invention, examples of the protein described above may include erythropoietin (EPO), thrombopoietin (TPO), blood coagulation factor, factor VIII, factor IX, von Willebrand factor (vWF), dystrophin, dopamine synthase, insulin, insulin-like growth factor (IGF), insulin-like growth factor binding protein (IGFBP), antibody, telomerase, granulocyte colony stimulating factor, granulocyte/macrophage colony stimulating factor, immunoglobulin, growth hormone, interleukin 2, interleukin 3, interleukin 4, interleukin 5, interleukin 6, interleukin 7, interleukin 8, interleukin 9, interleukin 10, interleukin 11, interleukin 12, interleukin 15, CD40 ligand, interferon, adenosine deaminase, alpha-1 antitrypsin, ornithine transcarbamylase, purine nucleotide phosphorylase, growth inhibiting factor (GIF), tumor necrosis factor (TNF), leukemia inhibitory factor (LIF), oncostatin M, Flt3 ligand (Flt3L), stroma derived factor (SDF), stem cell growth factor (SCF), fibroblast growth factor (FGF), epidermal growth factor (EGF), vascular endothelial growth factor (VEGF), angiopoietin, nerve growth factor (NGF), bone morphogenetic factor (BMP), activin, transforming growth factor (TGF) and Wnt.

The definitions of terms used herein are as follows.

The term "human artificial chromosome vector" or "HAC vector" as used herein refers to an artificial chromosome produced based on a human chromosome.

The term "human chromosome" as used herein refers to a complex of a natural DNA derived from human cells and a protein. There are normally 46 chromosomes of 23 kinds (24 kinds in males), each of which contains DNA of about 50-300 Mb. The term "fragment of a human chromosome" or "human chromosome fragment" refers to a portion of a chromosome that is capable of stable replication and partition as an independent chromosome, and the size of a fragment may be normally 1 Mb or more, and sometimes 1 Mb or less.

The term "long arm" and "short arm" as used herein with respect to chromosomes refer to the arms on either sides of the centromere of a chromosome, and is referred to as the long arm (q) and short arm (p) according to the length. In addition, the term "distal region of the long arm" or "proximal region of the long arm" as used with respect to human chromosomes means a region at a distal (i.e., the telomere side) or proximal location relative to the centromere on the long arm. Specifically, in the case of human chromosome 21, the distal region of the long arm refers to the telomere side of AL163204 and the proximal region of the long arm refers to the centromere side of AL163203, and in the case of human chromosome 14, the distal region of the long arm refers to the telomere side of AL132642 and the proximal region of the long arm refers to the centromere side of AL157858. In addition, the term "distal region of the short arm" or "proximal region of the short arm" means a region at a distal or proximal location relative to the centromere on the short arm. Specifically, in the case of human chromosome 21, the distal and proximal regions of the short arm are bordered at AL163201, and in the case of human chromosome 14, they are bordered at the ribosomal RNA region.

The terms "site-specific recombination enzyme" and "recognition site for site-specific recombination enzyme" as used herein are the terms used in describing phenomena in which an enzyme recognizes a specific recognition site and causes DNA recombination at the recognition site in a specific manner, and they refer to the enzyme causing site-specific recombination and the site recognized by the enzyme, respectively.

The term "artificial telomere sequence" as used herein refers to an artificially added telomere sequence. According to the invention, an artificial telomere sequence may be added, for example, by telomere truncation.

The term "foreign DNA" as used herein refers to a DNA introduced into a target cell from outside, and means a DNA encoding a gene, of which expression is desired for material production, functional modification or functional analysis, and other functional sequences (for example, promoter sequences), and it may be homogeneous or heterogeneous.

The terms "donor cell" and "recipient cell" as used herein in describing the transfer or introduction of a human artificial chromosome vector refer to a cell (donor cell) that originally retains the vector and a cell (recipient cell) into which the vector is transferred from the donor cell.

BRIEF DESCRIPTION OF THE DRAWINGS

The application contains at least one drawing executed in color. Copies of this patent or patent application publication with color drawing(s) will be provided by the office upon request and payment of the necessary fee.

FIG. 4a shows a human chromosome 21 (arrow) retained in the DT40 cell, and FIG. 4b shows a human chromosome 21 fragment (arrow) from which the long arm has been deleted.

FIG. 7a shows a full-length (entire) human chromosome 21 before telomere truncation and FIG. 7b shows a human chromosome 21 fragment from which the distal region of the long arm has been deleted.

FIG. 15a shows a human chromosome 21 (arrow) devoid of the long arm retained in the DT40 cell, and FIG. 15b shows a human chromosome 21 fragment (arrow) from which the long and short arms have been deleted.

FIG. 19 shows the results of PCR analysis indicating the introduction of a HAC vector derived from human chromosome 21 into the G418 or hygromycin resistant E14 clone.

FIG. 20a shows a chromosome fragment (arrow) devoid of the distal region of the long arm, and FIG. 20b shows a chromosome fragment (arrow) from which the distal region of the short arm has been further deleted.

BEST MODE FOR CARRYING OUT THE INVENTION

Figure 1:
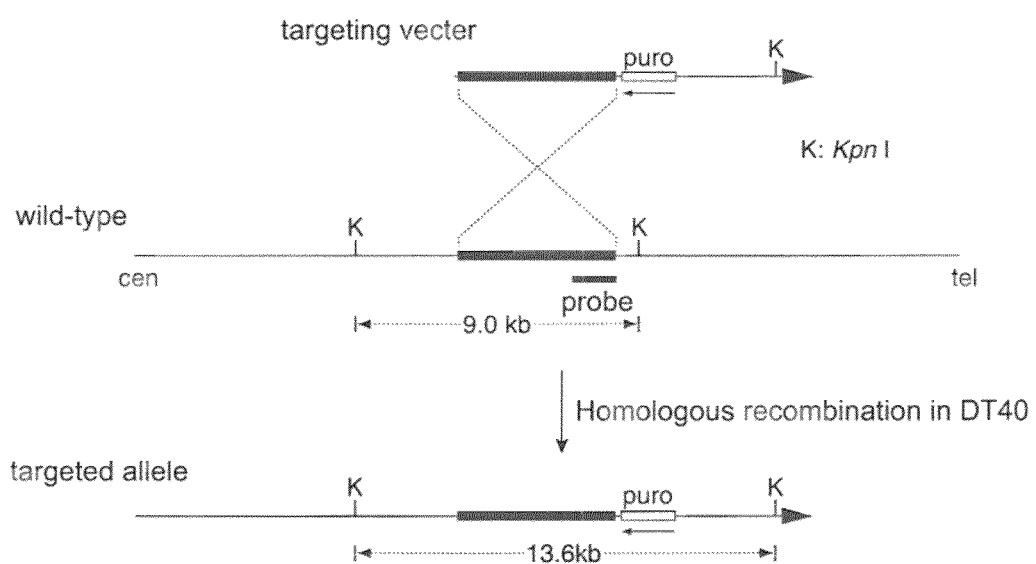
FIG. 1 is a schematic view of the method of deleting the distal region of the long arm of human chromosome 21 by telomere truncation.

The present invention is described in more detail below. The present application claims priority on the JP Patent Application No. 2002-292853 filed on Oct. 4, 2002, the specification and/or drawings thereof are incorporated herein.

The present invention relates to a human artificial chromosome vector (hereinafter, also referred to as "the HAC vector"), and the HAC vector is derived from human chromosome 21 or 14, comprising a fragment of human chromosome 21 or human chromosome 14 from which the distal region of the long arm and/or the distal region of the short arm has been deleted.

For human chromosome 21, nucleotide sequences for the entire long arm and part of the short arm excluding the centromere region have been disclosed in public database (for example, refer to http at site hgp.gsc.riken.go.jp/chr21/index.html (Riken Genomic Sciences Center, Human Genome Research Group)). By utilizing such sequence information, it will be possible to insert artificial telomere sequence or loxP sequence described later in a site-specific manner by homologous recombination. In addition, chromosome 21 of about 48 Mb will be decreased one third to about 16 Mb after deleting the distal region of the long arm, and a HAC vector of about 2 Mb which contains no known genes will be finally constructed after deleting the distal regions of the long and short arms.

In a previous experiment in which human chromosome 21 was transferred into mouse ES cells to form chimeric mice, a fragment of the transferred chromosome was transmitted to the next generation. It is thought that elimination of the region of the transferred chromosome that contained a gene obstructing host cell functions resulted in stabilization (Kazuki et al., J. Hum. Genet., 46: 600, 2001). In the case of human Y-chromosome, on the other hand, the chromosome was unstable in mouse ES cells, but stabilization was achieved by incorporating the alphoid DNA from the mouse chromosome, which is a component of the centromere (Shen et al., Hum. Mol. Genet., 6: 1375, 1997). These suggest that the stability of human chromosome in hybrid cells varies depending on the chromosome and the centromere is involved in stability. Because the previous experiment demonstated that the centromere of human chromosome 21 (about 2 Mb in size: Triowell et al., Hum. Mol. Genet., 2: 1639-1649, 1993; Wang et al., Genome Res. 9: 1059-1073, 1999) functions in mouse cells/individuals, the HAC vector of the present invention which is prepared based on a fragment of human chromosome 21 that contains the centromere region is expected to be stably retained in hybrid cells.

Similarly, nucleotide sequences for a part of human chromosome 14 have been disclosed on public database. Furthermore, it is thought that a reduction in size similar to that for human chromosome 21 is also possible in a HAC vector derived from a spontaneous fragment of human chromosome 14 (SC20; Tomizuka et al., P.N.A.S. 97: 722-727, 2000). For SC20, deficiency in most parts of the distal and proximal regions of the long arm of human chromosome 14 have been reported (Tomizuka et al., P.N.A.S. 97: 722-727, 2000; Kuroiwa et al., Nature Biotech. (USA), Vol. 18, p. 1086-1090, 2000). Specifically, SC20 retains a region ranging from the telomere sequence to AL137229 (GenBank Accession number) of the long arm of human chromosome 14 and a region further on the centromere side ranging from AL121612 (GenBank Accession number) to the telomere side of AL157858 (GenBank Accession number) including 24-26 kb. In addition, the region between AL137229 (GenBank Accession number) and AL121612 (GenBank Accession number) and the region between a point 24-26 kb from AL157858 (GenBank Accession number) on the telomere side and the centromere are deficient. On the other hand, the short arm region of human chromosome 14 is retained. SC20 was retained stably in cell lines including human cells and mice (Shinohara et al., Chromosome Res., 8: 713-725, 2000), and stability was also retained in a modified SC20 into which a loxP site was inserted in the ribosomal RNA region (located in the short arm of human chromosome 14) (Kuroiwa et al., Nature Biotech. (USA), Vol. 18, p. 1086-1090, 2000). Furthermore, a HAC, in which an unstable chromosome region of about 10 Mb derived from a fragment of human chromosome 22 was translocated into the loxP site of the modified SC20, was stably retained in mouse ES cells and mouse individuals. A problem with the SC20 is that it contains a plurality of genes from the 14q32 region of chromosome 14, but by decreasing the SC20 in size according to the method described herein it can be retained stably in various cell types and a HAC vector containing no unnecessary genes can be obtained.

Production of the HAC vector of the invention, insertion of foreign DNA into the vector, and uses of the HAC vector are described below.

1. Production of a Human Artificial Chromosome (HAC) Vector

As described above, the HAC vector of the invention is produced based on human chromosome 21 or human chromosome 14. Production of the HAC vector of the invention includes the following steps (a)-(c):

(a) obtaining cells that retain human chromosome 21 or human chromosome 14;

(b) deleting a distal region of the long arm and/or a distal region of the short arm of the human chromosome 21 or human chromosome 14; and (c) inserting a recognition site for a site-specific recombination enzyme into a proximal region of the long arm and/or a proximal region of the short arm of the human chromosome 21 or human chromosome 14.

Here, the steps (b) and (c) may be in any order.

Step (a): Production of Cells Retaining Human Chromosomes

For the production of the HAC vector of the invention, cells that retain human chromosomes (for example, human chromosome 21 or human chromosome 14) are prepared. Preferably, such cells are those that retain only human chromosome 21 or human chromosome 14 and have high homologous recombination efficiency for later manipulation. Therefore, cells which satisfy these conditions are first produced.

For example, cells retaining a human chromosome can be produced by screening a known mouse A9 hybrid cell library retaining a human single chromosome for clones retaining human chromosome 21 or human chromosome 14, and transferring the chromosome into cells with high homologous recombination efficiency. The mouse A9 hybrid cell library contains a human single chromosome labeled with a drug resistant gene, and has been described, for example, in WO00/10383, Tanabe, H. et al. (Chromosome Res., 8: 319-334, 2000). In addition, the mouse A9 hybrid cells retaining human chromosome 21 and human chromosome 14 have been registered with the Japanese Collection of Research Bioresources (JCRB) under the registry number JCRB2221 (cell name: A9 (Hygro21)) and JCRB2214 (cell name: A9 (Hygro14)), respectively, and detailed information and culture conditions are available.

The human chromosome retained in the mouse A9 hybrid cell obtained as above is transferred into cells with high homologous recombination efficiency. "Cells with high homologous recombination efficiency" refer to those which show a high homologous recombination frequency when subjected to homologous recombination, and examples of such cells include a chicken DT40 cell (Dieken et al., Nature Genetics, 12: 174-182, 1996) and mouse ES cell (Shinichi Aizawa, Biomanual Series 8, Gene Targeting, Yodo-sha Co., Ltd., 1995). Preferably, the chicken DT40 cell is used for the method of the present invention in light of ease of handling.

The transfer of chromosomes can be performed by methods for chromosome transfer known in the art. For example, methods for introducing only one desired chromosome include the microcell method described in Koi et al. (Koi et al., Jpn. J. Cancer Res., 80: 413-418, 1973). This method involves isolating microcells induced by a chemical that inhibits spindle formation in a certain cell, and fusing these microcells with recipient cells to introduce a few chromosomes. For specific procedures for transferring human chromosomes using this microcell method, see for example WO97/07671 and WO00/10383. Thus, cells that retain human chromosome 21 or human chromosome 14 can be produced.

Alternatively, in another aspect of the invention, cells may be used that retain a spontaneously fragmented chromosome, for example a fragment of human chromosome 14 (SC20), instead of entire human chromosome 21 or human chromosome 14. The chicken DT-40 cell (SC20) that retains the SC20 chromosome fragment has been deposited with the National Institute of Advanced Industrial Science and Technology, the International Patent Organism Depositary (Chuo 6, Higashi 1-1-1, Tsukuba-shi, Ibaraki, Japan), as of May 9, 2001 with the accession number of FERM BP-7583.

Step (b): Deletion of the Distal Region of the Long Arm and/or the Distal Region of the Short Arm of Human Chromosomes For the production of a HAC vector from a cell retaining a human chromosome, the distal region of the long arm and/or the distal region of the short arm of the human chromosome is deleted. Deletion of a chromosome can be performed by methods known in the art, such as, preferably, by substitution with an artificial telomere sequence (telomere truncation) described in WO00/10383. A specific procedure for deleting the distal region of the long arm and/or the distal region of the short arm involves, for example, constructing a targeting vector carrying an artificial telomere sequence in a cell retaining a human chromosome, obtaining a clone into which the artificial telomere sequence has been inserted at a desired site on the chromosome by homologous recombination, and obtaining a deletion mutant by telomere truncation (see, for example, Itzhaki et al., Nature Genet., 2:283-287, 1992; Brown et al., P.N.A.S., 93: 7125, 1996). The desired site of the chromosome refers to a cutting site of the distal region of the long arm or the distal region of the short arm to be deleted, and an artificial telomere sequence is inserted at this site by homologous recombination, and the distal region of the long arm or the short arm is substituted with the artificial telomere sequence (telomere truncation). The desired site can be set as appropriate by the design of the target sequence when constructing the targeting vector, and when deleting the distal region of the long arm, for example, the target sequence is designed based on a nucleotide sequence within the 21q11 region on human chromosome 21, preferably the nucleotide sequence at AL163204 (GenBank Accession number), such that telomere truncation will occur on the telomere side of the target sequence, thus cutting off the distal region of the long arm at the site used to design the target sequence (see, for example, Kuroiwa et al., Nucleic Acid Research, 26: 3447, 1998). In addition, when deleting the distal region of the short arm, the target sequence can be designed based on a nucleotide sequence within the 21p region on human chromosome 21, preferably the nucleotide sequence at AL163201 (GenBank Accession number). Those skilled in the art can design the target sequence as appropriate to produce a desired HAC vector without limitation to the region described above.

In addition, when, for example, the sequence of the long arm of human chromosome 14 is deleted at a site nearer to the centromere than the site in SC20, the target sequence can be designed based on the nucleotide sequence within the AL157858 region such that telomere truncation will occur on the telomere side of the target sequence, thus cutting off the distal region of the long arm at the site used to design the target sequence. In addition, when, for example, deleting the distal region of the short arm, the target sequence may be designed based on a nucleotide sequence within the 14p region of human chromosome 14, preferably a nucleotide sequence within the 14p12 region, more preferably the nucleotide sequence of OR4H12, OR4Q4, RNR2, OR4L1, RNU6C, FDPSL3, K12T, C14orf57, OR6S1, M195, OR4K14, MGC27165, LCH, OR10G3, OR4K3, OR4E2, H1RNA, ATP5C2, OR11H6 or OR4M1 (online genome database (http://www at site ncbi.nlm.nih.gov/mapview/ maps.cgi?ORG=hum&CHR=14&BEG=0.00&ENI) provided by the US National Center for Biotechnology Information (NCBI)). Those skilled in the art can design the target sequence as appropriate so as to produce a desired HAC vector without limitation to the region described above.

In addition, when, for example, the sequence of the long arm of an intact human chromosome 14 is to be deleted, the target sequence can be designed based on a nucleotide sequence within the 14q region, preferably the nucleotide sequence at AL512310 (GenBank Accession number) such that telomere truncation will occur on the telomere side of the target sequence, thus cutting off the distal region of the long arm at the site used to design the target sequence. In addition, when, for example, deleting the distal region of the short arm, the target sequence may be designed based on a nucleotide sequence within the 14p region of human chromosome 14, preferably a nucleotide sequence within the 14p12 region, more preferably the nucleotide sequence of OR4H12, OR4Q4, RNR2, OR4L1, RNU6C, FDPSL3, K12T, C14orf57, OR6S1, M195, OR4K14, MGC27165, LCH, OR10G3, OR4K3, OR4E2, H1RNA, ATP5C2, OR11H6 or OR4M1 (online genome database (http://www, at site ncbi.nlm.nih.gov/mapview/ maps.cgi?ORG=hum&CHR=14&BEG=0.00&ENI) provided by the US National Center for Biotechnology Information (NCBI)). Those skilled in the art can design the target sequence as appropriate so as to produce a desired HAC vector without limitation to the region described above.

As described above, a human chromosome fragment from which the distal region of the long arm and/or the distal region of the short arm was deleted has been formed and cells retaining these chromosome fragments provided. By reducing the size of chromosomes as described above, stability in cells can be achieved. In addition, a region of the chromosome may be deleted that is estimated to have adverse effects on the function/proliferation of the cells retaining the HAC vector and the cells described later into which the HAC vector will be introduced.

Step (c): Insertion of Recognition Site for Site-Specific Recombination Enzyme

For the production of the HAC vector of the invention, a recognition site for a site-specific recombination enzyme is inserted into human chromosome 21 or human chromosome 14. Step (c) may be performed before or after step (b), and the order is not specifically limited. In human chromosome 21 or human chromosome 14, a recognition site for site-specific recombination enzyme may be inserted after having deleted the distal region of the long arm and/or the distal region of the short arm, or alternatively, the distal region of the long arm and/or the distal region of the short arm can be deleted after inserting a recognition site for site-specific recombination enzyme.

In the art, a certain enzyme is known to recognize a particular recognition site and induce DNA recombination specifically at the recognition site, and the present invention utilizes a system of such an enzyme and recognition site. Examples of such systems include the Cre/loxP system (see, for example, Sauer, B. et al., P.N.A.S., 85: 5166-5170, 1988). Cre is a 38 KD protein derived from bacteriophage P1, and belongs to the family of recombinase Int (integrase). This enzyme recognizes the recognition site loxP sequence of about 34 bp, and induces DNA recombination specifically at this site. In addition, a deletion or translocation of the DNA between two loxP sequences is known to occur depending on the orientation of this loxP sequence. Other systems for the specific recognition sequence and specific recombination include the recombinase FLP derived from budding yeast (Broach et al., Cell, 21:501-508, 1980), and the integrase derived from phage phiC31 (Thorpe et al., P.N.A.S., 95: 5505-5510, 1998), and these enzymes could induce DNA recombination in mammalian cells (Koch et al., Gene, 249: 135-144, 2000; Thyagarajan et al., Mol. Cell. Biol., 21: 3926-3934, 2000).

Methods known in the art for gene recombination, such as the homologous recombination method, can be used to insert the recognition site for the site-specific recombination enzyme into a proximal region of the long arm and/or a proximal region of the short arm of a human chromosome. Those skilled in the art can, as appropriate, design the position for the insertion of the recognition site for the site-specific recombination enzyme by considering the location of unessential genes. For example, a recognition site for a site-specific recombination enzyme is inserted at any position in the proximal region of the long arm and/or the short arm of human chromosome 21 or human chromosome 14. The positions for insertion include, for example, AL163203 in the proximal region of the long arm of human chromosome 21, and a more proximal region than AL157858 (GenBank Accession number) in the proximal region of the long arm of human chromosome 14, more preferably a more proximal region than the deletion site of AL512310 (GenBank Accession number) in the proximal region of the long arm or a more proximal region than the deletion site within the 14p12 region of the proximal region of the short arm of human chromosome 14.

A reporter gene is subsequently introduced according to the method described later for introducing foreign DNA, and can be checked for its expression to confirm the propriety of the position of the recognition site inserted onto the human chromosome.

One or more recognition sites of one of the types described above, or a plurality of recognition sites from different systems may be inserted. As described later, because the foreign DNA can be introduced in a site-specific manner and the position for the introduction of foreign DNA can be determined by placing the recognition site into a desired site since the HAC vector possesses a recognition site for a site-specific recombination enzyme, the position for introduction of foreign DNA will be consistent and unaffected by position effect. In addition, the procedure for introduction of foreign DNA will be simple and easy. Moreover, a plurality of foreign DNA can be inserted sequentially by inserting a plurality of recognition sites from different systems.

In addition to the recognition site for site-specific recombination enzyme, a sequence or element which is generally inserted upon constructing vectors (such as promoters and drug resistant genes) may be inserted into the HAC vector produced as above by modification of human chromosomes. Such a sequence or element can be inserted into a desired site of the HAC vector using the homologous recombination method as described above.

Furthermore, by subculturing the cells retaining the HAC vector (human chromosome 21 or human chromosome 14) prepared as above for a long period in culture medium not containing any selection drug and examining successively the retention rate of the HAC vector by the FISH method, the inventors have confirmed that the HAC vector can be retained stably in host cells (for example, DT40 cells and CHO cells).

2. Introduction of Foreign DNA into the HAC Vector (Step (d))

In the production of the HAC vector described above, the step (d) of inserting foreign DNA in the presence of a site-specific recombination enzyme can be implemented to introduce a foreign DNA into the HAC vector. Step (d) should follow step (c) above, but may precede or follow step (b). Therefore, it should be noted that the order of steps (b)-(d) is not limited to that described herein.

Foreign DNA refers to the DNA introduced into a cell from outside that encodes a gene and other functional sequences. In embodiments of the invention, the foreign DNA to be introduced may be any DNA that encodes either a gene the expression of which is desired for material production, functional modification and functional analysis or other functional sequences. The other functional sequences refer to sequences which function so as to express genes, such as promoters, enhancers and signal sequences.

Foreign DNA is introduced using the system of the site-specific recombination enzyme. For example, a targeting vector retaining the loxP sequence, which is a recognition site of the Cre enzyme, and foreign DNA is constructed. Subsequently, by expressing the Cre enzyme in cells retaining the HAC vector (human chromosome 21 or human chromosome 14), the foreign DNA can be inserted onto the HAC vector by site-specific recombination of the region flanked by the loxP sequence and an artificial telomere sequence with the targeting vector above (Kuroiwa et al., Nature Biotech., 18: 1086, 2000).

Circular DNA retaining a recognition site (loxP sequence) for a site-specific recombination enzyme can be inserted in the HAC vector. Thus, it is possible to insert cloned DNA from existing vectors, such as plasmids, BAC and PAC used in *E. coli* and cyclic YAC used in yeast. In addition, because the HAC vector is based on human chromosomes, the size of foreign DNA to be introduced may be increased to 100 kb order, allowing for introduction of genomic DNA containing the gene expression regulatory region as well as the cDNA incorporated into plasmid vectors, which has been used in conventional expression experiments.

For example, in the HAC vector containing foreign DNA produced by inserting foreign DNA into the HAC vector, its stable structure may be altered as a result of insertion, or the entire size of the HAC vector containing the foreign DNA may increase disadvantageously, so the size of the foreign DNA to be introduced (inserted) is generally about 10 Mb to about 1 kb, preferably about 3 Mb to about 2 kb, more preferably about 1 Mb to about 3 kb.

Because the conventional gene introduction method using a vector for forced expression of cDNA suffers adverse effects from overexpression, such as cytotoxicity and growth inhibition, cell clones that allow for constant expression of introduced genes have not been obtained in many cases. Desirably, the gene expression induction system using, for example tetracycline, is employed to overcome the problem and control the expression artificially while maintaining the physiological expression pattern. The HAC vector characterized in that the insert that can be introduced is large in size and a constant copy number is maintained is suitable for such a purpose.

Tissue-specific/physiological gene expression is controled in the processes of transcription from the genome region encoding the gene, splicing of the transcription product, extranuclear transport and translation. A gene has a plurality of promoters, and the difference in the transcription initiation site and variations in splicing are known to result in tissue-specific isoforms. Cloned cDNA is only one of the transcriptional variant products derived from a gene. Desirably, the gene region containing the control sequence is introduced as genomic DNA to reproduce physiological gene expression. Use of the HAC vector answers such a purpose.

Because transmission to the next generation was confirmed when a chimera was produced from mouse ES cells retaining a human chromosome 21 fragment, it is thought that the centromere of human chromosome 21 is replicated, partitioned and retained in mouse cells and in mice (Kazuki et al., J. Hum. Genet., 46: 600, 2001). Therefore it is very likely that the HAC vector is also retained stably in mice.

In the human genome project, genomic DNA was isolated as BAC clones, then the nucleotide sequences were determined. Therefore, the nucleotide sequences have been registered in the database (for example, GenBank) in terms of BAC as well. One of the techniques for analyzing gene function is the generation of transgenic mice. By inserting BAC into the HAC vector as platform, it will be possible to analyze gene expression under constant conditions without being affected by position effect. Because many BAC vectors contain the loxP sequence, BAC of known nucleotide sequence can be inserted easily into the HAC vector as a cassette by using a system for negative selection of insertion into the HAC vector.

There are other methods for introducing foreign DNA into the HAC vector and other advantages of introduction, and the following are some examples.

(1) Introduction of Chromosome Fragments by Reciprocal Translocation

Site-specific recombination between loxP sequences by the Cre enzyme involves insertion reaction in the case of linear chromosome and circular insert (foreign DNA), but reciprocal translocation reaction occurs between linear chromosomes. By using this, a chromosome fragment of the Mb order or higher that cannot be cloned into circular inserts can be introduced into the HAC vector (Kuroiwa et al., Gene Ther. 9: 708, 2002).

(2) Selection Method for Recombinant Having Insert

In the method described in examples of the present invention, the insertion of foreign DNA into the HAC vector uses the positive selection based on reconstitution of a drug resistant gene as an indicator (see WO00/10383 for positive selection of recombinants). Alternatively, negative selection such as by the thymidine kinase/ganciclovir system can be used to obtain DNA with an insert (DNA into which foreign DNA has been inserted). In this case only the loxP sequence should be included in the circular DNA to be inserted. Because the BAC library used in the genome project contains the loxP sequence, a genome clone of known sequence can be easily inserted into the HAC vector if such a system for negative selection can be established.

(3) Insertion of Multiple Inserts

The loxP sequence which is preferably used in the present invention is a wild-type sequence derived from P1 phage, and the insertion reaction of the circular insert into the loxP sequence on the HAC vector by the Cre enzyme is reversible. In an example of the present invention, the Cre enzyme was expressed transiently and site-specific recombinants were selected for acquisition of drug resistance to obtain constitutional DNA with insert. Once a circular insert is inserted, two loxP sequences remain on the HAC vector. Therefore, if the Cre enzyme is expressed again, reverse reaction (excision of circular insert) may be occurred, making it difficult to make additional modifications to the HAC vector, such as inserting a secondary insert. On the other hand, the direction and specificity of reaction can be limited depending on the combination of variant loxP sequences with nucleotide substitution (Hoess et al., Nucleic Acids Res., 14: 1986; Araki et al., Nucleic Acids Res., 25: 868, 1997; Lee et al., Gene, 216: 55, 1998). By using these variant loxP sequences, it will be possible to construct a system to insert a plurality of circular inserts sequentially without inducing the reverse reaction described above.

(4) Copy Number-Dependent Expression Control

A study (Sharpe et al., Proc Natl Acad Sci USA, 90:11262, 1993) which analyzed the relationship between the copy number of genes inserted at random into host chromosomes using transgenic mice having α-globin gene and the expression level of mRNA showed no correlation between the expression level and the copy number of introduced genes. This is probably due to the phenomenon called position effect in which the expression level of introduced genes varies significantly depending on the transgenic animal line used and is not in proportion to the copy number of the introduced gene, and this phenomena occurs frequently in gene transfer in transgenic animals. In addition, foreign DNA was inserted at the predetermined loxP site introduced onto the host chromosome to exclude the position effect of the introduced gene, and the target DNA unit was introduced from the plasmid vector to a transgenic mouse by Cre-loxP recombination reaction (Garrick et al., Nature Genet., 18: 56, 1998); however, the copy number-dependent expression control was not achieved.

Meanwhile, although the copy number-dependent expression of tyrosinase in the introduced genome region was observed in transgenic mice generated using the YAC into which the tyrosinase genome region was introduced (Schedl et al., Nature, 362: 258-261, 1993), it is thought position effect was unlikely since a genome containing a physiological expression control region was used unlike the present invention in which only artificial gene expression units not containing the physiological control region are multiplied. In addition, various episome vectors were independent of host chromosomes and the location of insertion of foreign DNA was fixed, but strict control of the copy number of vectors was not attained (Morlino et al., ppl Environ Microbiol., 65: 4808-4013, 1999; Cooper et al., Proc Natl Acad Sci USA., 94: 6450-6455, 1997).

In the present invention, as shown in example 9, by arranging multicopies of the expression unit of the target gene (EPO) in parallel and introducing them at a predetermined position (loxP site) on the HAC vector, copy number-dependent expression control can be attained without causing variation in the host chromosome.

Therefore, according to the method of the present invention, it will be possible both to introduce multicopies of the target gene into a desired cell as foreign DNA and express the target gene in the cell in a copy number-dependent manner and to achieve, without position effect, previously difficult copy number-dependent expression of the target gene in the transgenic animal generated using the cell.

3. Transfer of the HAC Vector into Cells

The HAC vector or the HAC vector containing foreign DNA can be transferred from the cell retaining these vectors to other cells. The cells to which these vectors are transferred include, but not limited to, animal cells (mammalian cells). According to the present invention, preferably the Chinese hamster ovary (CHO) cell, which is known to allow for intact transfer of human chromosomes, is used (see WO00/10383). The CHO cell is known to form microcells efficiently (see, for example, Koi et al., SCIENCE 260:361, 1993), and the HAC vector can be further transferred from the CHO cell to other cells (cells other than the CHO cell). In addition, according to the present invention, the HAC vector can be transferred to pluripotent cells. The term "pluripotent cell" means a cell capable of differentiation into particular cells or tissues through given procedures. Examples of pluripotent cells include cells that are capable, through procedures such as infusion into host embryos and formation of collective embryos, of differentiating into two or more types of cells or tissues in chimeric animals, such as embryonic stem cells (ES cells), embryonic germ cells (EG cells) and embryonic cancer cells (EC cells). Also included are cells capable of differentiating into bone cells, chondrocytes or adipose cells by culturing the cells in inducer medium supplemented with, for example growth factors (ex., transforming growth factor; TGF), more specifically somatic stem cells (ex., mesenchymal stem cells).

The term "embryonic stem cell," or ES cell, as used herein refers to a cultured cell derived from an early phase embryo characterized by the ability to multiply while maintaining undifferentiated nature (totipotency). Embryonic stem cells are cell lines established by culturing the cells in the internal cell mass, which is undifferentiated stem cells present inside the blastocyst of the initial embryo of animals, so as to keep multiplying while maintaining an undifferentiated state. The term "embryonic germ cell," or EG cell, means a cultured cell derived from a primordial germ cell characterized by ability almost equivalent to that of the embryonic stem cell above. Embryonic germ cells are cell lines established by culturing primordial germ cells obtained from embryos several days to several weeks after fertilization, for example about 8.5 days after fertilization for mice, so as to keep multiplying while maintaining an undifferentiated state.

In addition, the cells used as raw material for gene and cell therapy and tissue regeneration therapy for humans should be normal cells but not immortalized cells in light of safety to avoid canceration. While there are a number of cases of transfer of chromosomes to immortalized cells and cancerous cells in humans and other animals, there is no reported case of transfer of chromosomes to normal somatic cells as far as the on-line literature database PubMed (www at site ncbi.nlm.nih.gov/entrez/query.fcgi?db=PubMed) of the US National Center for Biotechnology Information (NCBI) was searched for the keywords: chromosome, transfer, human, normal, primary or somatic and cell, excepting the report of transfer to bovine fetal normal fibroblast (Kuroiwa et al., Nature Biotech., 20: 889, 2002). Consequently, a general recognition has been that transferring chromosomes to human normal somatic cells is difficult.

Examples 13 and 14 of the present invention showed for the first time the possibility of transferring a HAC vector derived from human chromosome 14 fragment or human chromosome 21 to a human normal fibroblast. In addition, according to the method of the present invention, the transfer of a HAC vector derived from human chromosome 14 fragment or human chromosome 21 to a human normal somatic cell other than fibroblasts is possible. Furthermore, any HAC vector derived from human chromosomes that is produced according to the method of the present invention can be transferred to human normal somatic cells, without limitation to human chromosome 14 or human chromosome 21.

Transfer of the HAC vector to cells can be performed using the microcell method. The microcell method can be performed as described above in "1. Production of human artificial chromosome (HAC) vector."

In addition, for transfer of the HAC vector to cells, the human chromosome (HAC vector) can be transferred from the initial cell retaining the human chromosome to other cells in any of the stages; before, during or after the step of modifying the human chromosome.

4. Uses of HAC Vector

The present invention is intended to provide a vector as a basic tool and the technology to use it, and its effect on wide range fields from scientific study to industry is expected. The characteristics of the HAC vector of the invention that (1) it is not inserted into the host chromosome and maintained independently (no fear of variation or canceration of host gene), (2) a constant copy number is maintained for a long period (no fear of overexpression or loss of expression), and (3) the DNA to be introduced is not limited in length (genes containing the DNA element that ensures normal expression control and multiple genes can be introduced simultaneously) should enable a number of things that have been difficult to achieve with conventional vectors. Examples of uses of the HAC vector include, but not limited to, (1) a vector for gene function analysis in cultured animal cells, (2) a vector for gene therapy for human illnesses, (3) a vector for gene transfer to human organ stem cells and embryonic stem cells (ES cells), and (4) a vector for the production of transgenic animals (for example, production of human disease model animals and humanization of particular genes combined with KO animals). The following will be described as examples of use of the HAC vector: (1) introduction of foreign DNA into recipient cells, (2) production of cells expressing foreign DNA, (3) production of protein, (4) vector for analysis of gene function, (5) vector for gene transfer into stem cells, (6) vector for the production of culture feeder, and (7) vector for the treatment of human disease.

(1) Introduction of Foreign DNA into Recipient Cells

Because foreign DNA can be introduced into the HAC vector in cells and the HAC vector with inserted foreign DNA can be transferred to other cells, foreign DNA can be introduced into a desired recipient cell. Introduction of foreign DNA into a recipient cell includes, for example, the following steps:

(a) obtaining donor cells that retain human chromosome 21 or human chromosome 14;

(b) deleting a distal region of the long arm and/or a distal region of the short arm of the human chromosome 21 or human chromosome 14;

(c) inserting a recognition site for a site-specific recombination enzyme into a proximal region of the long arm and/or a proximal region of the short arm of the human chromosome 21 or human chromosome 14;

(d) inserting foreign DNA into the human chromosome 21 or human chromosome 14 in the presence of a site-specific recombination enzyme;

(e) preparing microcells from the donor cells that retain the human chromosome 21 or human chromosome 14;

(f) fusing the microcells and recipient cells; and (g) confirming the introduction of the foreign DNA into the fused recipient cells.

Procedures in steps (a)-(d) can be performed as described above, with no limit to their order.

In steps (e) and (f), the chromosome fragment is transferred from the donor cell retaining the human chromosome to the recipient cell using the microcell method. The human chromosome to be transferred may be any of those before, during and after the modification of the chromosome in steps (b)-(d). Therefore, in step (d), for example, the chromosome may be transferred from the donor cell retaining the human chromosome to the recipient cell using the microcell method before foreign DNA is inserted into the human chromosome. Subsequently, the insertion procedure for foreign DNA in step (d) may be performed in the recipient cell to allow the recipient cell to retain the human chromosome into which the foreign DNA has been inserted. These procedures may be in other order, and the order of steps (d)-(f) is not limited to that described above.

The microcell method can be performed as described above in "1. Production of human artificial chromosome (HAC) vector." The recipient cells used here include, but not limited to, animal cells, and preferably mammalian cells (for example, mouse cells, human cells). In addition, as described above, pluripotent cells, for example, embryonic stem cells (ES cell), and mesenchymal stem cells and tissue stem/precursor cells may also be used as recipient cells.

Step (g) is for confirming whether foreign DNA has been introduced (transferred) into the recipient cell or not. This confirmation can be done by methods known in the art, such as the southern blot analysis which uses a probe corresponding to the restriction enzyme site of the foreign DNA.

The use of the HAC vector will allow for introduction of large-size foreign DNA into cells and stable retention in the cells.

(2) Production of Cells Expressing Foreign DNA.

Because as described above foreign DNA can be introduced into the HAC vector in cells and the HAC vector with inserted foreign DNA can be transferred to other cells, cells expressing foreign DNA can be produced. Production of cells expressing foreign DNA includes, for example, the following steps:

(a) obtaining donor cells that retain human chromosome 21 or human chromosome 14;

(b) deleting a distal region of the long arm and/or a distal region of the short arm of the human chromosome 21 or human chromosome 14;

(c) inserting a recognition site for a site-specific recombination enzyme into a proximal region of the long arm and/or a proximal region of the short arm of the human chromosome 21 or human chromosome 14;

(d) inserting foreign DNA into the human chromosome 21 or human chromosome 14 in the presence of a site-specific recombination enzyme;

(e) preparing microcells from the donor cells that retain the human chromosome 21 or human chromosome 14;

(f) fusing the microcells and recipient cells; and (g) selecting cells expressing the foreign DNA among the fused recipient cells.

Procedures in steps (a)-(f) can be performed as described above, with no limit to their order.

Step (g) is for confirming whether foreign DNA is expressed in the recipient cell and selecting cells expressing the foreign DNA. The confirmation of expression of foreign DNA can be done by methods known in the art, such as the northern blot method which uses a probe corresponding to the foreign DNA.

The use of the HAC vector will allow for production of cells expressing large-size foreign DNA.

(3) Production of Proteins

Because as described above foreign DNA can be introduced into cells and cells expressing foreign DNA can be produced by using the HAC vector, a protein encoded by the foreign DNA can be produced. Production of a protein includes, for example, the following steps:

(a) obtaining donor cells that retain human chromosome 21 or human chromosome 14;

(b) deleting a distal region of the long arm and/or a distal region of the short arm of the human chromosome 21 or human chromosome 14;

(c) inserting a recognition site for a site-specific recombination enzyme into a proximal region of the long arm and/or a proximal region of the short arm of the human chromosome 21 or human chromosome 14;

(d) inserting foreign DNA encoding a protein into the human chromosome 21 or human chromosome 14 under the expression of a site-specific recombination enzyme;

(e) preparing microcells from the donor cells that retain the human chromosome 21 or human chromosome 14;

(f) fusing the microcells and recipient cells;

(g) incubating the fused recipient cells in culture media; and (h) collecting the protein from the resultant culture.

Procedures in steps (a)-(f) can be performed as described above, with no limit to their order.

Step (g) is for incubating the recipient cells fused in step (f) in culture media. Culture medium for incubating recipient cells may be any natural or synthetic medium containing a carbon source, nitrogen source and minerals that allows for efficient incubation of the recipient cell, and those with skill in the art can select appropriate culture medium and, as required, make appropriate modifications to the medium. The aerobic condition, temperature, pH and incubation period for shake culture or aeration spinner culture are set as appropriate.

After incubation, the protein is collected from the resultant culture as described in step (h). The term "culture" means any of cultured cells or disrupted cells and culture supernatant. After incubation, conventional protein purification methods can be used to collect the protein from the culture. For example, when the protein is produced in cells, it is extracted using conventional methods such as ultrasonication, grinding and pressure crushing. A protease inhibitor is added if necessary. When the protein is produced in the supernatant, the culture broth itself can be used. This solution is filtrated, centrifuged to remove solid matter, and treated with protamine, as required, to remove nucleic acid.

Subsequently ammonium sulfate, alcohol, and acetone can be added to the solution to fractionate it, and the precipitate is collected, giving crude protein solution. The protein solution is subjected to various chromotagraphic and electrophoretic analyses to obtain purified enzyme. For example, an appropriate method is selected from such fractionation methods as gel filtration using Sephadex, ultragel or biogel, ion exchange chromatography, electrophoresis using, for example polyacrylamide gel, affinity chromatography and reverse phase chromatography, or combinations of these, to obtain the purified target protein. These incubation and purification methods are provided for illustrative purposes only and are not intended to limit the invention.

The target protein of the invention may be any desired protein, including, for example erythropoietin (EPO), thrombopoietin (TPO), blood coagulation factor, von Willebrand factor (vWF), dystrophin, dopamine synthase, insulin, insulin-like growth factor (IGF), insulin-like growth factor binding protein (IGFBP), antibody, telomerase, granulocyte colony stimulating factor, granulocyte/macrophage colony stimulating factor, immunoglobulin, growth hormone, interleukin 2, interleukin 3, interleukin 4, interleukin 5, interleukin 6, interleukin 7, interleukin 8, interleukin 9, interleukin 10, interleukin 11, interleukin 12, interleukin 15, CD40 ligand, interferon, adenosine deaminase, alpha-1 antitrypsin, ornithine transcarbamylase, purine nucleotide phosphorylase, growth inhibiting factor (GIF), tumor necrosis factor (TNF), leukemia inhibitory factor (LIF), oncostatin M, Flt3 ligand (Flt3L), stroma derived factor (SDF), stem cell growth factor (SCF), fibroblast growth factor (FGF), epidermal growth factor (EGF), vascular endothelial growth factor (VEGF), angiopoietin, nerve growth factor (NGF), bone morphogenetic factor (BMP), activin, transforming growth factor (TGF) and Wnt. Sequence information of the genes (i.e., foreign DNA) encoding these target proteins can be obtained using, for example, public gene database.

(4) Vector for Analysis of Gene Function

The foreign DNA inserted into the HAC vector is expressed intracellularly in a copy number-dependent and stable manner, so the HAC vector can be used to analyze gene function.

RNA interference, a method of controlling the expression of a target gene by expressing double-stranded RNA (dsRNA) comprising a complementary sequence in a portion of the nucleotide sequence encoding the target gene, is known (see, for example, Elbashir et al., Nature, 411: 494, 2001; McCaffrey et al., Nature, 418: 38, 2002, for short interfering RNA (siRNA). See also Shinagawa, T. et al., Genes & Development, 17: 1340-1345, 2003). By introducing the DNA encoding dsRNA along with the gene expression induction system into the HAC vector, conditional control of the function of the target gene will be possible. By using a genome region instead of the gene expression induction system, control of function at tissue-specific/physiological site will be possible.

A method is available which is used for analyzing the effect of a target molecule using its dose dependence as an indicator. In this method, by introducing into the HAC vector the expression unit of a gene encoding a target molecule according to the invention by varying the copy number then transferring to cells (including tissue and individuals), it will be possible to perform dose-dependent analysis based on copy number-dependent expression control in the cells. In addition, the use of an expression induction system or a genomic region for the control of gene expression will allow for conditional or tissue-specific/physiological functional analysis.

(5) Vector for Gene Transfer into Stem Cells

As shown in examples 20 and 21, the HAC vector produced according to the method of the present invention can be used as a vector for gene transfer to embryonic stem (ES) cells or mesenchymal stem cells (MSC). The HAC vector described above can remain stable in ES cells or MSC for a long time.

As shown in examples 20 and 21, the HAC vector remains stable in the tissue cell derived from MSC retaining the HAC vector produced according to the method of the present invention. Because when a chimeric mouse was generated from mouse ES cells retaining a fragment of human chromosome 21, the chromosome fragment was transmitted to the following generation and the cells that differentiated from the ES cells in tissue retained the fragment of human chromosome 21 (Kazuki et al., J. Hum. Genet., 46: 600, 2000), the HAC vector produced according to the method of the invention may also be retained stably in the tissue cells that differentiate from ES cells to which the HAC vector is transferred.

Stem cells from various tissues and pluripotent cells from bone marrow have been identified in recent years (Yokota et al., Jikken Igaku (extra number), Vol. 19 No. 15, 2001, Yodo-sha; Okano et al., Jikken Igaku (extra number), Vol. 21 No. 8, 2003, Yodo-sha; Li et al., Nature Med., online: 31 Aug. 2003, doi: 10.1038/nm925). The HAC vector produced according to the method of the present invention can be used as a vector for gene transfer to tissue stem/precursor cells, for example pluripotent stem/precursor cells derived from bone marrow, blood, nerve, muscle, liver, pancreas, skin, and inner ear.

Furthermore, in light of clinical application of ES cells, MSC and tissue stem/precursor cells in humans, it will be necessary to amplify an amount of cells that is required for treatment and provide them in a desired differentiation state. Conventionally, it has not been easy to multiply only stem cells in large quantities while maintaining pluripotency (Hino et al., Jikken Igaku, Vol. 19 Vol. 15 (extra number):10, 2001, Yodo-sha). For example, when hematopoietic stem cells and nerve stem cells were collected from living tissue and incubated, not only stem cells but also precursor cells and mature cells which differentiated from the stem cells multiplied at the same time, making them unfavorable for clinical use (Okano, S., Jikken Igaku, Vol. 19 No. 15 (extra number): 80-90, 2001, Yodo-sha).

In the present invention, by producing the HAC vector incorporating DNA encoding a factor involved in maintaining pluripotency, for example tanscription factors such as active Stat3, Oct-3/4 and Nanog in the case of mouse ES cells (Niwa et al., Genes Dev., 12: 2048, 1998; Matsuda et al., EMBO J., 18: 4261, 1999; Niwa et al., Nature Genet., 24: 373, 2000; Mitsui et al., Cell, 113:631, 2003; Chambers et al., Cell, 113: 643, 2003) and transferring it to stem cells, it will be possible to multiply stem cells while maintaining pluripotency without mutating host chromosomes.

In addition, in controlling stem cell differentiation, the control of the expression level of the molecule involved is an important element. For example, in the control of differentiation in mouse ES cells by Oct-3/4 described above, an undifferentiated state was maintained when its physiological expression level was maintained at 100%, while differentiation into trophectoderm occurred when it was maintained at 50% or less and differentiation into primitive endoblast occurred when it was maintained at 150% or more (Niwa et al., Nature Genet., 24:373, 2000). When controlling differentiation by varying the expression level, strict control of the expression level will be possible by introducing a gene expression ON/OFF induction system (for example, tetracycline-based expression induction system) into the HAC vector produced according to the method of the present invention.

In addition, switching between the pluripotent state and the induced differentiation state will be possible by introducing a combination of a gene expression ON/OFF induction system (for example, tetracycline-based expression induction system) and a differentiation-inducing factor into the HAC vector produced according to the method of the present invention.

When performing tissue regeneration using stem cells, transplanted cells or donor-derived regenerated tissues will function as part of the recipient for an extended period (desirably for life). Therefore it is desirable that operations that may become a cause (for example, gene mutation) of induction of deviation from physiological control, such as canceration, in donor cells be avoided as far as possible. Because the HAC vector can be independent of host chromosomes, gene transfer can be performed without modifying host chromosomes. In addition, as shown in examples 13, 14, 18 and 19, because the HAC vector remains stable in human cells, it can express target molecules stably for a long time.

By producing the HAC vector according to the method of the invention into which DNA is introduced that is fused with a target gene under the genome sequence containing either a gene genome region that is expressed in differentiated tissues or a tissue-specific expression control region, and by using stem cells into which the HAC vector is transferred, it will be possible to express a target molecule in regenerated tissues in a physiological/tissue-specific manner.

After inducing the differentiation of the stem cells retaining the HAC vector produced according to the method of the present invention, the HAC vector may be unnecessary unless the expression of the introduced gene is required. By sorting HAC vector dropout clones after induced differentiation using, for example, but not limited to, drug resistance in selective culture as an indicator, it will be possible to remove the HAC vector which has become unnecessary.

(6) Vector for the Production of Culture Feeder Cells

As one of cell culture methods, a method is known which involves spreading adherent cells on the bed of a culture flask and seeding target cells onto these culture feeder cells for cocultivation (Ed. Japanese Biochemical Society, Shin-Seikagaku-Jikken-Koza 14-generation, differentiation and aging, 1992, Tokyo Kagaku Dojin). For example, when multiplying hematopoietic precursor cells, necessary factors, such as SCF, Flt3L, TPO, IL-6 and sIL-6R, are prepared as, for example recombinant proteins and added to the culture medium (Ueda et al., J Clin Invest., 105: 1013-1021, 2000). Although it is possible to introduce genes added to the culture into culture feeder cells by conventional method, it may be difficult to supply them by controlling the expression at a level desired for each factor due to the variation/position effect arising from random insertion into the host chromosome, inactivation of expression, and attenuation of downstream gene expression resulting from parallel arrangement of multicopy expression units. By producing the HAC vector incorporating all (or part of) the DNA that encodes these necessary factors according to the method of the present invention and transferring it into culture feeder cells, it will be possible to supply all the necessary factors easily by simple cocultivation only without adding recombinant proteins later.

In addition, the use of a gene expression induction system will enable the conditional control of expression of these factors.

(7) Vector for the Treatment of Human Disease

For vectors for the treatment of human disease, various viral and non-viral vectors have been studied, and several problems, such as the elicitation of immune response, limit to the size of DNA to be introduced, insertion mutation of host chromosomes, low introduction/expression efficiency, and difficulty in controlling expression levels (Kaneta, Y., Rinsho Menneki, Vol. 39: 551-558, 2003, Kagaku Hyoron-sha, ed. Ozawa, T., Idennshi Chiryo, 1997, Yodo-sha) have been noted. A common issue for all vectors is to "control the expression at a desirable level with good timing."

Examples of strategies for gene and cell therapy using the HAC vector include (i) supplementation with enzymes and proteins that are primarily deficient, (ii) supportive treatment to supplement with metabolites that are secondarily deficient, (iii) method of adding new functions to cells so as to improve their viability (for example, in tissue regeneration using modified cells, the HAC vector can perform physiological/tissue-specific gene expression control by introducing the genome DNA into it. This will help avoid adverse effects such as functional disorders due to overexpression or insufficient expression.) and (iv) method of preventing degenerative disease which progresses in gain-of-function (for example, GDNF replacement therapy in Parkinson disease).

The HAC vector can be used as a vector for the treatment of human disease, and the HAC vector incorporating therapeutic foreign DNA can be transferred into cells, which are then prepared as a pharmaceutical composition to administer to patients. In addition, the vector for the treatment of human disease can be used for the prevention of disease as well as for treatment.

The following examples of use as a vector for the treatment of human disease are provided for illustrative purposes only and not intended to limit the scope of the invention.

(A) Use of Telomerase

The cells used as raw material for gene and cell therapy and tissue regeneration therapy should be normal cells but not immortalized cells in light of safety. However, normal somatic cells are known to age, or stop multiplying/dividing before long, resulting in death, once they have undergone a given number of divisions (Ide, T., Jikken Igaku, Vol. 16 No. 18 Extra Number: 18-24, 1998, Yodo-sha). Therapeutic cells must be maintained for a certain period, desirably throughout the patients' life, so as to ensure long-lasting therapeutic effect. It is known that overexpression of telomerase, which is the repair enzyme for the repetitive sequence telomere present at the end of a chromosome, in normal cells will suppress the shortening of telomere occurring as cells age and extend cellular life (Bodnar et al., Science, 279: 349-352, 1998). In addition, overexpression of telomerase has been shown not to induce immortalization or canceration of cells (Shinkai, Y., Jikken Igaku, Vol. 16 No. 18 Extra Number: 25-30, 1998, Yodo-sha; Jiang et al., Nature Gent., 21: 111-114, 1999). Thus it is possible to extend the life of HAC-retaining cells and provide long-lasting therapeutic effect without inducing immortalization or canceration by transferring into target cells the HAC vector carrying the gene encoding human telomerase (hTERT) according to the method of the present invention. In addition, the use of an expression induction system or a genomic region for the control of gene expression will allow for conditional or tissue-specific/physiological expression of telomerase.

(B) Suppression of Generation of Autoantibody

Generation of autoantibodies (active neutralizing antibody) after administration has been an obstacle when developing a recombinant protein preparation (Li et al., Blood, 98:3241-3248, 2001). Although it is not intended to limit the method of administration to patients, the HAC vector produced by the method of the invention into which the genome encoding a target protein is introduced is transferred into human cells, for example normal human cells in the producing tissue, and transplanted to patients. In the patient, the target protein can be expressed and supplied from the HAC vector in a physiological/tissue-specific manner to suppress the generation of autoantibodies in the patient.

(C) Vector for Gene Transfer of Genes Involving in Immunity in Cell Therapy

As a treatment for recurrent leukemia, the donor lymphocyte infusion therapy (Kolb et al., Blood, 76:2462, 1990) is known which utilizes the phenomenon that transplanted lymphocytes attack leukemic cells as tumor-specific cytotoxic T cells through graft-leukemia reaction. As an approach to addressing graft-versus-host disease, an adverse effect of the therapy above in which transplanted cells attack and damage recipient tissues, donor lymphocytes have been removed by transferring a drug-inducible suicide gene to donor lymphocytes by retrovirus and using drugs (Onodera et al., Genome Medicine, Vol. 3: 45, 2003, Medical Review). This method may affect the chromosomes of donor lymphocytes.

The HAC vector produced according to the method of the present invention can be used as a vector for gene transfer of genes involving in immunity in cell therapy which does not cause host chromosomes to mutate. The HAC vector can also be used as a vector for gene transfer in therapy aimed at promoting antitumor activity, such as the immunological activation therapy (Kato et al., Genome Medicine, Vol. 3: 53, 2003, Medical Review) for lymphoma using CD40 ligand.

(D) Recruitment of Monoclonal Complete Human Antibody

In late years creation of a complete human monoclonal antibody drug using human antibody-producing mice has been tried (Ishida et al., Bio Venture, Vol. 2: 44, 2002, Yodosha; Mori et al., Cell Death and Differentiation, in press, 2003, Proceedings of American Association for Cancer Research, Volume 44, 2nd Edition, July 2003, p1285, #6422). However, because applying this to chronic disease requires continuous hospital visit for periodical TPO administration, the patient's QOL may decrease. In addition, the production of a recombinant protein preparation requires a large cost, resulting in high medical expenses.

By introducing a genome region encoding a target antibody isolated from the hybridoma producing the target antibody into the HAC vector produced according to the method of the present invention, transferring the HAC vector to, for example the patient's hematopoietic stem cells or B cells, then retransplanting them to the patient, it will be possible to recruit/supply complete human antibodies by controlling physiological expression. This may also decrease the number of hospital visits and improve the patient's QOL.

(E) Compensation for Defect in Single Gene Hereditary Disease (E-1) Hemophilia

Hemophilia A and hemophilia B are sex-linked recessive hereditary bleeding disease caused by mutation of the blood coagulation factor VIII and blood coagulation factor IX, respectively. Although the replacement therapy with concentrated preparations of factor VIII and factor IX is an effective treatment, there is need for solution using gene therapy since it may cause serious complications in the case of post-bleeding administration and have other problems, such as contamination of the concentrated preparation by pathogens, generation of autoantibodies (active neutralizing antibodies) due to repeated doses, decreased patient QOL because the patient must be prepared constantly for bleeding, and large medical expenses. Studies of clinical gene therapy conducted using vectors have not produced significant therapeutic effect since expression has not lasted for a sufficient time. In addition, in a clinical study in which retrovirus and adeno-associated virus (AAV) vectors were administered directly, the vector gene was detected in the subject's semen, suggesting a danger of gene transfer to germ cells (Mochizuki et al., Genome Medicine, Vol. 3: 25, 2003, Medical Review). The gene encoding factor VIII is about 1.5 Mb in full-length genome and about 7 kb for cDNA. Expression level may decrease in non-viral vectors and adenovirus vectors although full-length cDNA can be introduced, while full-length genes cannot be introduced in AAV vectors since the DNA to be introduced is limited to about 4.9 kb or less in length.

The method of the present invention can be used to produce the HAC vector that incorporates the DNA encoding coagulation factor VIII or IX. Although it is not intended to limit the method of administration to patients, the HAC vector can be transferred to, for example, human cells and transplanted to patients to recruit the factors. Although it is not intended to limit the method of administration to patients, the HAC vector incorporating the genome region of coagulation factor VIII or IX can be transferred to, for example, human cells and transplanted to the patient the cells are derived from to recruit the factors through physiological/tissue-specific expression.

(E-2) X-SCID (X-Linked Severe Combined Immunodeficiency)

Severe combined immunodeficiency (SCID) is a disorder in which humoral and cell mediated immunity is congenitally defective. About half the cases of SCID are X-linked X-SCID, and it is known to be caused by variation in the gamma chain which the receptors of the interleukin 2 family share. Transplantation with hematopoietic stem cells has been performed for treatment, though restoration of humoral immunity is insufficient and the periodical administration of immunoglobulin is necessary. Therefore a solution is expected which uses the gene and cell therapy that involves the introduction of the common gamma chain into hematopoietic stem cells followed by transplantation. In clinical studies conducted since 1999 on the transplantation of hematopoietic stem cells into which the common gamma chain was introduced using retrovirus, some cases of development of leukemia in transplanted cells have been reported in recent years in France (Hacein-Bey-Abina et al., N Engl J Med., 348: 255, 2003; Marshall et al., Science, 299:320, 2003). In either case, vector sequence insertion mutation was observed in the region of LMO2 gene, which is one of the proto-oncogenes in the chromosomes of the cell into which the gene was introduced, and the association between LMO2 activation and tumorigenesis has been suspected (Kume et al., Genome Medicine, Vol. 3: 9, 2003, Medical Review).

The method of the present invention can be used to produce the HAC vector that incorporates the DNA encoding the common gamma chain. It will be possible to avoid the risk of vector sequence insertion mutation in host chromosomes by using the HAC vector as a vector for gene transfer. Although it is not intended to limit the method of administration to patients, the HAC vector can be transferred to human cells (for example, human bone marrow-derived normal hematopoietic stem cells) and transplanted to patients to compensate for the deficiency in the common gamma chain through physiological/tissue-specific expression.

(E-3) Duchenne Type Muscular Dystrophy; DMD

Duchenne type muscular dystrophy is a X-linked recessive single gene disease that is caused by dysfunction of dystrophin due to mutation of the dystrophin gene (Hoffman et al., Cell, 51:919, 1987). Because dystrophin is a cytoskeletal protein, recruitment by direct administration is impossible, and gene therapy is expected for the treatment of DMD.

The dystrophin gene is of about 2.3 Mb in full-length genome and 14 kb for cDNA. Expression level may decrease in non-viral vectors and adenovirus vectors although full-length cDNA can be introduced (Liu et al., Mol. Ther., 4: 45, 2001; Dello Russo et al., Proc Natl Acad Sci USA, 97: 12979, 2002). In addition, in AAV vectors, the full-length gene could not be introduced since the DNA to be introduced was limited in size to about 4.9 kb or less, and the expression level of the introduced gene product decreased due to immune response in an experiment of gene transfer to skeletal muscle (Yuasa et al., Gene Therapy, 9:1576, 2002).

In an experiment of gene transfer to skeletal muscle using the AAV vector incorporating the dystrophin minigene under the control of a CMV promoter which induces ubiquitous expression, immune response caused the expression level of the introduced gene product to decrease, though the immune response was improved by using as a promoter a MCK promoter which was specific for skeletal muscle (Yuasa et al., Gene Ther., 9:1576, 2002). This suggests that physiological, tissue specific expression is necessary for the expression of dystrophin.

The method of the present invention can be used to produce the HAC vector that incorporates the genome region encoding dystrophin. Although it is not intended to limit the method of administration to patients, the HAC vector can be transferred to human cells (including, but not limited to, autologous human normal myoblast) and transplanted to patients to recruit dystrophin through physiological/tissue-specific expression.

(E-4) Although it is not intended to limit indications, the method of the invention can be used to produce the HAC vector into which the causal gene for a single-gene disorder, for example α-1 antitrypsin deficiency, cystic fibrosis (CFTR), chronic granulomatous disease, familial hypercholesterolemia, Fanconi's anemia, Gaucher's disease, Hunter's syndrome, ornithine transcarbamylase deficiency, purine nucleotide phosphorylase deficiency, ADA-SCID, leukocyte adhesion deficiency, Canavan disease, callosum atrophy, Fabry's disease and amyotrophic lateral sclerosis, and, although it is not intended to limit the method of administration to patients, the HAC vector can be transferred to, for example, human cells and transplanted to patients to recruit the deficient molecules. For information on disease causing genes, see the on-line literature database PubMed (http://www at site ncbi.nlm.nih.gov/entrez/query.fcgi?db=PubMed) of the US National Center for Biotechnology Information (NCBI) or OMIM™—Online Mendelian Inheritance in Man (www.ncbi.nlm.nih.govientrez/query.fcgi?db=OMIM).

(F) Other Diseases (F-1) Thrombopoietin (TPO) is a factor responsible for the control of platelet production and multiplication of hematopoietic stem/precursor cells, and application to, for example, blood disease such as aplastic anemia, and recovery of hematopoiesis after chemotherapy is expected. However, the generation of active neutralizing antibody after the administration of TPO recombinant protein has been an obstacle to the development of a pharmaceutical preparation (Li et al., Blood, 98:3241-3248, 2001). Thus, because applying TPO to chronic disease requires continuous hospital visit for periodical TPO administration, the patient's QOL may decrease. In addition, the production of a recombinant protein preparation requires a large cost, resulting in high medical expenses.

The method of the present invention can be used to produce the HAC vector into which the TPO genome region is introduced and, although it is not intended to limit the method of administration to patients, the HAC vector can be transferred to human cells, for example cells from the platelet-producing tissue, to express/supply TPO in a physiological/tissue-specific manner to control the generation of autoantibodies. This may also decrease the number of hospital visits and improve the patient's QOL.

(F-2) Erythropoietin (EPO) is a erythrocyte growth factor that is marketed as, for example, remedies for renal anemia associated with diabetes and kidney disease. Because the treatment of chronic disease (for example, renal anemia due to diabetes) requires continuous hospital visit for periodical EPO administration, the patient's QOL may decrease. In addition, the production of a recombinant protein preparation requires a large cost, resulting in high medical expenses. As shown in example 14 of the present invention, by transferring the HAC vector (into which EPO cDNA is introduced) to human normal fibroblasts then transplanting them to a patient, EPO can be expressed and supplied to the patient. The method of the present invention can be used to produce the HAC vector into which the EPO genome region is introduced and, although it is not intended to limit the method of administration to patients, the HAC vector can be transferred to human cells, for example cells from the erythrocyte-producing tissue, to express/supply EPO in a physiological/tissue-specific manner. This may also decrease the number of hospital visits and improve the patient's QOL.

(F-3) Parkinson Disease

Parkinson disease is a neurologic disease in which the motor function is impaired as a result of progressive degeneration of dopamine synthesis cells in the mesencephalic substantia nigra pars compacta. The problem with one of the treatments which involves the administration of L-DOPA aimed for the replacement of deficient dopamine is that its effectiveness decreases in moderate to severe cases and the patient QOL is reduced and the dose decreased due to adverse effects. Because these problems result from the fact that the dopamine concentration is inconsistent in the striatum and that the administered L-DOPA acts in regions other than the striatum, constant physiological expression of dopamine in the striatum is required (Takeda et al., Medical Science Digest, Vol. 29: 20, 2003, New Science). Although study has been conducted on gene therapy using AAV vectors into which each of three kinds of enzymes involved in dopamine synthesis is introduced, the control of physiological expression has not been attained. For GDNF (Grial-cell Derived Neuronal Factor) therapy, a treatment aimed for the prevention of degeneration/falling of dopamine synthesis cells, continuous medication using a indwelling catheter placed under the putamen produced therapeutic effect (Gill et al., Nature Med., 9:589, 2003) while there was the danger of contracting infections and the patient QOL was limited. Study on gene therapy with an AAV vector showed some therapeutic effect in animal models (Wang et al., Gene Ther., 9:381, 2002), but the control of physiological expression has not been reached.

The method of the present invention can be used to produce the HAC vector that incorporates the genome region encoding a group of enzymes involved in dopamine synthesis or GDNF. Although it is not intended to limit the method of administration to patients, the HAC vector can be transferred to human cells (for example, human normal neural stem/precursor cells) and transplanted to a patient to recruit the introduced gene product through physiological/tissue-specific expression.

(F-4) Diabetes

Insulin dependent diabetes has been treated with recombinant protein preparations. Because the treatment of chronic disease requires continuous hospital visit for periodical drug administration, the patient's QOL may decrease. In addition, the production of a recombinant protein preparation requires a large cost, resulting in high medical expenses. Because the optimum range of blood insulin concentration is narrow, adverse effects may occur whether the concentration is too high or too low, often resulting in a threat to life. The control of insulin concentration in the body has been the subject of gene therapy study (Moriya et al., Tanpakushitsu Kakusan Koso, Vol. 40: 2764, 1995, Kyoritsu Shuppan Co., Ltd.).

The method of the present invention can be used to produce the HAC vector into which the insulin genome region is introduced and, although it is not intended to limit the method of administration to patients, the HAC vector can be transferred to human cells, for example cells in the producing tissue, to express/supply insulin in a physiological/tissue-specific manner. This may also decrease the number of hospital visits and improve the patient's QOL.

(F-5) Although it is not intended to limit indications, the method of the invention can be used to produce the HAC vector into which the gene encoding the substance that is considered necessary for the treatment of, for example, brain tumor, peripheral arterial disease (ischemia), rheumatoid arthritis, artery restenosis, cubital tunnel syndrome, coronary artery disease, Alzheimer disease, ulcer, pelvic fracture, kidney disease and malignant tumor, and, although it is not intended to limit the method of administration to patients, the HAC vector can be transferred to, for example, human cells and transplanted to patients to recruit the deficient molecules.

EXAMPLES

The present invention will be described in detail below by way of Examples, which should not be construed as limiting the scope of the present invention.

Example 1

Preparation of HAC Vector by Deleting Distal Region of the Long-Arm of Human Chromosome 21

(1) Construction of a Construct for Telomere Truncation

As a telomere truncation vector (targeting vector) for use in deleting a distal region of the long-arm of human chromosome 21, PBS-TEL/Puro (Kuroiwa, Nucleic Acids Res., 26:3347, 1998) was used. Based on the nucleotide sequence (Accession No. AL163204) of the long-arm distal region of human chromosome 21, which was obtained from the GenBank database, a target sequence for use in inserting the telomere truncation vector was designed. To amplify the sequence, primer oligonucleotides were used. The sequences of the primer oligonucleotides, to which a recognition sequence for restriction enzyme BamH I was added, are shown below:

```
#21telF1:
                                       (SEQ ID No. 1)
5'-CGCGGATCCAGAGAGAGCCTGGAATGCCTGGTAGTGT

#21telR1:
                                       (SEQ ID No. 2)
5'-CGCGGATCCCCAGTGCCCTGAGATCTTGTGATTTCTC
```

DT40 hybridoma cell retaining human chromosome 21 was prepared by a microcell method by using mouse A9 hybridoma cell (Shinohara, Hum Mol Genet, 10: 1163, 2001) retaining human chromosome 21, as a chromosome donor cell. A chromosome recipient cell, DT40 is available since it has been registered under Accession No. JCRB 2221 at the Japanese Collection of Research Bioresources (JCRB). Now, a method of preparing DT40 hybridoma cell will be generally described below.

First, microcells were prepared from about $1 \times 10^8$ A9 (#21 neo) cells. A9 (#21 neo) cells were cultured in twelve 25 cm²-centrifugation flasks (Coasters) until a cell density reached about 60 to 70% saturation. These A9 (#21 neo) cells were further cultured in a culture solution (10% CS, 0.05 µg/ml, G418, DMEM) containing colcemid (0.05 µg/ml, Demecolcine, Wako Pure Chemical Industries, Ltd.) for 72 hours to induce micronuclei. In this Example, DMEM manufactured by Invitrogen was used. After the medium was removed, each of the centrifugation flasks was filled with a pre-heated (34° C.) cytochalasin B solution (10 µg/ml in DMEM, Sigma), inserted in an acrylic centrifugation vessel, and centrifuged (34° C., 8000 rpm) for one hour. The microcells were recovered by suspending them in a serum-free medium (DMEM, Sigma) and purified by filtration. The microcells thus purified were resuspended in 4 ml of DMEM supplemented with 10 µg/ml phytohemaggulutinin-P (Sigma). DT40 cells ($1 \times 10^8$ cells) were seeded in 2 wells of a 6-well cluster (Nunc) coated with 50 µg/ml Poly-L-Lysine (Sigma) and then allowed to stand for one hour. In this manner, DT40 cells were allowed to previously adhere at the bottom. To the wells, the microcell suspension was added and allowed to stand for 3 minutes, and then the supernatant was removed. The remaining matter was treated with 50% w/v polyethylene glycol 1500 (Roche Diagnostics) for one minute. The fused cells thus obtained were suspended in 12 ml of serum-free DMEM, seeded in 4 wells of a 6-well plate, and cultured for 24 hours, and thereafter, subjected to selective culturing in a medium containing 1.5 µg/ml G418 for about 2 weeks. The formed drug resistant colonies were isolated.

The DT 40 hybrid cells obtained above were cultured and genomic DNA was extracted from the cells by use of a Puregene DNA Isolation kit (Gentra System). Using this genomic DNA as a template, the target sequence for recombination was amplified by PCR method using the aforementioned primers. The PCR was performed using about 0.1 µg of genomic DNA as a template by a thermal cycler, Gene-Amp9700 (Applied Biosystems), in accordance with Innis et al. (PCR experiment manual, HBJ publisher, 1991). The reaction was performed by using LA Taq (Takara Shuzo Co., Ltd.) as Taq polymerase, and the reaction condition includes reaction at 95° C. for 2 minutes, and 35 cycles of denaturation at 95° C. for 30 seconds and annealing/extension at 68° C. for 6 minutes. The amplified product was digested with restriction enzyme BamH I (Nippon Gene) and about a 5 kb DNA fragment having cohesive ends were separated and purified by agarose gel electrophoresis. This fragment was cloned into a BamH I site of PBS-TEL/Puro plasmid. The size of the PBS-TEL/Puro construct finally obtained was about 10.6 kb. The telomere truncation vector, the target sequence and the chromosomal allele to be resulted by homologous recombination are shown in FIG. 1.

(2) Transfection and Isolation of Puro-Resistant Clone

The PBS-TEL/Puro construct was digested with restriction enzyme EcoR I to provide linear DNA, which was introduced in a DT 40 hybrid cell retaining human chromosome 21. DT40 hybrid cells ($1 \times 10^7$) were suspended in 0.75 ml of PBS and subjected to electroporation by use of Gene Pulser (Biorad) in the presence of 25 µg of DNA. A voltage of 750V was applied to a condenser having a capacitance of 25 µF and allowed to discharge by use of an electroporation cell having electrodes placed at an interval of 4 mm. The electroporated cells were suspended in DMEM medium (Invitrogen) supplemented with 10% fetus bovine serum (FBS), 1% chicken serum (ChS), and 50 µM 2-mercaptoethanol, and seeded in two 96-well clusters (Falcon). Two days later, puromycin dihydrochloride (Sigma) was added so as to have a final concentration of 0.3 µg/ml. Resistant colonies were formed in 2 to 3 weeks. The frequency of colony formation was 17.8 colonies in average per 1×10⁷ DT40 hybrid cells. Transfection was performed 20 times to isolate 356 drug resistant colonies in total. The colonies were proliferated and subjected to the following analysis.

(3) Selection of a Recombinant and Confirmation of Telomere Truncation (3-1) PCR Analysis Using the genomic DNA of a puromycin resistant strain as a template, the presence of gene markers and STS markers (D21S265, CBR, SIM2, D21S268, D21S266, D21S1259) on human chromosome 21 was detected by the PCR method.

The sequences of primer oligonucleotides for these STS markers can be available by accessing to the on-line database: UniSTS (http://www at site ncbi.nlm.nih.gov/entrez/query.fcgi?db=unists) of the National Center for Biotechnology Information of the United States. The Registration Numbers of the aforementioned 6 types of STS markers are UniSTS: 76223, 45641, 54124, 22625, 54266, and 53746 sequentially in the order. Besides these, the sequences of primer oligonucleotides for the genes, which were designed based on the nucleotide sequence obtained from the GenBank database, are shown below:

```
                                    (SEQ ID No. 3)
PRED65F:    5'-GCCTGGCATCTTCCTCAATA;

(SEQ ID No. 4)
PRED65R:    5'-TTGCATGCCTGTGGTACTGT;

(SEQ ID No. 5)
PRED3F:     5'-TCACAATCATGGGCTTTGAA;

(SEQ ID No. 6)
PRED3R:     5'-CACGCAACCATTTGTTCATT.
```

Figure 2:
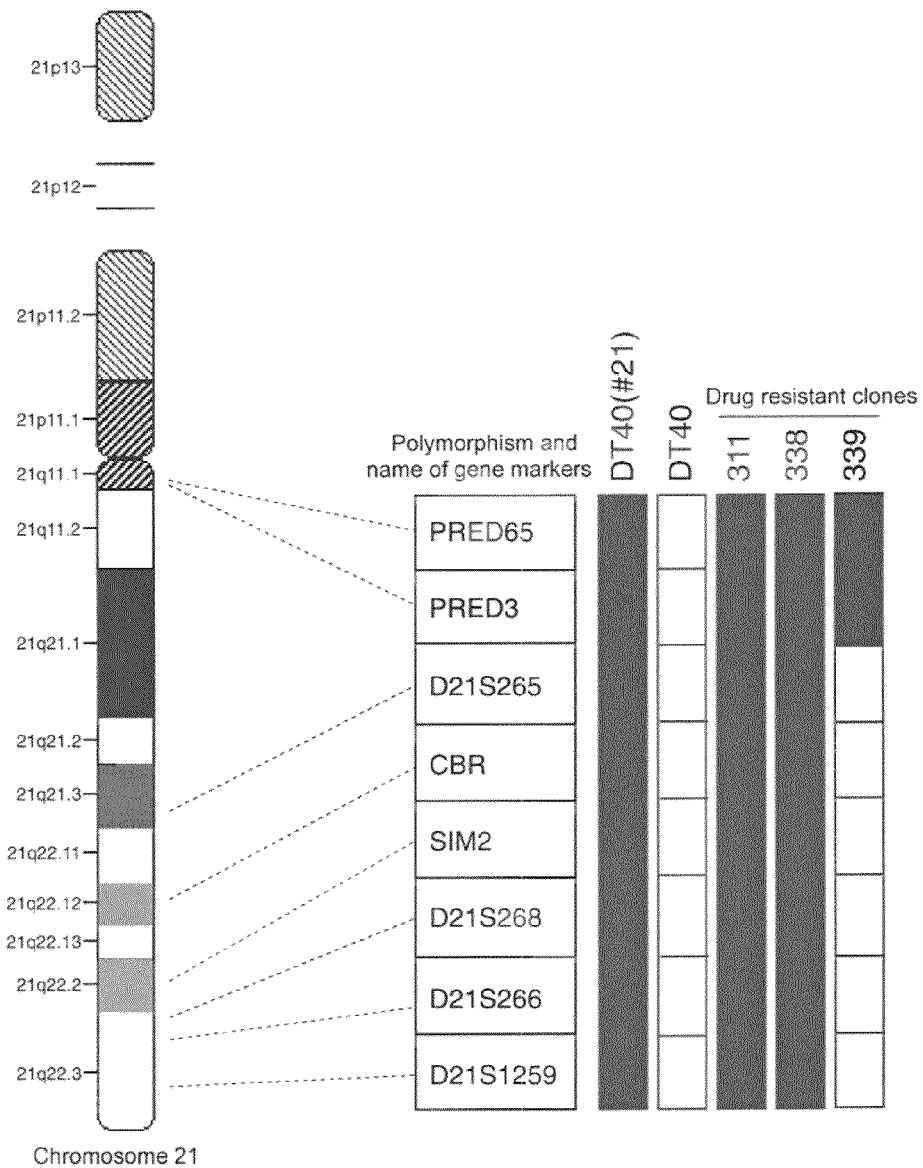
FIG. 2 shows the results of PCR analysis indicating the deletion of the distal region of the long arm of human chromosome 21 in the puromycin resistant DT40 clone.

Using about 0.1 µg of genomic DNA as a template, three out of the aforementioned 8 types, that is, PRED 3 gene located in the proximity of a deletion site by homologous recombination, D21 S265 marker and D21 S266 marker located in the distal region thereof were amplified by PCR (Innis et al., supra). In the case where a long-arm distal region was deleted by telomere truncation, it was predicted that the genomic DNA might have PRED 3 gene but not have D21S265 and D21D266 markers. As a result, amplification was performed as predicted in 24 out of resistant 354 clones. These 24 clones were subjected to PCR amplification by use of the remaining 7 types of markers to determine the region carrying human chromosome 21 therein. Representative results are shown in FIG. 2. In FIG. 2, a schematic chromosomal map made on the basis of the G band image of human chromosome 21 is given at the left-hand side. In addition, it is shown which marker is present in which band. In three types of puromycin resistant DT40 clones, a marker that was detected in an expected PCR amplification product, is indicated by a solid square, whereas the marker that was not detected in an expected PCR amplification product, is indicated by an open square. DT40 (#21) represents a cell before subjected to telomere truncation.

(3-2) Southern Blot Analysis

A probe was designed within the target sequence for homologous recombination (FIG. 1). As the probes, the pair of oligonucleotide primers shown below were used. PCR was performed by using the genomic DNA of a DT40 hybrid cell retaining human chromosome 21 as a template. Thereafter, a PCR amplification fragment was isolated and purified.

```
                                    (SEQ ID No. 7)
21qtelF:   5'-TCACAGCCAGCAGAGGATTC (SEQ ID No. 8)
21qtelR:   5'-CACCTGCACAATGGCTCAAC
```

Figure 3:
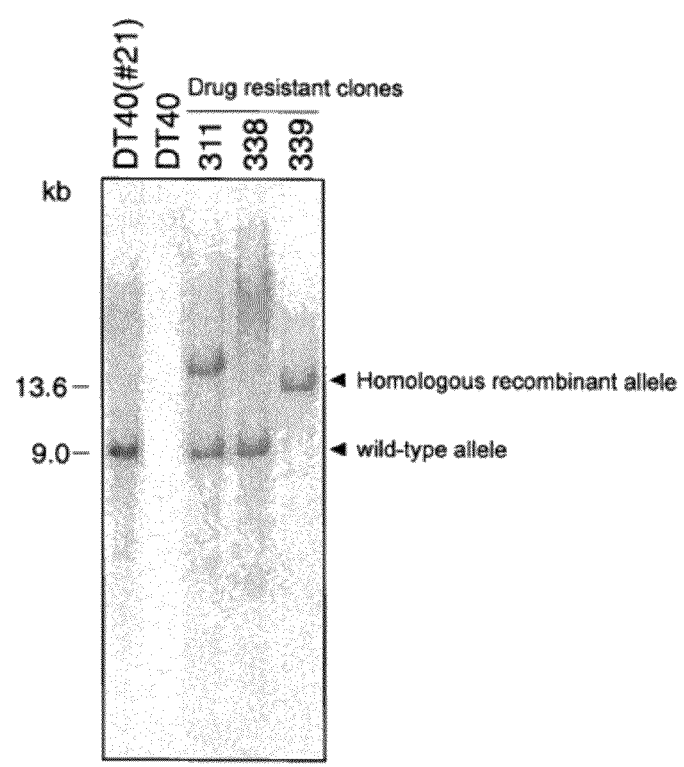
FIG. 3 is a photograph showing the results of southern blot analysis indicating the deletion of the distal region of the long arm in the puromycin resistant DT40 clone, or the introduction of an artificial telomere sequence in a site-specific manner.

About 10 µg of genomic DNA extracted from the 24 clones obtained by the primary screening was digested by restriction enzyme Kpn I (Takara Shuzo Co., Ltd.) and subjected to Southern blot analysis in accordance with the method described in Ausubel et al. (Current Protocols in Molecular Biology, John Wiley & Sons, Inc., 1994). A signal from the DNA hybridized with a probe labeled with ³²P was detected by image analyzer BAS2000 (Fuji Photo Film Co., Ltd.). Representative results are shown in FIG. 3. The length of a restriction enzyme fragment was predicted based on a nucleotide sequence. It was 13.6 kb in the case of a homologous recombinant, and 9.0 kb in the case of a wild type (non-homologous recombinant) It was confirmed that 2 clones out of 24 candidate clones were homologous recombinants.

(3-3) Fluorescence In Situ Hybridization (FISH)

Figure 4:
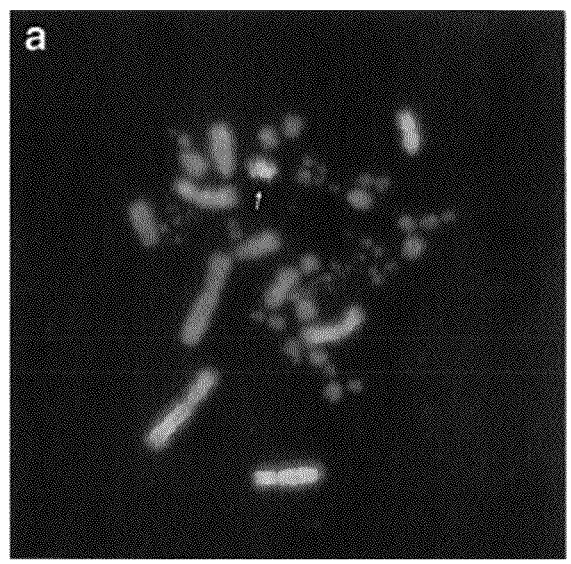
FIGS. 4a and 4b are photographs showing the results of FISH analysis indicating the deletion of the distal region of the long arm in the puromycin resistant DT40 clone.
Figure 4:
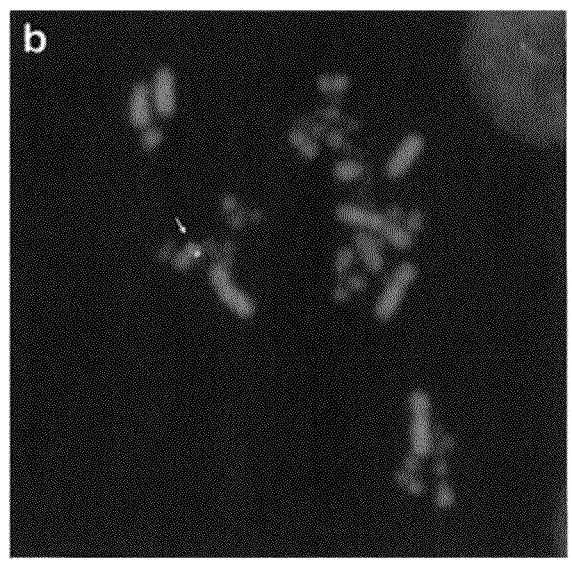

FISH analysis was performed using a human specific probe Cot1 (Gibco BRL) in accordance with the method described in Matsubara et al. (FISH experimental protocol, Shujunsha, 1994). As a result, truncated human chromosome 21 was detected in almost all the mitotic images observed. Representative FISH images are shown in FIGS. 4a and 4b. In FIG. 4a, the white arrow shows full-length human chromosome 21 before telomere truncation. In FIG. 4b, the white arrow shows a fragment of human chromosome 21 where a long-arm distal region is deleted. Based on relative comparison with the chromosome of the host DT40 cell in size, it was confirmed that human chromosome 21 was truncated.

From the experiment above, it was confirmed that 2 puromycin resistant clones retain the truncated human chromosome 21 devoid of the long arm.

Example 2

Insertion of loxP Sequence into the Proximal Region of Human Chromosome 21 in HAC Vector (1) Construction of a Construct for Inserting loxP As a basic plasmid for inserting a loxP sequence into the human artificial chromosome (HAC) prepared in Example 1, pSF1 (Lifetech) was used. The nucleotide sequence of a loxP insertion site, that is, a proximal region of the long-arm of human chromosome 21, was obtained from the GenBank database (Accession No. AL163203). The sequences of primer oligonucleotides used in amplifying 2 target sequences for homologous recombination are shown below:

```
                                    (SEQ ID No. 9)
#21qEcoF:   5'-CCGGAATTCCTCTGGGTTTCTGGTGAAGC;

(SEQ ID No. 10)
#21qEcoR:   5'-CCGGAATTCTGTAGATCCTGCCATTGTGG;
```

-continued

```
                                            (SEQ ID No. 11)
#21qBaF:        5'-CGCGGATCCTTGGCTCCAAAAGGTACCAC;

(SEQ ID No. 12)
#21qBaR:        5'-CGCGGATCCCTATCCTCGCCACTGTGTCC.
```

Using the genomic DNA extracted from a DT40 hybridoma cell retaining human chromosome 21, as a template, two target sequences were amplified by PCR. Each of them was digested with restriction enzymes EcoR I (Nippon Gene) or BamH I (Nippon Gene) and subjected to agarose gel electrophoresis, thereby separating and purifying an about a 3 kb DNA fragment having cohesive ends. The fragments each are ligated to an EcoR I site or BamH I site of pSF1 plasmid. A blasticidin resistant gene for use in screening of a homologous recombinant was excised out as about a 1.3 kb fragment from pCMV/Bsd (Invitrogen) by digestion with restriction enzymes Xho I (Nippon Gene) and Sal I (Nippon Gene) and cloned into the Xho I site of the pSF1 construct obtained above.

Figure 5:
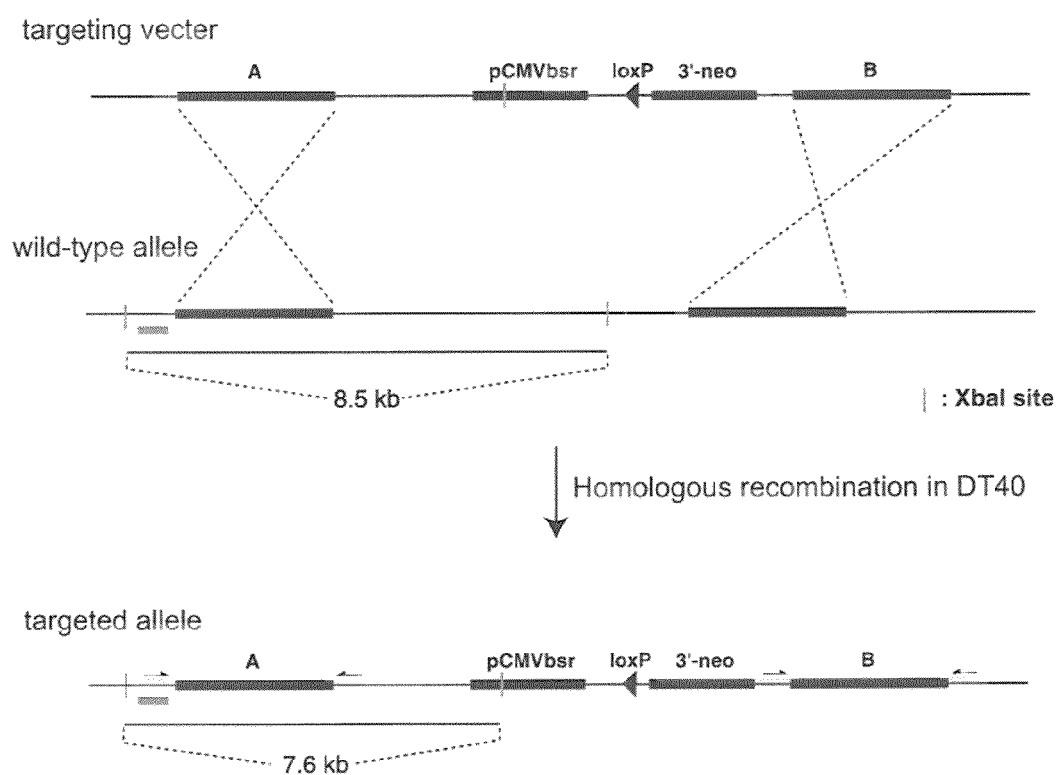
FIG. 5 is a schematic view showing the method of inserting in a site-specific manner a loxP sequence into the proximal region of the long arm of human chromosome 21 from which the distal region of the long arm has been deleted.

The size of the pSF1 construct finally obtained was about 12.4 kb. The targeting vector, target sequence, and the chromosomal allele obtained by homologous recombination are shown in FIG. 5.

(2) Transfection and Isolation of bsr-Resistant Clone

The pSF1 construct was digested with restriction enzyme Apa I (Nippon Gene) to obtain linear DNA, which was introduced into a DT40 strain (DT40 (#21) puro-339) retaining human chromosome 21 where a long-arm distal region was deleted. DT40 hybrid cells ($1 \times 10^7$) were suspended in 0.75 ml of PBS and subjected to electroporation using Gene Pulser (Biorad) in the presence of 10 µg of DNA. A voltage of 750V was applied to a condenser having a capacitance of 25 µF and allowed to discharge by use of an electroporation cell having electrodes placed at an interval of 4 mm. The electroporated cells were suspended in DMEM medium (Invitrogen) supplemented with 10% fetus bovine serum (FBS), 1% chicken serum (ChS), and 50 µM 2-mercaptoethanol and seeded in three 96-well clusters (Falcon). Two days later, Blasticidin S Hydrochloride (Funakoshi) was added so as to have a final concentration of 8 µg/ml. Resistant colonies were formed in 2 to 3 weeks. The frequency of colony formation was 5.8 colonies in average per $1 \times 10^7$ DT40 hybrid cells. Transfection was performed 14 times to isolate 82 colonies in total. The colonies were proliferated and subjected to the following analysis.

(3) Selection of a Recombinant (3-1) Southern Blot Analysis

Southern blot analysis was performed to screen homologous recombinants. A probe was designed outside the target sequence for homologous recombination. A pair of oligonucleotide primers as shown below were used as the probes. PCR was performed using the genomic DNA of a DT40 hybrid cell retaining human chromosome 21, as a template. The PCR amplified fragment was isolated and purified.

```
                                            (SEQ ID No. 13)
21LOX4869F:     5'-GTTGCAGAAAAGTAGACTGTAGCAA (SEQ ID No. 14)
21LOX5682R:     5'-TCTAAGGAACAAATCTAGGTCATGG
```

Figure 6:
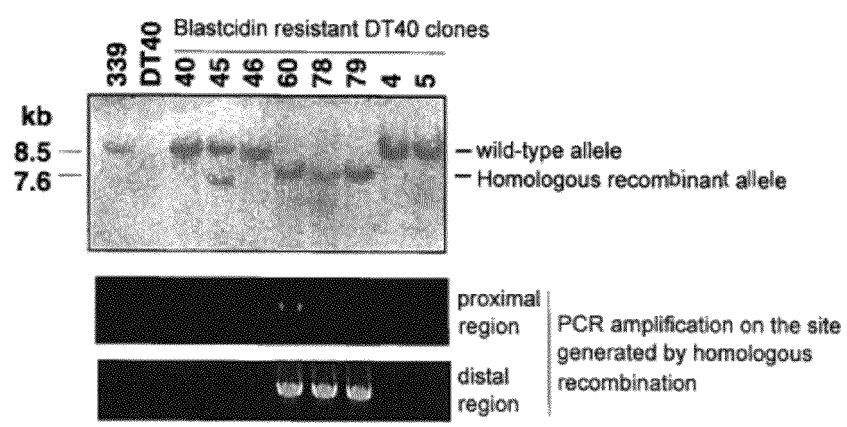
FIG. 6 is a photographs showing the results of southern blot analysis (A) and PCR analysis (B) used to screen the blasticidin resistant DT40 clone for homologous recombinants (clones in which the loxP sequence was introduced into human chromosome 21 in a site-specific manner).

About 10 µg of the genomic DNA extracted from a blasticidin resistant clone was digested by restriction enzyme Xba I (Nippon Gene) and subjected to Southern blot analysis (FIGS. 6A and 6B). A probe was labeled with $^{32}$P and the signal was detected by image analyzer BAS2000 (Fuji Photo Film Co., Ltd.). In FIG. 6A, the first lane from the left shows a DT40 clone retaining human chromosome 21 before a loxP site is introduced; the second lane shows host DT 40 cell clone; and the third lane and subsequent lanes show blasticidin resistant DT 40 clone. The length of a restriction enzyme fragment was predicted based on a nucleotide sequence. It was 7.6 kb in the case of a homologous recombinant and 8.5 kb in the case of a wild type (non-homologous recombinant). It was found that 3 in total out of 82 blasticidin resistant clones were homologous recombinants (#60, #78, #79).

(3-2) PCR Analysis

With respect to two target sequences, that is, the left and right sequences (indicated by A and B, respectively, in FIG. 5), a pair of oligonucleotide primers were designed so as to flank each of the target sequences. These pairs of oligonucleotide primers were designed on the chromosome and on the targeting vector. The positions of the primer pairs are indicated by arrows in FIG. 5. The sequences of the primer pairs are as follows:

```
                                            (SEQ ID No. 15)
Left455F:       5'-GGGCTAGCCATTAAAGCTGA;

(SEQ ID No. 16)
Left638R:       5'-AAAGGGAATAAGGGCGACAC;

(SEQ ID No. 17)
Right958F:      5'-GGTTTGTCCAAACTCATCAATGTA;

(SEQ ID No. 18)
Right1152R:     5'-GTCAATTCACTAATTCCTATTCCCAGT.
```

Genomic DNA was extracted from candidate clones obtained in Southern blot analysis and subjected to PCR. It was confirmed that the amplified product in the case of (A) on the left side had 3283 bps, whereas the amplified product in the case of (B) on the right side had 3114 bps, as predicted from the nucleotide sequences. The results are shown in FIG. 6B.

From the experiments (1) to (3) above, it was confirmed that 3 out of the obtained 82 blasticidin resistant DT40 clones retain a partial fragment (HAC vector) of human chromosome 21 having a loxP sequence inserted therein by homologous recombination.

Example 3

Transfer of HAC Vector Derived from Human Chromosome 21 into Hamster Cell Line (1) Microcell Fusion and Isolation of Drug Resistant Clone As a chromosome donor cell, DT40 cell (DT40(#21) bsd-79) retaining a HAC vector derived from human chromosome 21 obtained in Examples 1 and 2 by deleting a long-arm distal region and inserting a loxP sequence was used. As a chromosome recipient cell, Chinese hamster ovary derived cell line, CHO-K1 (available from ATCC, Accession No. JCRB9018) was used.

First, microcells were prepared from about $10^9$ DT40 (#21) bsd-79 cells. The DT40 (#21) bsd-79 cells were cultured up to a cell density corresponding to about 60 to 70% saturation in a culture solution (10% FBS, 1% ChS, 50 µM 2-mercaptoethanol, DMEM) containing colcemid (0.075 µg/ml, Demecolcine, Wako Pure Chemical Industries, Ltd.) for 12 to 15 hours to induce micronuclei. The cells were centrifugally collected, suspended in serum-free DMEM, and seeded in twelve 25 cm²-centrifugation flasks (Coasters) previously coated with poly-L-lysin. The flasks were allowed to stand still at 37° C.

for one hour. After the cells were adhered, the culture solution was removed. Each of the centrifugation flasks was filled with a pre-heated (37° C.) solution of cytochalasin B (10 µg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration. The purified micronucleus cells were added to a 6 cm-diameter dish where CHO-K1 cells were cultured up to 80% saturation. They were fused with a PEG solution. Forty eight hours later, the fused cells were dispersed by trypsin treatment and cultured in a selective medium (10% FBS, F12) containing blasticidin (8 µg/ml). After selective culture was performed for about 2 weeks, formed drug resistant colonies were separated and subjected to the following analysis. Microcell fusion was performed 12 times to obtain 4 blasticidin-resistant CHO clones in total.

(2) Confirmation of Transferred Chromosome (2-1) PCR Method

Whether a chromosome was transferred or not was confirmed by the PCR method. More specifically, an attempt was made to detect marker genes, PRED 65 and PRED 3 genes (see Example 1, (3)) located in the proximal region of the long-arm of human chromosome 21. It was confirmed that 2 types of marker sequences were amplified in all of the 4 blasticidin-resistant CHO cell clones.

(2-2) Fluorescence In Situ Hybridization (FISH) Analysis

Figure 7:
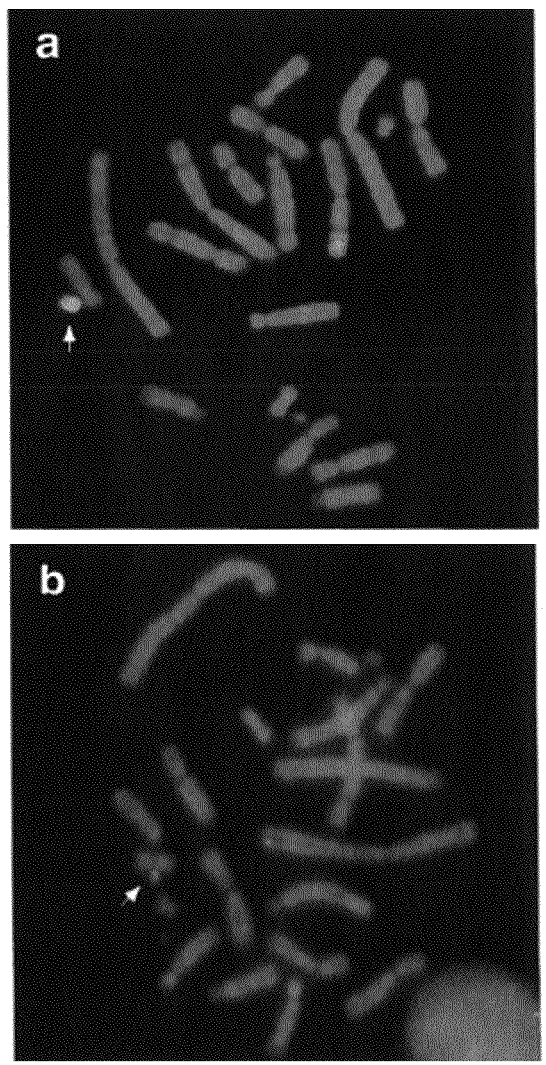
FIGS. 7a and 7b are photographs showing the results of FISH analysis indicating the retention of a human chromosome 21 (fragment) in the blasticidin resistant CHO-K1 clone.

FISH analysis was performed using a human specific probe Cotl (Gibco BRL) in accordance with the method described in Matsubara et al. (FISH experimental protocol, Shujunsha, 1994). When two clones (CHO(#21)bsd79-1 and CHO(#21)bsd79-3) out of the blasticidin resistant CHO cell clones were analyzed, truncated human chromosome 21 was detected in almost all the mitotic images observed. Representative FISH images are shown in FIGS. 7a and 7b. FIG. 7a shows full-length human chromosome 21 before subjecting to telomere truncation. FIG. 7b shows a fragment of human chromosome 21 where a long-arm distal region is deleted. Based on relative comparison with the chromosome of the host CHO cell in size, it was confirmed that truncated human chromosome 21 was transferred into the CHO cell.

From the experiments (1) and (2) above, it was confirmed that the obtained blasticidin resistant CHO clones retain a partial fragment of human chromosome 21 (HAC vector) where a long-arm distal region is deleted and a loxP sequence is inserted.

Example 4

Transfer of HAC Vector Derived from Human Chromosome 21 into a Human Cell Line and Confirmation of Stability of HAC Vector Derived from Human Chromosome 21 in the Culture Cell (1) Microcell Fusion and Isolation of Drug Resistant Clone As a chromosome donor cell, CHO cell (CHO(#21)bsd-79-1) retaining a HAC vector derived from human chromosome 21 obtained in Example 3 by deleting a long-arm distal region and inserting a loxP sequence was used. As a chromosome recipient cell, human fibrosarcoma cell line, HT1080 (available from ATCC, Accession No. CCL-121), was used. First, microcells were prepared from about $10^7$ CHO(#21)bsd-79-1 cells. More specifically, the CHO ((#21)bsd-79-1 cells, which were cultured up to a cell density corresponding to about 60 to 70% saturation in six 25 cm²-centrifugation flasks (Coasters), were further cultured in a culture solution (10% FBS, 8 µg/ml blasticidin, F12) containing colcemid (0.075 µg/ml, Demecolcine, Wako Pure Chemical Industries, Ltd.) for 48 hours to induce micronuclei. After the medium was removed, each of the centrifugation flasks was filled with a pre-heated (37° C.) solution of cytochalasin B (10 µg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration. The purified micronucleus cells were added to a 6 cm-diameter dish having HT1080 cells cultured up to 80% saturation. They were fused with a PEG solution. Forty eight hours later, the fused cells were dispersed by trypsin treatment and cultured in a selective medium (10% CS, DMEM) containing blasticidin (8 µg/ml). After selective culture was performed for about 2 weeks, formed drug resistant colonies were isolated and subjected to the following analysis. Microcell fusion was performed twice to obtain 12 blasticidin-resistant HT1080 clones in total.

(2) Confirmation of Transferred Chromosome (2-1) PCR Method

Whether a chromosome was transferred or not was confirmed by amplifying a blasticidin resistant gene by PCR. The sequences of oligonucleotide primers used herein are shown below:

```
                                          (SEQ ID No. 19)
    Bsd2687F:      5'-CAACAGCATCCCCATCTCTG;

(SEQ ID No. 20)
    Bsd2891R:      5'-GCTCAAGATGCCCCTGTTCT.
```

It was confirmed that the sequence of the drug resistant gene was amplified in all of the 12 blasticidin-resistant HT1080 cell clones.

(2-2) Chromosome Analysis

Chromosome analysis was performed by Giemsa staining in accordance with the method described in Kuroki et al. (Cell engineering handbook, Yodosha, 1992). About 20 metaphase chromosomal images of 4 clones (HT1080(#21)bsd79-1-3,6, 11,14) out of the blasticidin resistant HT1080 clones were analyzed. A mini chromosome, which was smaller than endogenous chromosome 21 and not observed in the parent cell line, HT1080, was observed in a blasticidin resistant clone.

From the experiments (1) and (2), it was confirmed that the obtained blasticidin resistant HT1080 clones retain a partial fragment (HAC vector) of human chromosome 21 where a long-arm distal region is deleted and a loxP sequence is inserted.

(3) Long-Term Subculture Under Nonselective Culture Conditions

To confirm the stability of human chromosome 21 where a long-arm distal region was deleted in a cultured cell, long-term subculture was performed under nonselective culture conditions. The aforementioned chicken cell lines (DT40 (#21)bsd-79) and human cell clones (HT1080(#21)bsd79-1-3, 6, 11, 14) were used. As the nonselective culture solution for the chicken cell line, DMEM supplemented with 10% FBS, 1% ChS, and 50 µM 2-mercaptoethanol was used. A selective culture solution was prepared by adding 8 µg/ml (in the case of DT40(#21)bsd-79) of blasticidin to the nonselective culture solution. As the nonselective culture solution for human cell clones, DMEM supplemented with 10% CS was used. A selective culture solution was prepared by adding 4 µg/ml of blasticidin to the nonselective culture solution. In the cases of the chicken cell line, $1.5 \times 10^7$ cells were seeded in a 10 cm-diameter dish. One day later, the number of cells was determined and 1.5×10⁷ cells were again seeded in a 10 cm-diameter dish. In the cases of the human cell clones, 5.0×10⁵ cells were seeded in a 10 cm-diameter dish. Three days later, the number of cells was determined and 5.0×10⁵ cells were again seeded in a 10 cm-diameter dish. The chicken cell line was collected 21, 42, 63, 84, 105 and 126 days after initiation of culturing, and the human cell clones were collected 10 and 20 days later. Chromosomal preparations were prepared.

(4) Chromosome Analysis

Detection of an artificial chromosome in chicken cells was performed by FISH analysis using a human specific probe Cot1 (Gibco BRL) in accordance with the method described in Matsubara et al. (FISH experimental protocol, Shujunsha, 1994). The presence or absence of a human chromosome was observed in 500 metaphase nuclei and a retention rate of the human chromosome was calculated. Detection of the artificial chromosome in human cells was performed by Giemsa staining in accordance with the method described in Kuroki et al. (Cell engineering handbook, Yodosha, 1992). The presence or absence of a mini chromosome was observed in 20 metaphase chromosome images and a retention rate of the mini chromosome was calculated. An average value of 4 clones was obtained. The results are shown in Table 1.

TABLE 1

Stability of #21ΔqHAC

| Host cell | Cell population doubling level | HAC retention rate (%) | |
|---|---|---|---|
| | | Non selectable by drug | Selectable by drug |
| DT40 | 118 | 99 | 100 |
| | 236 | 99 | 100 |
| HT1080 | 10 | 100 | 93 |
| | 22 | 97 | 98 |

A partial fragment of human chromosome 21 was stably retained in DT40 cells when cell division was performed in excess of 200 times under nonselective culture conditions. When the number of human chromosomes per cell was counted by observing 100 chromosome images during metaphase. A single chromosome was observed in all without exception. Although culturing of HT1080 cell clones were still continued, the partial fragment of human chromosome 21 was stably retained at the time point (the number of cell division: 22) under selective culture conditions. Furthermore, when a chromosome image during metaphase was observed, one or two chromosome portions per cell were observed.

From the experiments (3) and (4) above, it was clearly demonstrated that the partial fragment of human chromosome 21 devoid of a long-arm distal region is stably retained in a DT40 cell line and an HT1080 cell clone under nonselective culture conditions, and that the copy number per cell is maintained.

Example 5

Insertion of GFP Gene into HAC Vector Derived from Human Chromosome 21

Figure 8:
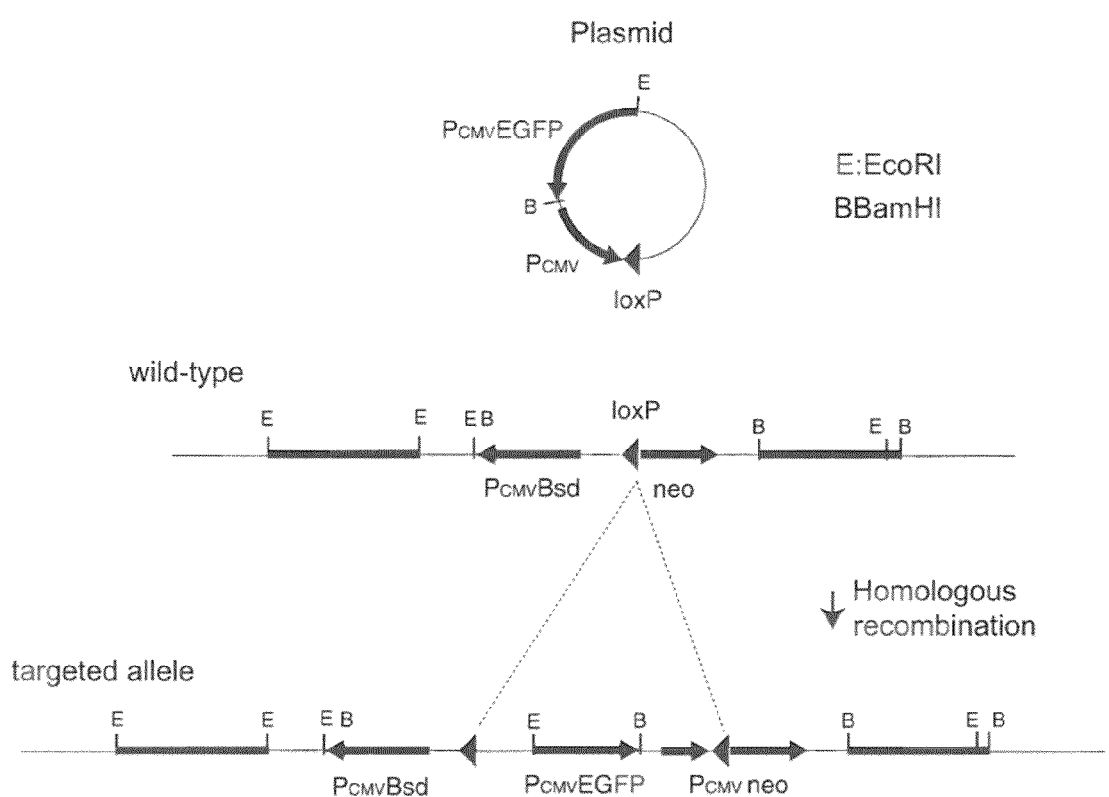
FIG. 8 is a schematic view showing the method of inserting in a site-specific manner a GFP construct into the loxP sequence in the proximal region of the long arm of human chromosome 21.

FIG. 8 shows a method of inserting a GFP gene into a HAC vector derived from human chromosome 21. As described in Examples 1 to 4, the HAC vector, which was derived from human chromosome 21, was prepared by deleting a long-arm distal region by telomere truncation, and introducing a loxP site into a long-arm proximal region. On the other hand, a GFP expression plasmid containing a loxP sequence was prepared. The plasmid was introduced into the artificial chromosome by use of the site-specific recombination reaction between the loxP sequences by transiently expressing Cre recombination enzyme. Recombinant products having the insert were screened based on whether G418 resistance was acquired or not (reconstitution of a neo gene expression unit by disruption of a promoter).

(1) Construction of GFP Expression Plasmid Containing loxP Sequence

A GFP expression vector PEGFP-C1 (Clontech) was digested with restriction enzyme GbLII and BamH I (Nippon Gene) to isolate/purify a 4.7 kb DNA fragment, which was self-ligated into a circular by use of DNA Ligation Kit Ver. 2 (Takara Shuzo Co., Ltd.). The recombinant plasmid was isolated by transformation of *Escherichia Coli* DH5α to obtain a plasmid PEGFP-C1Δ deficient in 51 bps of from GbL II to BamH I within the multicloning site. Using the PEGFP-C1Δ as a template, an EGFP gene expression unit was amplified by PCR.

The sequences of primer oligonucleotides prepared based on the nucleotide sequence obtained from the GenBank database (under accession No. U55763) are shown below:

```
                                    (SEQ ID No. 21)
EcoGFP5:    5'-GGCCGAATTCCGTATTACCGCCATGCAT;

(SEQ ID No. 22)
BamGFP3:    5'-CCGGGATCCCACAACTAGAATGCAGTG.
```

Both ends of the EGFP gene expression unit thus amplified were digested with restriction enzymes EcoR I and BamH I (Nippon Gene) to generate cohesive ends. The resultant construct was cloned into the EcoR I/BamH I site of a plasmid vector PBS226 (Lifetech) having a loxP sequence and a hCMV promoter.

(2) Transfection and Isolation of G418 Resistant Clone

CHO cells (CHO(#21)bsd79-1) retaining the HAC vector derived from human chromosome 21 prepared in Example 3 was treated with trypsin and 5×10⁶ cells were suspended in 0.8 ml of phosphate buffer (PBS). Electroporation was performed by use of Gene Pulser (Biorad) in the presence of 10 μg of PBS226/EGFP plasmid and 20 μg of Cre enzyme expression vector PBS185 (Lifetech). A voltage of 750V was applied to a condenser having a capacitance of 25 μF and allowed to discharge by use of an electroporation cell having electrodes placed at an interval of 4 mm. The electroporated cells were seeded in ten 100 mm plastic tissue-culture plates (Falcon) containing Eagle's F12 medium (hereinafter referred to as "F12", Invitrogen) supplemented with 10% fetus bovine serum (FBS). Two days later, the medium was replaced with a medium containing 800 μg/ml G418 (GENETICIN, Sigma) and 8 μg/ml Blasticidin S Hydrochloride (Funakoshi). Drug resistant colonies were formed in 2 to 3 weeks. The frequency of colony formation was 20 colonies per 5×10⁶ of CHO cells. The colonies were isolated, proliferated and subjected to the following analysis.

(3) Expression of GFP Gene Inserted in HAC Vector Derived from Human Chromosome 21

Figure 9:
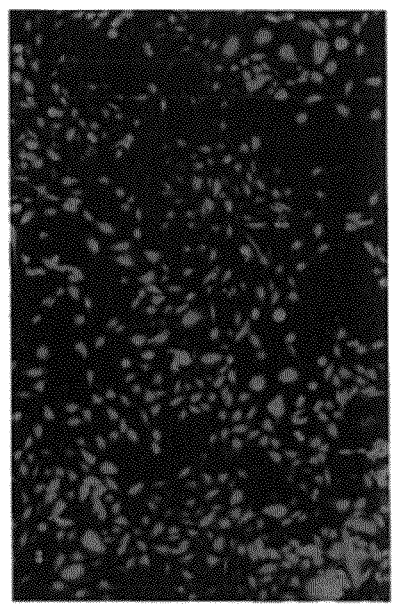
FIG. 9 is a fluorescence microscope photograph showing GFP expression in the G418 resistant CHO-K1 clone.

The isolated G418/blasticidin resistant CHO clone was subjected to observation by a fluorescent microscope. As a result, it was confirmed that GFP was expressed in 19 clones. A representative fluorescent image is shown in FIG. 9.

(4) Confirmation of Homologous Recombinant

Figure 10:
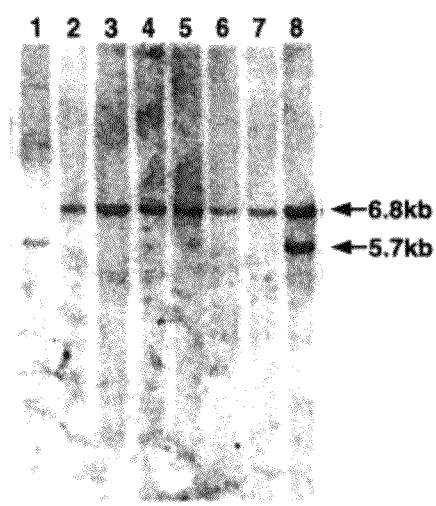
FIG. 10 is a photograph showing the results of southern blot analysis indicating the occurrence of site-specific recombination in a loxP sequence in the G418 resistant CHO-K1 clone.

Southern blot analysis was performed to confirm a homologous recombinant. In the southern blot, parts of a G418 resistant gene and a GFP gene were used as probes and about 5 μg genomic DNA treated with restriction enzyme EcoR I or BamH I (Nippon Gene) was used. As the GFP probe, an 849 bp fragment obtained by digesting plasmid PEGFP-C1 (Clontech) with restriction enzymes Nhe I and GbL II (Nippon Gene) was used. The G418 resistant gene probe was a 1000-bp fragment obtained by digesting plasmid pSV2neo with restriction enzymes GbL II and Sma I (Nippon Gene). The probes were labeled with $^{32}$P and the signal was detected by image analyzer BAS2000 (Fuji Photo Film Co., Ltd.). The representative results are shown in FIG. 10 by way of example. In FIG. 10, DNA digested with EcoR I was detected by a neo probe. Lane 1 shows a DT40 line before insertion. Lane 2 and the subsequent lanes show G418 resistant DT40 clones. In an allele before insertion, a signal derived from a 5.7 kb fragment was detected, whereas a signal derived from a 6.9 kb fragment was detected in alleles after insertion.

From the experiments (1) to (4) above, an allele obtained by homologous recombination was detected in 18 out of 19 G418 resistant clones analyzed. In 5 clones out of them, an allele before recombination was detected in addition to the alleles after homologous recombination, and a random insertion allele was detected in a single clone. Therefore, a desired recombinant was obtained with a frequency of 12/19 (63%).

Example 6

Deletion of the Short-Arm of Human Chromosome 21

(1) Construction of a Construct for Telomere Truncation

A telomere truncation vector for deleting a distal region of the short-arm of human chromosome 21 was constructed by altering PBS-TEL/Puro (Kuroiwa, Nucleic Acids Res., 26:3447, 1998). 1.7 kb expression unit for a puromycin resistant gene was removed from PBS-TEL/Puro, as a Not I fragment, and forming the blunt ends with T4 DNA Polymerase (DNA Blunting kit, Takara Shuzo Co., Ltd.) to produce PBS-TEF vector. PGKhygro/ALT20 was digested with restriction enzymes Cla I and Sma I (Nippon Gene) and an expression unit for a hygromycin resistant gene under the control of a PGK promoter was isolated/purified, as a 1.8 kb fragment. This fragment was cloned into the PBS-TEL vector to obtain PBS-TEL/Hygro.

Based on the nucleotide sequence (Accession No. AL163201) of the proximal region of the long-arm of human chromosome 21 obtained from the GenBank database, a target sequence for inserting a telomere truncation vector was designed. The sequences of primer oligonucleotides to which a recognition sequence for restriction enzyme Spe I or BamH I is added, for use in amplification of the target sequence, are shown below:

```
                                              (SEQ ID No. 23)
Spe31203:      5'-GCACTAGTCTGGCACTCCTGCATAAACA;

(SEQ ID No. 24)
Bam36192:      5'-CTAAGGATCCATTTCAGCCTGTGGGAATCA.
```

Figure 11:
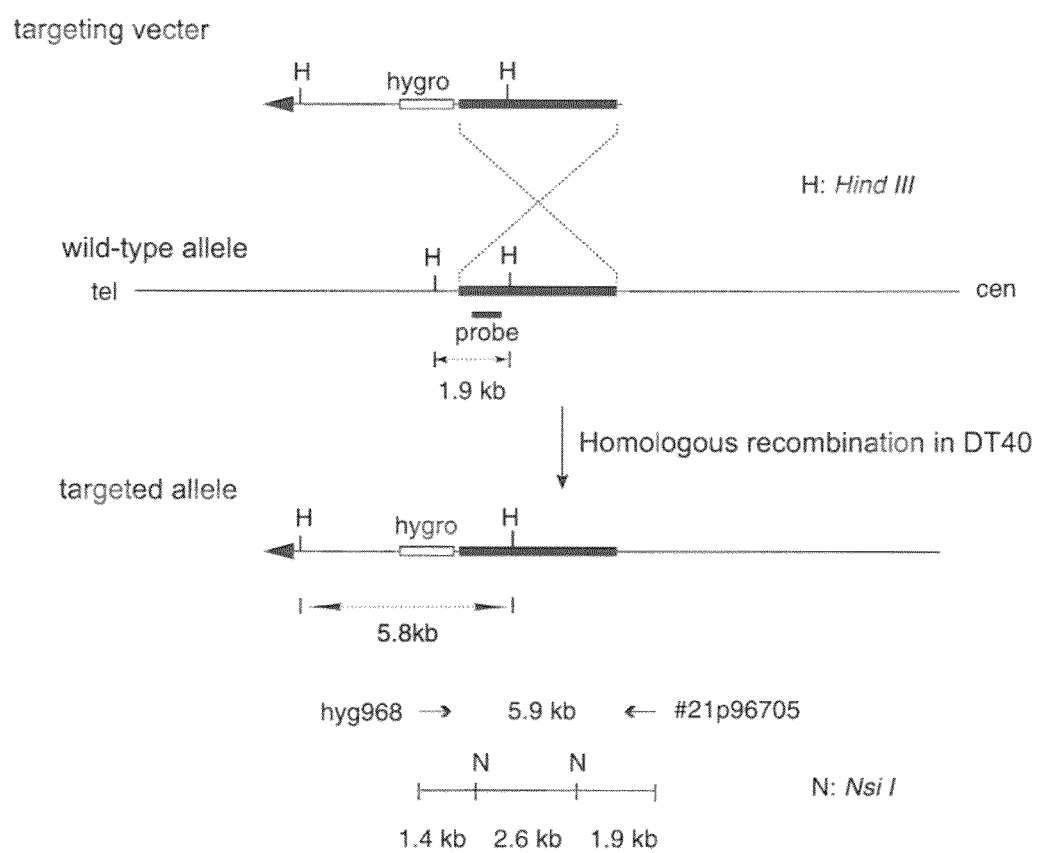
FIG. 11 is a schematic view of the method of deleting the distal region of the short arm of human chromosome 21 by telomere truncation.

The target sequence was amplified by PCR using as a template, the genomic DNA extracted from a DT40 hybrid cell retaining human chromosome 21. The amplified product was digested with restriction enzymes Spe I and BamH I (Nippon Gene). A DNA fragment of about 5 kb having cohesive ends was separated and purified by agarose gel electrophoresis. The DNA fragment was cloned into an Xba I/BamH I site of PBS-TEL/Hygro plasmid. The size of the PBS-TEL/Hygro construct finally obtained was about 5.8 kb. The telomere truncation vector, target sequence and chromosomal allele obtained by homologous recombination are shown in FIG. 11.

(2) Transfection and Isolation of a Hygromycin Resistant Clone

The PBS-TEL/Hygro construct was digested with restriction enzyme BamH I (Nippon Gene) to give a linear construct, which was introduced into DT40 hybrid cell (DT40(#21) bsd79) retaining human chromosome 21 where a long-arm distal region was deleted and a loxP site was inserted. The DT40 hybrid cells (1×10$^7$) were suspended in 0.75 ml of PBS and subjected to electroporation by Gene Pulser (Biorad) in the presence of 25 µg of DNA. A voltage of 750V was applied to a condenser having a capacitance of 25 µF and allowed to discharge by use of an electroporation cell having electrodes placed at an interval of 4 mm. The electroporated cells were suspended in DMEM medium (Invitrogen) supplemented with 10% fetus bovine serum (FBS), 1% chicken serum (ChS) and 50 µM 2-mercaptoethanol and seeded in five 96-well clusters (Falcon). Two days later, Hygromycin-B (Wako Pure Chemical Industries, Ltd.) was added so as to have a final concentration of 1.5 mg/ml. In 2 to 3 weeks, resistant colonies were formed. Transfection was carried out twice to isolate 63 drug resistant colonies in total. The colonies were proliferated and subjected to the following analysis.

Figure 12:
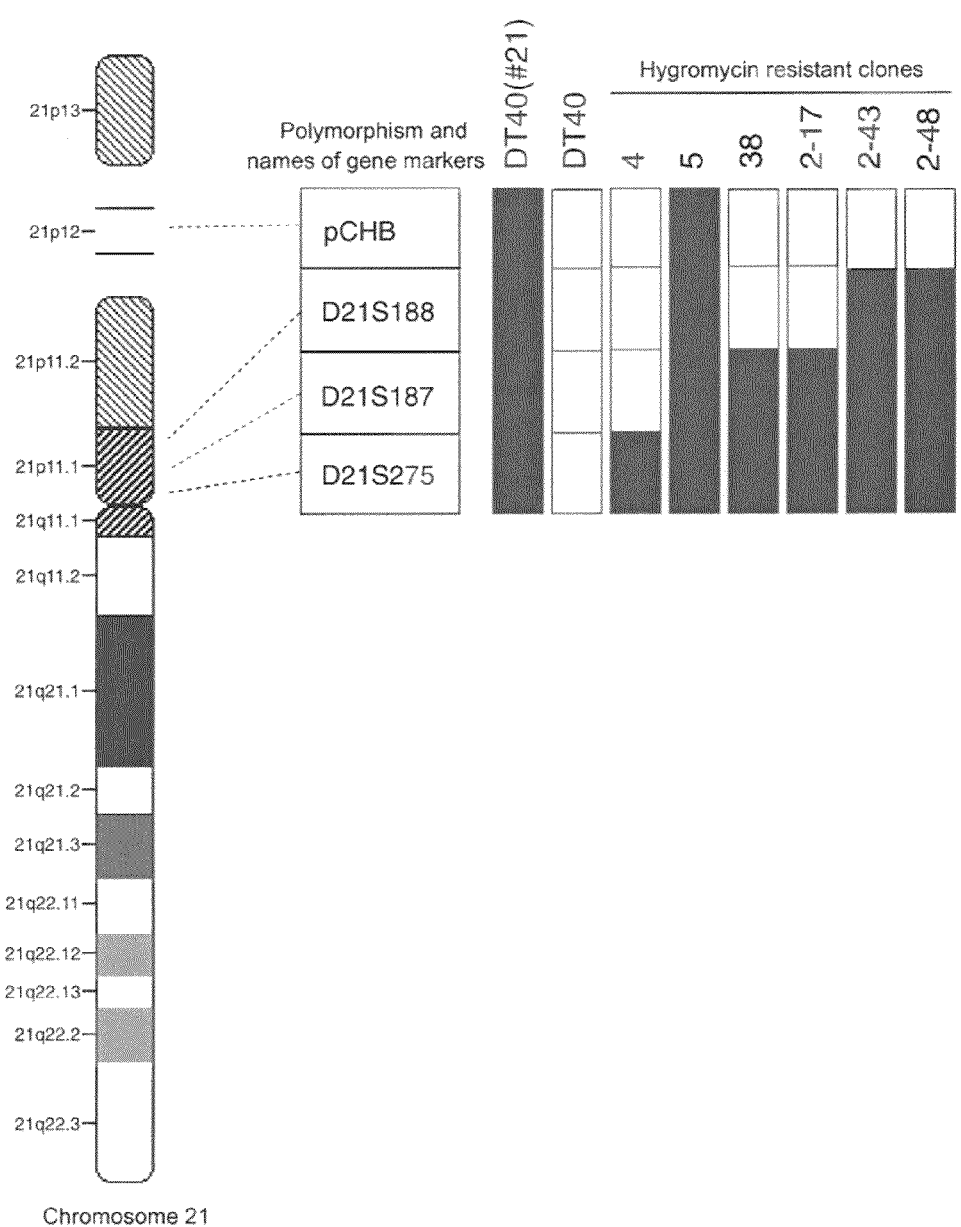
FIG. 12 shows the results of PCR analysis indicating the deletion of the distal region of the short arm of human chromosome 21 in the hygromycin resistant DT40 clone.

(3) Screening of Homologous Recombinant and Confirmation of Telomere Truncation (3-1) PCR Analysis PCR analysis was performed for a primary screening for a homologous recombinant from hygromycin resistant DT40 clones. Using about 0.1 µg of the genomic DNA extracted from hygromycin resistant clones as a template, STS markers (pCHB, D21S188, D215275) located in a short-arm proximal region of human chromosome 21 were amplified. The representative results are shown in FIG. 12. In FIG. 12, a schematic chromosome map based on a G band image of human chromosome 21 is given at the left side. In addition, it is shown which marker is present in which band. With respect to hygromycin resistant DT40 clone, a marker whose expected PCR amplification product was detected, is indicated by a solid square, and the marker whose expected PCR amplification product was not detected is indicated by an open square. DT40 (#21) represents a cell before subjected to telomere truncation. In the case where a short-arm distal region was deleted by telomere truncation, it was conceivable that D21S275 might be present but D21S188 and pCHB might not be present. Therefore, 45 clones where either D21S188 or pCHB was not amplified were selected and subjected to Southern Blot analysis.

(3-2) Southern Blot Analysis

A probe was designed within a target sequence for homologous recombination. As the probes, the pair of oligonucleotide primers shown below were used. PCR was performed by using genomic DNA from a DT40 hybrid cell retaining human chromosome 21, as a template. A PCR amplification product was isolated and purified.

```
                                              (SEQ ID No. 25)
21p91203:     5'-CTGGCACTCCTGCATAAACA (SEQ ID No. 26)
21p91976:     5'-TCTGTGTTCCCCTTCTCTGA
```

Figure 13:
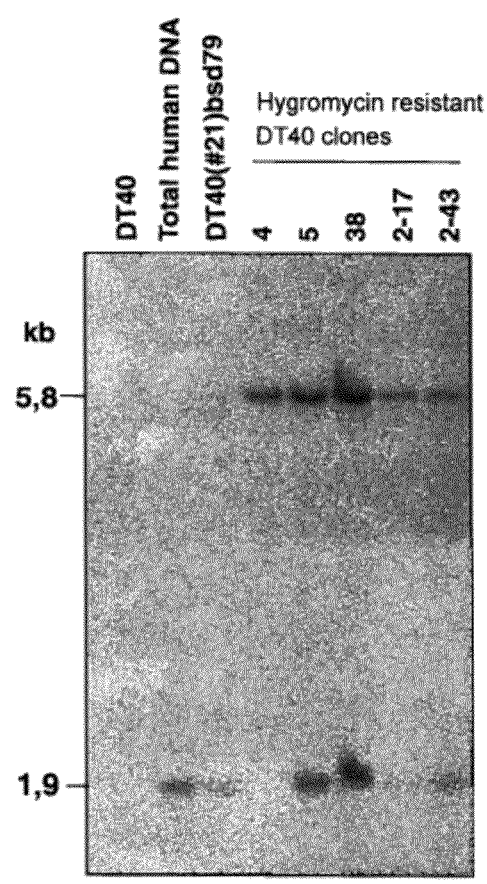
FIG. 13 is a photograph showing the results of southern blot analysis indicating the deletion of the distal region of the short arm in the hygromycin resistant DT40 clone, or the introduction of an artificial telomere sequence in a site-specific manner.

About 10 µg of the genomic DNA extracted from a hygromycin resistant clone was digested with restriction enzyme Hind III (Nippon Gene) and subjected to Southern blot analysis. The length of a restriction fragment was predicted based on a nucleotide sequence. In the case of a homologous recombinant, the length was 5.8 kb, and in the case of a wild type (non-homologous recombinant), the length was 1.9 kb. It was confirmed that 2 out of the 45 candidate clones screened in the primary screening were homologous recombinants (FIG. 13).

(3-3) PCR Method

Sequences flanking with the recombination target sequence were amplified by PCR. The sequences of primer oligonucleotides, which were designed on human chromosome 21 and on a targeting vector, are shown below:

```
                                    (SEQ ID No. 27)
Hyg968:        5'-AAGTACTCGCCGATAGTGGAAACC;

(SEQ ID No. 28)
#21p96705:     5'-AGTTAGCCTACCTTTTGGCCATCC.
```

Figure 14:
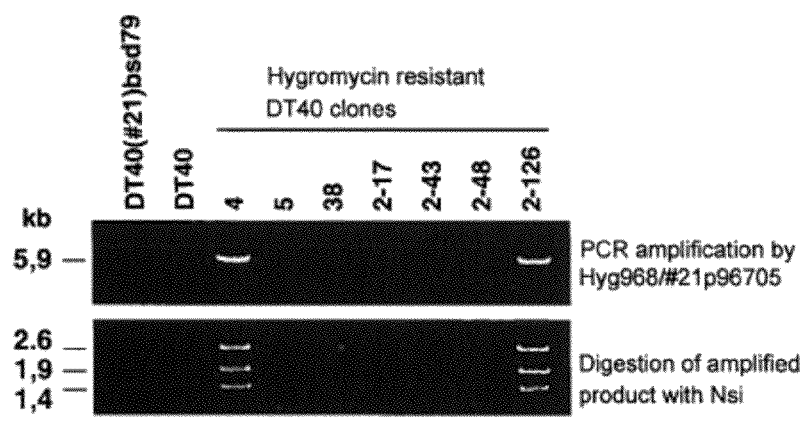
FIG. 14 is a photograph showing the results of PCR analysis indicating the deletion of the distal region of the short arm in the hygromycin resistant DT40 clone, or the introduction of an artificial telomere sequence in a site-specific manner.

The size of an amplified product was 5.9 kb. It was predicted that digestion of the amplified product with restriction enzyme Nsi I might produce fragments of 1.4 kb, 2.6 kb, and 1.9 kb (FIG. 11). PCR amplification was confirmed to occur in 2 clones where a homologous recombination allele was observed in Southern blot analysis, and generation of partial fragments digested with the restriction enzyme was confirmed (FIG. 14).

(3-4) Fluorescence in situ Hybridization (FISH)

Figure 15:
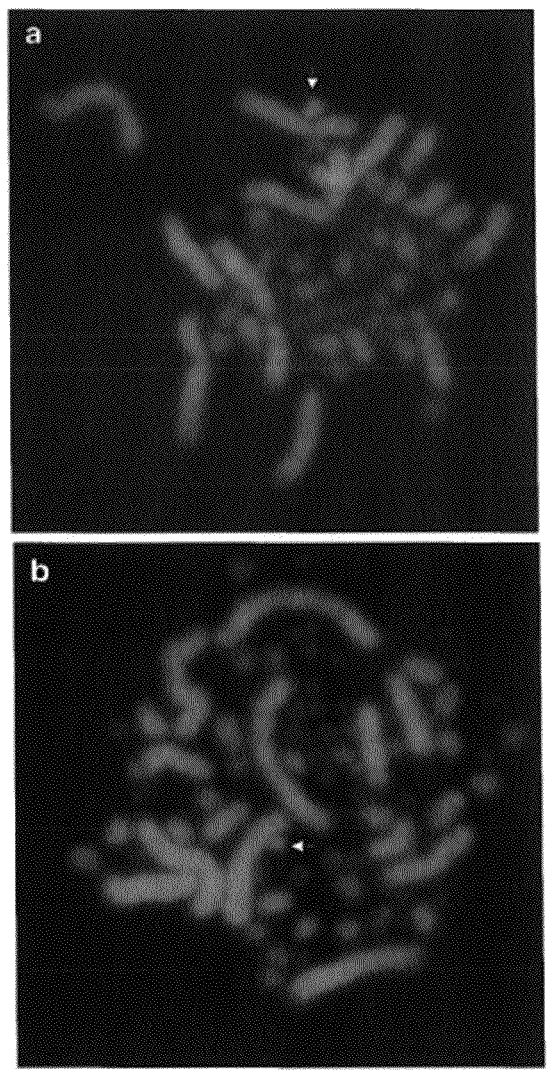
FIGS. 15a and 15b are photographs showing the results of FISH analysis indicating the deletion of the distal region of the short arm in the hygromycin resistant DT40 clone.

FISH analysis was performed using a human specific probe Cot1 (Gibco BRL) in accordance with the method described in Matsubara et al. (FISH experimental protocol, Shujunsha, 1994). As a result, truncated human chromosome 21 was detected in almost all the mitotic images observed (FIGS. 15a and 15b).

From the experiments (1) to (3) above, it was confirmed that 2 out of hygromycin resistant 63 clones obtained retain truncated human chromosome 21 by deletion of a short-arm.

Example 7

Insertion of EPO Gene into HAC Vector Derived from Human Chromosome 21

The human EPO gene was inserted into a HAC vector derived form human chromosome 21 in the same manner as in the case of a GFP gene described in Example 5. As described in Examples 1 to 4, the HAC vector derived from human chromosome 21 was prepared by deleting a long-arm distal region by telomere truncation and introducing a loxP site into a long-arm proximal region. On the other hand, a human EPO expression plasmid containing a loxP sequence was prepared. The plasmid was integrated into the artificial chromosome by use of the site-specific recombination reaction between the loxP sequences by transiently expressing Cre recombination enzyme. Recombinant products having the insert were screened based on whether G418 resistance was acquired or not (reconstitution of a neo gene expression unit by disruption of a promoter).

(1) The Sequences of Primer Oligonucleotides Used in Constructing Human EPO Expression Plasmid pLN1-EPO Containing a loxP Sequence will be Shown Below:

```
SV40polyANp1:
                                    (SEQ ID No. 29)
5'-CGG GAT CCC TCG AGC GAG ACA TGA TAA GAT ACA
TTG ATG-3';

SV40polyARp1:
                                    (SEQ ID No. 30)
5'-GGA AGA TCT TCC TAA TCA GCC ATA CCA CAT TTG
TAG AGG-3',
``` these primers were prepared based on the nucleotide sequences of plasmid vector pSTneoB (Kato et al., Cell Struct Funct, 12:575-580, 1987);

```
CMVNp3:
                                    (SEQ ID No. 31)
5'-CGG AAT TCC GGA CAT TGA TTA TTG ACT AGT TAT
TAA TAG-3';

CMVRp1:
                                    (SEQ ID No. 32)
5'-CGG GAT CCC GGG TGT CTT CTA TGG AGG TCA AAA
CAG-3',
``` these primers were prepared based on the nucleotide sequence of CMV promoter of pBS226; and

```
hEPONp1:
                                    (SEQ ID No. 33)
5'-CGG GAT CCC GGC CAC CAT GGG GGT GCA CGA ATG
TC-3';

hEPORp1:
                                    (SEQ ID No. 34)
5'-CGC TCG AGC GCT ATC TGT CCC CTG TCC TGC AGG-3',
``` these primers were prepared based on the nucleotide sequence obtained from the GenBank (Accession No. I05397).

Both ends of the SV40 polyA additional unit, which was amplified by PCR using pSTneoB as a template and SV40polyANp1 (SEQ ID No. 29) and SV40polyARp1 (SEQ ID No. 30), were digested with restriction enzymes BamH I and Bgl II (Takara Shuzo Co., Ltd.) to obtain cohesive ends. The resultant construct was cloned into the BamH I site of plasmid vector pBS226 (Lifetech) having a loxP sequence and an hCMV promoter. This was designated as pBS226-pA.

Subsequently, both ends of the CMV promoter unit, which was amplified by PCR using pBS226 as a template and CMVNp3 (SEQ ID No. 31) and CMVRp1 (SEQ ID No. 32), were digested with restriction enzymes EcoR I and BamH I (Takara Shuzo Co., Ltd.) to obtain cohesive ends. The resultant construct was cloned into the EcoR I-BamH I site of pBS226-pA. This was designated as pLN1.

Finally, both ends of the human EPO coding region, which was amplified by PCR using human EPO cDNA as a template and hEPONp1 (SEQ ID No. 33) and hEPORp1 (SEQ ID No. 34), were digested with restriction enzymes BamH I and Xho I (Takara Shuzo Co., Ltd.) to obtain cohesive ends. The resultant construct was cloned into the BamH I-Xho I site of pLN1. This was designated as pLN1-EPO.

(2) Transfection and Isolation of G418 Resistant Clone

The CHO cell (CHO(#21)bsd79-1) retaining a HAC vector derived from human chromosome 21 prepared in Example 3 was treated with trypsin and $5 \times 10^6$ cells were suspended in 0.8 ml of Hank's balanced salt solution (HBSS) and subjected to electroporation using Gene Pulser (Biorad) in the presence of 10 µg of pLN1-EPO vector prepared in Section (1) above, and 10 µg of Cre enzyme expression vector pBS185 (Lifetech). A voltage of 450V was applied to a condenser having a capacitance of 500 µF and allowed to discharge by use of an electroporation cell having electrodes placed at an interval of 4 mm. The electroporated cells were seeded in four 48-well plastic tissue-culture plates (Falcon) containing Eagle's F12 medium (hereinafter referred to as "F12"; Invitrogen) supplemented with 10% fetus bovine serum (FBS). Two days later, the medium was replaced with a medium containing 800 μg/ml G418 (GENETICIN, Invitrogen) and 8 μg/ml Blasticidin S Hydrochloride (Funakoshi). Resistant colonies were formed in 2 to 3 weeks. The frequency of colony formation was 28 colonies in average per $5 \times 10^6$ CHO cells. Colonies were isolated, proliferated, and subjected to the following analysis. The cells thus obtained will be hereinafter referred to as "KH21E" cells.

(3) Expression of EPO Gene Inserted in HAC Vector Derived form Human Chromosome 21

Expression of the human EPO gene was determined by quantifying human EPO protein produced in the culture supernatant in accordance with the enzyme-linked immunosorbent assay (ELISA).

With respect to 6 out of 19 clones of G418/blasticidin resistant KH21E cell isolated, $1 \times 10^5$ cells for each were seeded in a 6-well plastic tissue-culture plate (Falcon) containing 2 ml of F12 medium supplemented with 10% FBS and containing 800 μg/ml G418 and 8 μg/ml blasticidin. After the cells reached confluence, the medium was replaced with 2 ml of F12 medium supplemented with 10% FBS. Culturing was performed for 6 days and the supernatant was recovered. The amount of human EPO contained in the culture supernatant was quantified by a human EPO ELISA kit (Quantikine IVD Human EPO Immunoassay, R&D system). The results are shown in Table 2.

TABLE 2

| Clone No. | Measurement value (mIU/ml) | Concentration of EPO in CM | |
|---|---|---|---|
| | | (IU/ml) | (μg/ml) |
| C13 | 16.4 | 1640 | 8.2 |
| C15 | 17.1 | 1710 | 8.5 |
| C17 | 29.5 | 2950 | 14.7 |
| C18 | 41.1 | 4110 | 20.5 |
| C21 | 16.6 | 1660 | 8.3 |
| C22 | 23.9 | 2390 | 11.9 |

From the results above, it was confirmed that human EPO is expressed in all of the 6 clones.

(4) Biological Activity of Human EPO Produced by KH21E Cells

The biological activity of the human EPO produced was analyzed based on proliferation activity of a human leukemia cell line, UT7-EPO cells (obtained from Prof. Norio Komatsu, Jichi Medical School), which proliferate in a human EPO-dependent manner. With respect to two KH21E cell clones (#C2 and #C18), the culture supernatant was added to IMDM medium (Invitrogen) supplemented with 10% FBS so as to make final concentrations of 0.01, 0.1, 1, 5, 20, and 100 mIU/ml EPO based on the quantification values of Table 2. To a 96-well plastic tissue-culture plates (Falcon) containing 0.1 ml of such IMDM mediums, $5 \times 10^3$ cells of UT7-EPO cells were seeded. After culturing was performed for 3 days, cell proliferation was analyzed by a cell proliferation determination kit (Cell Titer 96 AQueous One Solution Cell Proliferation Assay, Promega).

Figure 16:
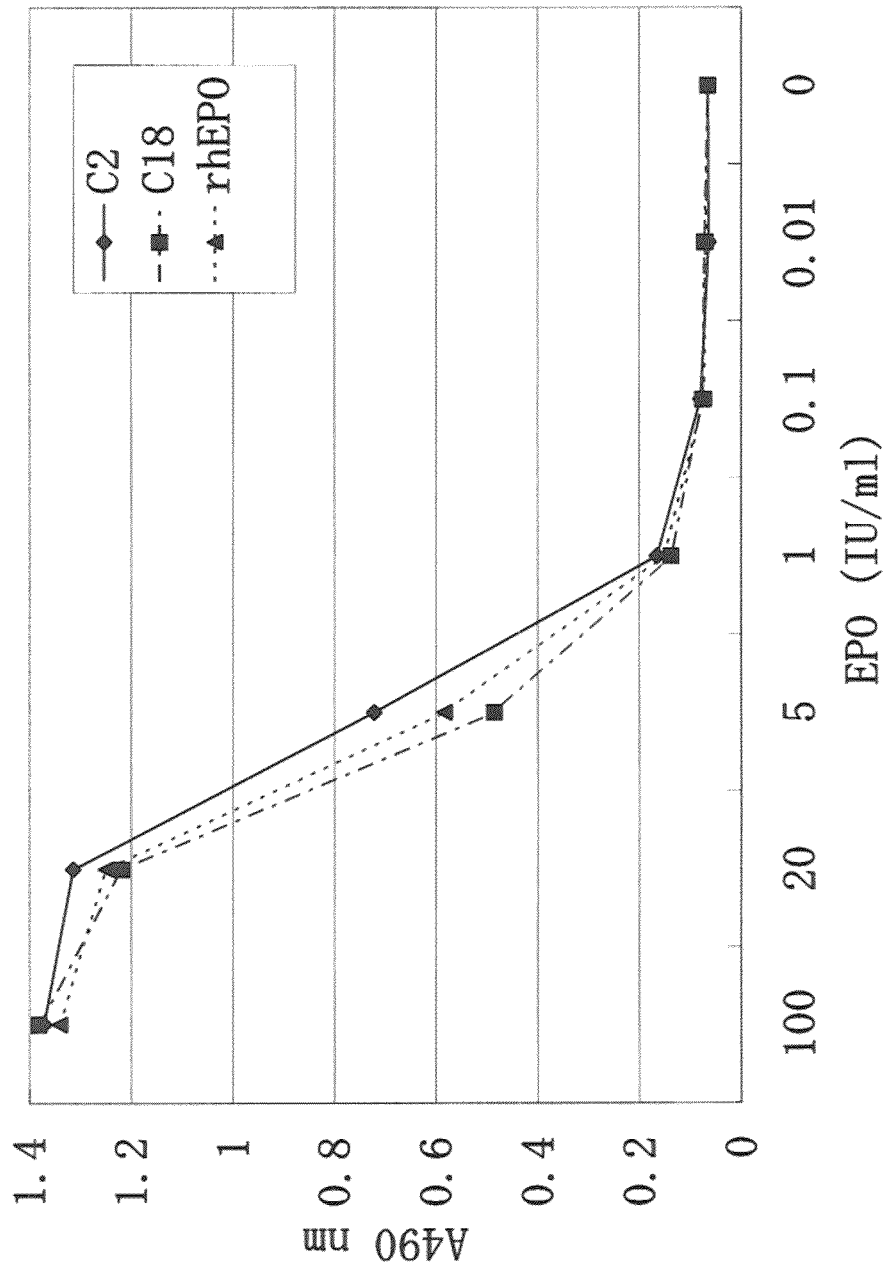
FIG. 16 shows the result that human EPO produced in the supernatant of KH21E cell culture had cell proliferation activity similar to that the recombinant human EPO protein (rhEPO) had.

The results are shown in FIG. 16. In each of two cases where the culture supernatants of 2 clones were added, the absorbance was observed to increase in a dose dependent manner (FIG. 16, C2 and C8) similarly to the case where recombinant human EPO protein was added (rhEPO; Kirin brewery Co., Ltd.).

From the results above, it was confirmed that human EPO produced in the culture supernatant has the same biological activity as that of recombinant human EPO protein.

Example 8

Confirmation of Transferred Chromosome in KH21E Cell

In this Example, whether a chromosome was transferred or not was confirmed in each of the KH21E cell clones prepared in Example 7 (2) by PCR and FISH analysis.

(1) PCR Analysis

PCR amplification was performed with respect to marker PRED 65 and PRED3 genes which were located in a long-arm proximal region of human chromosome 21 and in the vicinity of a loxP site, and D21S265 marker located in a distal region thereof (see, Example 1, (3) and FIG. 2). It was predicted that the human EPO gene insert introduced by site-specific recombination between loxP sequences might have the PRED 65 and PRED 3 genes but not have the D21S265 marker. As a result, in 21 out of 22 clones of the G418 resistant CHO cell, the expected amplification product was obtained. For the 21 clones, STS markers (pCHB, D21S187, D21S275) positioned in a short-arm proximal region of human chromosome 21 were amplified by PCR (see Example 6, (3), FIG. 12). Since the short-arm of the HAC vector derived from human chromosome 21 was allowed to leave, it was conceivable that all markers might be present. As a result, it was confirmed that amplification was performed as predicted in 15 clones.

(2) Fluorescence in situ Hybridization (FISH) Analysis

FISH analysis was performed using a human specific probe Cot1 (Gibco BRL) in accordance with the method described in Matsubara et al. (FISH experimental protocol, Shujunsha, 1994). When analysis was performed with respect to 8 clones out of those in which all markers were amplified as predicted in PCR analysis of Section (1) above, truncated human chromosome 21 was detected in all the mitotic images observed. The results are shown in Table 3. Please note that clone KH21 listed in Table 3 represents a CHO cell (CHO(#21)bsd79-1) retaining the HAC vector derived from human chromosome 21 prepared in Example 3.

TABLE 3

| Name of clone | Number of analyzed samples mitotic image/metaphase nucleus | Number of Cot-1 signals per cell mitotic image/metaphase nucleus | | | | | Retention rate (metaphase nucleus) % |
|---|---|---|---|---|---|---|---|
| | | 0 | 1 | 2 | 3 | 4=< | |
| KH21 | 50/100 | 6/12 | 43/87 | 0/1 | 0/0 | 0/0 | 88 |
| C1 | 18/50 | 0/2 | 18/40 | 0/7 | 0 | 0/1 | 96 |
| C2 | 50/100 | 4/4 | 45/96 | 0/0 | 0/0 | 0/0 | 96 |
| C3 | 20/50 | 4/2 | 16/43 | 0/5 | 0 | 0 | 96 |
| C4 | 50/100 | 0/1 | 12/37 | 37/58 | 0/3 | 0/1 | 99 |

TABLE 3-continued

| Name of clone | Number of analyzed samples mitotic image/ metaphase nucleus | Number of Cot-1 signals per cell mitotic image/metaphase nucleus | | | | Retention rate (metaphase nucleus) % |
|---|---|---|---|---|---|---|
| | | 0 | 1 | 2 | 3 | 4=< | |
| C11 | 50/100 | 4/2 | 40/85 | 6/13 | 0/0 | 0/0 | 98 |
| C12 | 50/100 | 2/2 | 12/36 | 33/58 | 3/2 | 0/2 | 98 |
| C13 | 50/100 | 0/1 | 13/35 | 32/58 | 0/2 | 5/4 | 99 |
| C18 | 17/41 | 1/0 | 6/14 | 10/25 | 0 | 0/2 | 100 |

From the results above, it was confirmed that truncated human chromosome 21 was transferred into the CHO cell, based on relative comparison with the chromosome of the host CHO cell in size.

From the experiments (1) and (2) above, it was confirmed that the G418 resistant CHO clone (KH21E cell) obtained retains truncated human chromosome 21 devoid of a long-arm distal region thereof.

Example 9

Insertion of a Plurality of EPO Genes into HAC Vector Derived from Human Chromosome 21

In this Example, a plurality of human EPO genes were inserted into a HAC vector derived from human chromosome 21 in the same manner as in the case of a human EPO gene described in Example 7. As described in Examples 1 to 4, a HAC vector derived from human chromosome 21 was prepared by deleting a long-arm distal region by telomere truncation and introducing a loxP site in the long-arm proximal region thereto. On the other hand, a human EPO expression plasmid containing a loxP sequence was prepared. The plasmid was introduced into the artificial chromosome by use of the site-specific recombination reaction between the loxP sequences by transiently expressing Cre recombination enzyme. Recombinant products having the insert were screened based on whether G418 resistance was acquired or not (reconstitution of a neo gene expression unit by disruption of a promoter).

(1) Construction of a Plasmid Expressing 2 Copies of EPO containing loxP Sequence (pLN1-EPO2)

The sequences of primer oligonucleotides used in plasmid construction are shown below:

```
EPOnF:
                              (SEQ ID No. 35)
5'-GGA ATT CCG GGC CCA CGC GTG ACA TTG ATT ATT
GA-3';

SVpAR:
                              (SEQ ID No. 36)
5'-GGA ATT CCT GAT CAT AAT CAG CCA TAC CAC ATT
TG-3'.
```

EPOnF primer (SEQ ID No. 35) had EcoR I, Apa I, Mlu I restriction enzyme recognition sequences and a 5'-side partial sequence of CMV promoter sequentially from the 5' side, and prepared based on the nucleotide sequence of CMV promoter in pBS226. SVpAR primer (SEQ ID No. 36) had EcoR I, Bcl I restriction enzyme recognition sequences and a 3'-side partial complementary sequence of SV40 polyA additional unit sequentially from the 5' side, and prepared based on plasmid vector pSTneoB (Kato et al., Cell Struct Funct, 12: 575-580, 1987).

Using a DNA fragment containing CMV promoter, which was obtained by digesting plasmid vector pLN1-EPO prepared in Example 7 with EcoR I and Xba I (Takara Shuzo Co., Ltd.), the human EPO gene, and SV40 polyA additional unit, as a template, PCR amplification was performed by use of EPOnF (SEQ ID No. 35) and SVpAR primers (SEQ ID No. 36) with KOD-Plus-(Toyobo). As a thermal cycler, Gene-Amp9700 (Applied Biosystems) was used. A PCR cycle comprises a reaction at 94° C. for 2 minutes, and 30 cycles of denaturation at 94° C. for 15 seconds, annealing at 60° C. for 30 seconds, and extension at 68° C. for 90 seconds. Both ends of the obtained DNA fragment were digested with restriction enzyme EcoR I (Takara Shuzo Co., Ltd.) to obtain cohesive ends. The resultant construct was cloned into the EcoR I site of a plasmid vector pLN1-EPO. The nucleotide sequence of the DNA fragment insert thus cloned was analyzed by a DNA sequencer (PRISM 3700, Applied Biosystems) and confirmed to be identical to the corresponding portion of the nucleotide sequence of the pLN1-EPO used as a template. Of the clones thus obtained, a clone having 2 copies of the insert consisting of CMV promoter, human EPO gene, and SV40 polyA additional unit, in forward direction, was designated as a plasmid vector pLN1-EPO2.

(2) Construction of a Plasmid Expressing 4 Copies of EPO containing loxP Sequence (pLN1-EPO4)

Plasmid vector pLN1-EPO2 prepared in the Section (1) above was digested with Xba I (Takara Shuzo Co., Ltd.) to give a linear vector, and then treated with KOD polymerase (Toyobo) to generate the blunt ends. Thereafter, the linear fragment was digested with Apa I (Takara Shuzo Co., Ltd.) to obtain a DNA fragment for use in insertion containing 2 copies of a fragment consisting of CMV promoter, human EPO gene, and SV40 polyA additional unit. Plasmid vector pLN1-EPO2 was digested with Mlu I (Takara Shuzo Co., Ltd.), and then treated with KOD polymerase (Toyobo) to generate the blunt ends. The fragment was digested with Apa I (Takara Shuzo Co., Ltd.) to obtain an Apa I-blunt ended Mlu I site. To this site, the DNA fragment for use in insertion obtained above was cloned. The obtained plasmid vector containing 4 copies of the human EPO gene was designated as pLN1-EPO4.

(3) Transfection and Isolation of G418 Resistant Clone

The CHO cells (CHO(#21)bsd79-1) retaining a HAC vector derived from human chromosome 21 and prepared in Example 3 were treated with trypsin and $5 \times 10^6$ cells were suspended in 0.8 ml of Hank's balanced salt solution (HBSS). Electroporation was performed by use of Gene Pulser (Biorad) in the presence of 10 μg of the pLN1-EPO2 vector or the pLN1-EPO4 vector prepared in the Section (1) or (2) above and 10 μg of Cre enzyme expression vector pBS185 (Lifetech). A voltage of 450V was applied to a condenser having a capacitance of 500 μF and allowed to discharge by use of an electroporation cell having electrodes placed at an interval of 4 mm. The electroporated cells were seeded in five 48-well plastic tissue-culture plates (Falcon) containing Eagle's F12 medium (hereinafter referred to as "F12"; Invitrogen) supplemented with 10% fetus bovine serum (FBS). Two days later, the medium was replaced with a medium containing 800 μg/ml G418 (GENETICIN, Invitrogen) and 8 μg/ml Blasticidin S Hydrochloride (Funakoshi). Resistant colonies were formed in 2 to 3 weeks. The frequency of colony formation was 14 colonies per $5 \times 10^6$ CHO cells in the case of pLN1-EPO2 and 24 colonies in the case of pLN1-EPO4. Colonies were isolated, proliferated and subjected to the following analysis. The cells prepared by use of pLN1-EPO2 will be hereinafter referred to as "KH21E2 cells" and the cells prepared by use of pLN1-EPO4 as "KH21E4 cells".

(4) Confirmation of Human EPO Recombinant Insert

Screening of a recombinant having the insert, that is, whether or not the insert was introduced into the loxP sequence site on a HAC vector derived from human chromosome 21, was confirmed by PCR amplification using primers that were designed on the sequence derived from the human EPO gene donor vector and on the HAC vector so as to flank the loxP sequence site. The copy number of human EPO gene inserts was confirmed by PCR amplification using primers that were designed on plasmid vector pBS226 and the HAC vector.

The sequences of oligonucleotide primers used in the PCR amplification are shown below:

```
SVpANp1:
                               (SEQ ID No. 37)
5'-TTT GCA TGT CTT TAG TTC TAT GAT GA-3',
``` this primer was prepared based on the nucleotide sequence of plasmid vector pSTneoB (Kato et al., Cell Struct Funct, 12:575-580, 1987);

```
                               (SEQ ID No. 38)
Neo Rp2:  5'-AGG TCG GTC TTG ACA AAA AGA AC-3',
``` this primer was prepared based on the nucleotide sequence of a neo gene of plasmid vector pSF1(Lifetech);

```
                               (SEQ ID No. 39)
M13RV:    5'-CAG GAA ACA GCT ATG AC-3',
``` this primer was prepared based on the nucleotide sequence of plasmid vector pBS226 (Lifetech).

PCR amplification was performed by using SVpANp1 primer (SEQ ID No. 37) designed in an SV40 poly A additional sequence region derived from pLN1-EPO2 or pLN1-EPO4 vector, and Neo Rp2 primer (SEQ ID No. 38) designed in a neomycin resistant gene derived from pSF1 on the HAC vector. In the case of a recombinant having an insert, it was predicted to obtain about 1.0 kbp fragment including a region from a portion having SV40 poly A additional sequence to a loxP sequence derived from pLN1-EPO2 or pLN1-EPO4 vector, and a region from the loxP sequence to a part of the neo gene derived from pSF1. As a result, amplification was performed as predicted in all of the 6 KH21E2 cell clones and the 6 KH21E4 cell clones.

From the above, it was confirmed that all of the 12 clones are recombinants having the inserts introduced into the loxP sequence.

Next, PCR amplification was performed with respect to the 6 KH21E2 cell clones by using Neo Rp2 primer (SEQ ID No. 38) and M13RV (SEQ ID No. 39) derived from plasmid vector pBS226. In the case of a recombinant having an insert, it was predicted to obtain about 3.8 kbp fragment including a region from 2 copies of a portion having the CMV promoter, the human EPO gene, and the SV40 poly A additional sequence, to a loxP sequence derived from pLN1-EPO2, and a region from the loxP sequence to a part of the neo gene derived from pSF1. As a result, amplification was performed as predicted in all of the clones.

From the above, it was confirmed that the 6 KH21E2 cell clones contain 2 copies of the DNA insert including CVM promoter, human EPO gene and SV40 polyA additional sequence.

(5) Expression of EPO Gene Inserted in HAC Vector Derived from Human Chromosome 21

Expression of the human EPO gene was determined by quantifying human EPO protein produced in the culture supernatant in accordance with the enzyme-linked immunosorbent assay (ELISA).

(5-1) Expression of the EPO Gene in KH21E2 Cell

With respect to 6 out of isolated 14 clones of G418/blasticidin resistant KH21E2 cell, $1 \times 10^5$ cells for each were seeded in a 6-well plastic tissue-culture plate (Falcon) containing 2 ml of F12 medium, supplemented with 10% FBS and containing 800 μg/ml G418 and 8 μg/ml blasticidin. After the cells reached confluence, the medium was replaced with 2 ml of F12 medium supplemented with 10% FBS. Culturing was performed for 6 days and the supernatant was recovered. The amount of human EPO contained in the culture supernatant was quantified in a $2 \times 10^{-5}$ dilution by a human EPO ELISA kit (Quantikine IVD Human EPO Immunoassay, R&D system). The results are shown in Table 4.

TABLE 4

| Clone No. | Measurement value (mIU/ml) | Concentration of EPO in CM | |
|---|---|---|---|
| | | (IU/ml) | (μg/ml) |
| C1 | 29 | 1450 | 7.2 |
| C7 | 40 | 2000 | 10.0 |
| C10 | 27 | 1350 | 6.7 |
| C11 | 42 | 2100 | 10.5 |
| C13 | 25 | 1250 | 6.2 |
| C14 | 39 | 1950 | 9.7 |
| Average | 33 | 1683 | 8.3 |
| Standard deviation | 7.4 | 373 | 1.8 |

(5-2) Expression of the EPO Gene in KH21E4 Cell

With respect to the 6 out of isolated 24 clones of G418/blasticidin resistant KH21E4 cell, $1 \times 10^5$ cells for each were seeded in a 6-well plastic tissue-culture plate (Falcon) containing 2 ml of F12 medium supplemented with 10% FBS and containing 800 μg/ml G418 and 8 μg/ml blasticidin. After the cells reached confluence, the medium was replaced with 2 ml of F12 medium supplemented with 10% FBS. Culturing was performed for 6 days and the supernatant was recovered. The amount of human EPO contained in the culture supernatant was quantified in a $2 \times 10^{-5}$ dilution by a human EPO ELISA kit (Quantikine IVD Human EPO Immunoassay, R&D system). The results are shown in Table 5.

TABLE 5

| Clone No. | Measurement value (mIU/ml) | Concentration of EPO in CM | |
|---|---|---|---|
| | | (IU/ml) | (μg/ml) |
| C3 | 45 | 2250 | 11.2 |
| C8 | 52 | 2600 | 13.0 |
| C10 | 67 | 3350 | 16.7 |

TABLE 5-continued

| Clone No. | Measurement value (mIU/ml) | Concentration of EPO in CM (IU/ml) | (µg/ml) |
|---|---|---|---|
| C13 | 45 | 2250 | 11.2 |
| C14 | 50 | 2500 | 12.5 |
| C16 | 48 | 2400 | 12.0 |
| Average | 51 | 2558 | 12.7 |
| Standard deviation | 8.2 | 411 | 2.0 |

(5-3) Expression of the EPO Gene in KH21E Cell

Five clones of G418/blasticidin resistant KH21E cell having a single copy of the human EPO gene on the HAC vector derived from human chromosome 21 and isolated in Example 7 were used as a reference. With respect to the 5 clones, $1 \times 10^5$ cells for each were seeded in a 6-well plastic tissue-culture plate (Falcon) containing 2 ml of F12 medium supplemented with 10% FBS and containing 800 µg/ml G418 and 8 µg/ml blasticidin. After the cells reached confluence, the medium was replaced with 2 ml of F12 medium supplemented with 10% FBS. Culturing was performed for 6 days and the supernatant was recovered. The amount of human EPO contained in the culture supernatant was quantified by a human EPO ELISA kit (Quantikine IVD Human EPO Immunoassay, R&D system). The results are shown in Table 6. Please note that C1 and C4 were quantified in a $1 \times 10^{-4}$ dilution and C9, C 11 and C20 in a $1 \times 10^{-5}$ dilution.

TABLE 6

| Clone No. | Measurement value (mIU/ml) | Concentration of EPO in CM (IU/ml) | (µg/ml) |
|---|---|---|---|
| C1 | 114 | 1140 | 5.7 |
| C4 | 85 | 850 | 4.2 |
| C9 | 7.6 | 760 | 3.8 |
| C11 | 9.5 | 950 | 4.7 |
| C20 | 7.2 | 720 | 3.6 |
| Average | — | 884 | 4.4 |
| Standard deviation | — | 168 | 0.8 |

From the results shown in Tables 4 to 6 above, it was confirmed that human EPO was expressed in all of the 6 KH21E2 cell clones and the 6 KH21E4 cell clones. Furthermore, expression of human EPO correlated with the copy number of human EPO genes inserted in the HAC vector derived from human chromosome 21. Therefore, it was elucidated that expression of the HAC vector derived from human chromosome 21 can be controlled on the basis of the copy number of genes inserted therein.

Example 10

Insertion of EPO Gene into HAC Vector Derived from Human Chromosome 21 Devoid of a Long-Arm Distal Region and a Short-Arm Proximal Region In the same manner as in the human EPO gene described in Example 7, the human EPO gene was inserted into a HAC vector derived from human chromosome 21. As described in Examples 1 to 4 and 6, a HAC vector derived from chromosome 21 was prepared by deleting a long-arm distal region by telomere truncation and introducing a loxP site in a long-arm proximal region as well as deleting a short-arm distal region by telomere truncation. On the other hand, a human EPO expression plasmid containing a loxP sequence was prepared. The plasmid was introduced into the artificial chromosome by use of the site-specific recombination reaction between the loxP sequences by transiently expressing Cre recombination enzyme. Recombinant having the insert were screened based on whether G418 resistance was acquired or not (reconstitution of a neo gene expression unit by disruption of a promoter).

(1) Transfection and Isolation of G418 Resistant Clone

The 2 clones of CHO cells: CHO(#21)hyg4 and CHO(#21) hyg8 (hereinafter referred to as "H4" and "H8", respectively) retaining the HAC vector derived from human chromosome 21 prepared in Example 17 (described later) were treated with trypsin. $5 \times 10^6$ cells for each were suspended in 0.8 ml of Hank's balanced salt solution (HBSS) and subjected to electroporation using Gene Pulser (Biorad) in the presence of 10 µg of pLN1-EPO vector prepared in Example 7 (1) and 10 µg of Cre enzyme expression vector pBS185 (Lifetech). A voltage of 450V was applied to a condenser having a capacitance of 500 µF and allowed to discharge by use of an electroporation cell having electrodes placed at an interval of 4 mm. The electroporated cells were seeded in five 48-well plastic tissue-culture plates (Falcon) containing Eagle's F12 medium (hereinafter referred to as "F12"; Invitrogen) supplemented with 10% fetus bovine serum (FBS). Two days later, the medium was replaced with a selective medium containing 800 µg/ml G418 (GENETICIN, Invitrogen) and 8 µg/ml Blasticidin S Hydrochloride (Funakoshi). G418 and blasticidin resistant colonies were formed in 2 to 3 weeks. 24 Colonies were isolated from each of host H4 and H8 cells, proliferated and subjected to the following analysis. The cells prepared from H4 will be hereinafter referred to as "H4E cells" and the cells prepared from H8 as "H8E cells".

(2) Confirmation of Transferred Chromosome (2-1) PCR Analysis

PCR amplification was performed with respect to markers PRED 65 and PRED 3 genes, which were located in a long-arm proximal region of human chromosome 21 in the vicinity of a loxP site, and D21S265 marker located in a distal region thereof (Example 1 (3), FIG. 2). It was predicted that a product having the human EPO gene insert introduced by the site-specific recombination between loxP sequences might have the PRED 65 and PRED 3 genes but not have the D21S265 marker. As a result, it was confirmed that amplification was performed as predicted in 21 out of 22 the H4E cell clones. With respect to the 21 clones, PCR amplification of STS markers (pCHB, D21S187, D21S275) positioned in a short-arm proximal region of human chromosome 21 was performed (see Example 6, (3), FIG. 12). Since a short-arm distal region was deleted from of human chromosome 21 at the short-arm proximal region thereof, it is predicted that pCHB and D21S187 markers may not be present and D21S275 marker may be present. As a result, it was confirmed that amplification was performed as predicted in 15 clones.

(2-2) Fluorescence in situ Hybridization (FISH) Analysis

FISH analysis was performed using a human specific probe Cot1 (Gibco BRL) in accordance with the method described in Matsubara et al. (FISH experimental protocol, Shujunsha, 1994). Six out of the clones where all markers were amplified as predicted in the PCR analysis of Section (2-1) mentioned above, were analyzed. As a result, truncated human chromosome 21 was detected in almost all the mitotic images observed. The results are shown in Table 7. From the above, based on relative comparison with the chromosome of a host CHO cell in size, it was confirmed that truncated human chromosome 21 was transferred into the CHO cell.

TABLE 7

| Name of clone | Number of analyzed samples mitotic image/ metaphase nucleus | Number of Cot-1 signals per cell mitotic image/metaphase nucleus | | | | | Retention rate (metaphase nucleus) % |
|---|---|---|---|---|---|---|---|
| | | 0 | 1 | 2 | 3 | 4=< | |
| H4EC10 | 50/100 | 4/1 | 45/98 | 1/1 | 0/0 | 0/0 | 99 |
| H4EC15 | 50/100 | 17/6 | 33/87 | 0/6 | 0/1 | 0/0 | 94 |
| H4EC16 | 50/100 | 5/11 | 45/— | 0/— | 0/— | 0/— | — |
| H4EC17 | 50/100 | 6/4 | 42/82 | 2/14 | 0/0 | 0/0 | 96 |
| H4EC18 | 50/100 | 1/7 | 49/89 | 0/4 | 0 | 0 | 93 |
| H4EC19 | 50/100 | 3/5 | 46/86 | 1/5 | 0/2 | 0/2 | 95 |

From the experiments (2-1) and (2-2) above, it was confirmed that the obtained G418 resistant and blasticidin resistant CHO clone retains a HAC vector derived from human chromosome 21 prepared by deleting a long-arm distal region and a short-arm distal region, and inserting a loxP sequence.

(3) Expression of EPO Gene Inserted in HAC Vector Derived form Human Chromosome 21

Expression of the human EPO gene was determined by quantifying the human EPO protein produced in the culture supernatant in accordance with the enzyme-linked immunosorbent assay (ELISA).

(3-1) Expression of EPO Gene in H4E Cells

With respect to 10 out of 24 clones of G418/blasticidin resistant H4E cell isolated, $1\times10^5$ cells for each were seeded in a 6-well plastic tissue-culture plate (Falcon) containing 2 ml of F12 medium supplemented with 10% FBS and containing 800 µg/ml G418 and 8 µg/ml blasticidin. After the cells reached confluence, the medium was replaced with 2 ml of F12 medium supplemented with 10% FBS. Culturing was performed for 6 days and the supernatant was recovered. The amount of human EPO contained in the culture supernatant was quantified by a human EPO ELISA kit (Quantikine IVD Human EPO Immunoassay, R&D system). The results are shown in Table 8.

TABLE 8

| Clone No. | Measurement value (mIU/ml) | Concentration of EPO in CM | |
|---|---|---|---|
| | | (IU/ml) | (µg/ml) |
| C6 | 57 | 1140 | 5.7 |
| C10 | 27 | 540 | 2.7 |
| C11 | 46 | 920 | 4.6 |
| C15 | 55 | 1100 | 5.5 |
| C16 | 52 | 1040 | 5.2 |
| C17 | 26 | 520 | 2.6 |
| C18 | 49 | 980 | 4.9 |
| C19 | 40 | 800 | 4.0 |
| C20 | 54 | 1080 | 5.4 |
| C21 | 53 | 1060 | 5.3 |

(3-2) Expression of the EPO Gene in H8E Cell

With respect to 6 out of 24 clones of G418/blasticidin resistant H8E cell isolated, $1\times10^5$ cells for each were seeded in a 6-well plastic tissue-culture plate (Falcon) containing 2 ml of F12 medium supplemented with 10% FBS and containing 800 µg/ml G418 and 8 µg/ml blasticidin. After the cells reached confluence, the medium was replaced with 2 ml of F12 medium supplemented with 10% FBS. Culturing was performed for 6 days and the supernatant was recovered. The amount of human EPO contained in the culture supernatant was quantified by a human EPO ELISA kit (Quantikine IVD Human EPO Immunoassay, R&D system). The results are shown in Table 9.

TABLE 9

| Clone No. | Measurement value (mIU/ml) | Concentration of EPO in CM | |
|---|---|---|---|
| | | (IU/ml) | (µg/ml) |
| C9 | 85 | 1700 | 8.5 |
| C14 | 62 | 1240 | 6.2 |
| C17 | 68 | 1360 | 6.8 |
| C20 | 76 | 1520 | 7.6 |
| C21 | 45 | 900 | 4.5 |
| C23 | 62 | 1240 | 6.2 |

From the results of Tables 8 and 9, it was confirmed that the human EPO is expressed in all of the 10 H4E cell clones and 6 H8E cell clones.

Example 11

Transfer of HAC Vector Derived from Human Chromosome 21 into Mouse A9 Cell (1) Microcell Fusion and Isolation of Drug Resistant Clone As a chromosome donor cell, the following CHO cells were used: CHO #21hyg4 and CHO #21hyg8 (hereinafter referred to as "H4 cell" and "H8 cell", respectively) retaining a HAC vector derived from human chromosome 21 obtained in Example 17 by deleting a long-arm distal region and inserting a loxP sequence and thereafter deleting a short-arm distal region by telomere truncation. As a chromosome recipient cell, mouse A9 cell (Oshimura et al., Environ. Health Perspect. 93:57, 1991, Accession No. JCRB0211) was used. At first, microcells were prepared from about $10^7$ H4 cells. More specifically, the H4 or H8 cells, which were cultured in twenty four 25 cm²-centrifugation flasks (Nunc) up to a cell density corresponding to about 60 to 70% saturation, were further cultured in a culture solution (20% FBS, 800 µg/ml G418, F12) containing colcemid (0.1 µg/ml, Demecolcine, Wako Pure Chemical Industries, Ltd.) for 5 days to induce micronuclei. After the medium was removed, each of the centrifugation flasks was filled with a pre-heated (37° C.) solution of cytochalasin B (10 µg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration using SWINNEX-25 (Millipore) equipped with a filter (Whatman) of a pore size of 8 µm, 5 µm and 3 µm. The microcells purified were resuspended in 2 ml of DMEM supplemented with 50 µg/ml phytohemaggulutinin-P (Difco). To 25 cm²-culture flasks (Falcon) in which mouse A9 cells were cultured up to 90% saturation, the purified micronucleus cells were added. After the cell mixture was allowed to stand still at 37° C. for 15 minutes, and cell fusion was performed for one minute in a solution, which was prepared by dissolving PEG 1000 (final concentration of 50% (w/v), Sigma) and DMSO (final concentration of 7% (w/v), Sigma) in DMEM and filtrating by a filter (Saltrius) of 0.22 µm in pore size. After the cells were cultured in DMEM medium containing 10% FBS for 48 hours, the cells were dispersed by trypsin treatment and seeded in two 48-well plastic tissue-culture plates (Falcon). Two days later, the medium was replaced with a selective medium (10% FBS, DMEM) containing blasticidin (4 µg/ml) or hygromycin (700 µg/ml, Invitrogen). After selective culturing was performed for about 3 weeks, formed drug resistant colonies were isolated and subjected to the following analysis. Microcell fusion was performed 7 times to obtain 22 drug resistant colonies. The cells obtained above will be hereinafter referred to as "A9Δcells".

(2) Confirmation of Transferred Chromosome (2-1) PCR Analysis

Of the colonies obtained in Section (1) above, 21 clones were analyzed. PCR amplification was performed with respect to marker PRED 65 and PRED3 genes which were located in a long-arm proximal region of human chromosome 21 in the vicinity a loxP site, and D21S265 marker located in a distal region thereof (see, Example 1, (3) and FIG. 2). It was predicted that a HAC vector having an insert might have the PRED 65 and PRED 3 genes but not have the D21S265 marker. As a result, it was confirmed that amplification was performed as predicted in 20 clones.

Subsequently, PCR amplification was performed with respect to STS markers (pCHB, D21S187, D21S275), which were located in a short-arm proximal region of human chromosome 21 (see, Example 6, (3) and FIG. 12). It was predicted that pCHB and D21S187 markers might not be present but D21S275 marker might be present since the distal region of the short-arm was deleted from human chromosome 21 at the location of short-arm proximal region. As a result, it was confirmed that amplification was performed as predicted in 18 clones.

(2-2) Culture in the Presence of a Selective Drug

Based on the result as to whether or not drug resistant genes present on a HAC vector derived from human chromosome 21, that is, a hygromycin resistant gene (in short-arm distal region) and a blasticidin resistant gene (in long-arm proximal region) function in the presence of selective drugs, it was confirmed whether or not a region containing each of the drug resistant genes is present.

Nine clones exhibited amplification as predicted in Section (2-1) above were cultured in a 6-well tissue-culture plate (Falcon), each well containing a selective medium (10% FBS, DMEM) containing blasticidin (4 µg/ml), up to a cell density corresponding to about 60 to 70% saturation. After rinsed with PBS (Invitrogen) twice, clone cells were cultured in a culture solution containing hygromycin (700 µg/ml) alone or a culture solution containing blasticidin (4 µg/ml) and hygromycin (700 µg/ml) for one week. The results are shown in Table 10.

TABLE 10

| Name of clone | Brasticidin (Bsd) | Hygromycin (Hyg) | Bsd + Hyg |
|---|---|---|---|
| A9Δ10 | R | R | R |
| A9Δ11 | R | R | R |
| A9Δ12 | R | — | R |
| A9Δ13 | R | R | R |
| A9Δ111 | R | R | R |
| A9Δ113 | R | R | R |
| A9Δ114 | R | R | R |
| A9Δ115 | R | R | R |
| A9Δ116 | R | R | R |

R; Drug resistant
—; No experimental data

From the above, it was confirmed that all clones were blasticidin and hygromycin resistant.

(2-3) Fluorescence in situ Hybridization (FISH) Analysis

FISH analysis was performed using a human specific probe Cot1 (Gibco BRL) in accordance with the method described in Matsubara et al. (FISH experimental protocol, Shujunsha, 1994). Two clones in which all markers were amplified as predicted in the PCR analysis performed in Section (2-1) above and which exhibited blasticidin resistant and hygromycin resistant in Section (2-2) above, were analyzed. As a result, truncated human chromosome 21 was detected in almost all the mitotic images observed. The results are shown in Table 11.

TABLE 11

| Name of clone | Number of analyzed samples mitotic image/ metaphase nucleus | Number of Cot-1 signals per cell mitotic image/metaphase nucleus | | | | Retention rate (metaphase nucleus) |
|---|---|---|---|---|---|---|
| | | 0 | 1 | 2 | 3 | % |
| A9Δ11 | 50/100 | 11/31 | 36/65 | 3/2 | 0/2 | 69 |
| A9Δ12 | 50/100 | 2/11 | 47/87 | 0/2 | 1/0 | 89 |

From the above, based on relative comparison with the chromosome of a host mouse A9 cell in size, it was confirmed that truncated human chromosome 21 was transferred in the mouse A9 cell. Hereinafter, 2 cell clones will be referred to as "A9Δ11" and "A9Δ12", respectively.

From the experiments (2-1) to (2-3) above, it was confirmed that the two blasticidin resistant and hygromycin resistant clones retain a HAC vector derived from truncated human chromosome 21 devoid of the long-arm and the short-arm thereof.

Example 12

Transfer of HAC Vector Derived from Human Chromosome 21 having the Human EPO Gene into Mouse A9 Cell (1) Microcell Fusion and Isolation of Drug Resistant Clone Of the CHO cells retaining a HAC vector derived from human chromosome 21 obtained in Example 10 by deleting a long-arm distal region and inserting a loxP sequence, and thereafter deleting a short-arm distal region thereof by telomere truncation, and by inserting a single copy of the human EPO gene, a clone (H4E C10, H4E C15 or H4E C16 cell)

having a high micronucleus formation ability was used as a chromosome donor cell. As a chromosome recipient cell, mouse A9 cell (Oshimura et al., Environ. Health Perspect. 93:57, 1991, Accession No. JCRB0211) was used. At first, microcells were prepared from about $10^8$ H4E C15 or H4E C16 cells. H4E C15 or H4E C16 cells, which were cultured in twenty four 25 cm²-centrifugation flasks (Nunc) up to a cell density corresponding to about 60 to 70% saturation, were further cultured in a culture solution (20% FBS, 800 μg/ml G418, F12) containing colcemid (0.1 μg/ml, Demecolcine, Wako Pure Chemical Industries, Ltd.) for 4 days to induce micronuclei. After the medium was removed, each of the centrifugation flasks was filled with a pre-heated (37° C.) solution of cytochalasin B (10 μg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration using SWINNEX-25 (Millipore) equipped with a filter (Whatman) of a pore size of 8 μm, 5 μm and 3 μm. The microcells purified were resuspended in 2 ml of DMEM supplemented with 50 μg/ml or 100 μg/ml phytohemagglutinin-P (Difco). To 25 cm²-culture flasks (Falcon) in which mouse A9 cells were cultured up to 90% saturation, the purified micronucleus cells were added. After the cell mixture was allowed to stand still at 37° C. for 15 minutes, and cell fusion was performed for one minute in a solution prepared by dissolving PEG 1000 (final concentration of 50% (w/v), Sigma) and DMSO (final concentration of 7% (w/v), Sigma) in DMEM and filtrating by a filter (Saltrius) of 0.22 μm in pore size. After the cells were cultured in DMEM medium containing 10% FBS for 48 hours, the cells were dispersed by trypsin treatment and seeded in two 48-well plastic tissue-culture plates (Falcon). Two days later, the medium was replaced with a selective medium (10% FBS, DMEM) containing blasticidin (6 μg/ml) or G418 (600 μg/ml). After selective culturing was performed for about 3 weeks, formed drug resistant colonies were isolated and subjected to the following analysis. Microcell fusion was performed 12 times to obtain 39 of G418 resistant colonies. The cells obtained above will be hereinafter referred to as "AΔE cells".

(2) Confirmation of Transferred Chromosome
(2-1) PCR Analysis

Of the colonies obtained in Section (1) above, 25 clones were analyzed. PCR amplification was performed with respect to marker PRED 65 and PRED3 genes, which were located in a long-arm proximal region of human chromosome 21 in the vicinity of a loxP site, and D21S265 marker located in a distal region thereof (see, Example 1 (3) and FIG. 2). It was predicted that a human EPO gene insert by the site specific recombination between loxP sequences might have the PRED 65 and PRED 3 genes but not have the D21S265 marker. As a result, it was confirmed that amplification was performed as predicted in 24 clones. With respect to STS markers (pCHB, D21S187, D21S275), which were located in a short-arm proximal region of human chromosome 21, PCR amplification was performed (see, Example 6, (3) and FIG. 12). Since the short-arm distal region was deleted from human chromosome 21 in the proximal region of the short-arm thereof, it was predicted that pCHB and D21S187 markers might not be present but D21S275 marker might be present. As a result, it was confirmed that amplification was performed as predicted in 19 clones.

(2-2) Culture in the Presence of a Selective Drug

Based on the result as to whether or not drug resistant genes present on a HAC vector derived from human chromosome 21, that is, a hygromycin resistant gene (in short-arm distal region), a blasticidin resistant gene (in long-arm proximal region), and a neomycin resistant gene (in long-arm proximal region) present on the HAC vector derived from human chromosome 21, function in the presence of selective drugs, it was confirmed whether or not a region containing each of the drug resistant gene is present.

Seven clones exhibited amplification as predicted in Section (2-1) above were cultured in a 6-well tissue-culture plate (Falcon) containing a selective medium (10% FBS, DMEM) containing G418 (600 μg/ml) or blasticidin (6 μg/ml), up to a cell density corresponding to about 60 to 70% saturation. After rinsed with PBS (Invitrogen) twice, cell clones were cultured in a culture solution containing blasticidin, hygromycin (700 μg/ml) and G418 for one week or 10 days. The results are shown in Table 12.

TABLE 12

| Name of clone | Brasticidin (Bsd) | Hygromycin (Hyg) | Genecitin (G) | Bsd + Hyg + G |
|---|---|---|---|---|
| AΔE1 | R | R | R | R |
| AΔE2 | R | R | R | R |
| AΔE4 | — | — | R | R |
| AΔE5 | R | — | — | R |
| AΔE8 | R | R | R | R |
| AΔE16 | — | R | R | R |
| AΔE18 | — | R | R | R |

R; Drug resistant
—; No experimental data

From the above, it was confirmed that 7 clones were triple-drug resistant, that is, resistant against blasticidin, hygromycin and G418.

(2-3) Fluorescence in situ Hybridization (FISH) Analysis

FISH analysis was performed using a human specific probe Cot1 (Gibco BRL) in accordance with the method described in Matsubara et al. (experimental protocol, Shujunsha, 1994). Seven clones in which all markers were amplified as predicted in the PCR analysis in Section (2-1) above, were analyzed. As a result, truncated human chromosome 21 was detected in almost all the mitotic images observed. The results are shown in Table 13.

TABLE 13

| Name of clone | Number of analyzed samples mitotic image/ metaphase nucleus | Number of Cot-1 signals per cell mitotic image/metaphase nucleus | | | | | Retention rate (metaphase nucleus) |
|---|---|---|---|---|---|---|---|
| | | 0 | 1 | 2 | 3 | 4=< | % |
| AΔE51 | 50/100 | 1/1 | 6/11 | 7/21 | 15/31 | 21/36 | 87 |
| AΔE52 | 50/100 | 6/13 | 38/80 | 6/6 | 0/1 | 0 | 99 |
| AΔE53 | 50/100 | 1/4 | 5/8 | 3/12 | 11/33 | 30/43 | 96 |
| AΔE54 | 50/100 | 7/7 | 32/77 | 9/16 | 1/0 | 1/0 | 86 |
| AΔE55 | 50/100 | 14/39 | 5/17 | 6/13 | 1/16 | 24/15 | 72 |
| AΔE4 | 48/100 | 1/9 | 41/86 | 4/5 | 1/0 | 1/0 | 91 |
| AΔE18 | 50/100 | 1/4 | 32/67 | 17/29 | 0 | 0 | 96 |

From the above, based on relative comparison with the chromosome of a host mouse A9 cell in size, it was confirmed that truncated human chromosome 21 was transferred in the mouse A9 cell.

From the experiments (2-1) to (2-3) above, it was confirmed that the AΔE cells obtained above retain a HAC vector derived from truncated human chromosome 21 having the human EPO gene insert and devoid of the long-arm and the short-arm thereof.

(3) Confirmation of a Recombinant having Human EPO Gene Insert

Screening of recombinants having an insert, that is, whether or not the insert was introduced into loxP sequence site on a HAC vector derived from human chromosome 21, was confirmed by PCR amplification using primers designed on a sequence derived from the human EPO gene donor vector and on the HAC vector so as to flank the loxP sequence site.

With respect to 12 clones of the AΔE cell, PCR was performed by using Neo Rp2 primer (SEQ ID No. 38) shown in Example 9(4) and M13RVprimer (SEQ ID No. 39) derived from plasmid vector pBS226. In the case of a recombinant having an insert, it was predicted to amplify an about 2.3 kbp fragment including a region from a portion having CMV promoter, human EPO gene, and SV40 poly A additional sequence to a loxP sequence, and a region from a loxP sequence derived from pSF1 to a part of the neo gene. As a result, amplification was performed as predicted in all of the 12 clones.

From the above, it was confirmed that all of the clones of the AΔE cell retained a HAC vector derived from human chromosome 21, in which a copy of DNA insert containing the CMV promoter, human EPO gene, and SV40 poly A additional sequence was inserted.

(4) Expression of EPO Gene Inserted in HAC Vector Derived from Human Chromosome 21

Expression of the human EPO gene was determined by quantifying human EPO protein produced in the culture supernatant in accordance with the enzyme-linked immunosorbent assay (ELISA).

With respect to 4 AΔE clones isolated, $1 \times 10^5$ cells for each were seeded in a 6-well plastic tissue-culture plate (Falcon) containing 2 ml of DMEM medium, which was supplemented with 10% FBS and containing 600 μg/ml G418 and 6 μg/ml blasticidin. After the cells reached confluence, the medium was replaced with 2 ml of F12 medium supplemented with 10% FBS. Culturing was performed for 4 days or 5 days and the supernatant was recovered. The amount of human EPO contained in the culture supernatant was quantified without dilution by a human EPO ELISA kit (Quantikine IVD Human EPO Immunoassay, R&D system). The results are shown in Table 14.

TABLE 14

| Clone No. | Measurement value (mIU/ml) | Concentration of EPO in CM (pg/ml) |
|---|---|---|
| AΔE51 | >200 | >1000 |
| AΔE53 | 192 | 910 |
| AΔE4 | >200 | >1000 |
| AΔE18 | >200 | >1000 |

The human EPO concentrations of the culture supernatants of AΔE51, AΔE4 and AΔE18 were greater than a detection limit by the human EPO ELISA kit (Quantikine IVD Human EPO Immunoassay, R&D system).

From the above, it was confirmed that AΔE cells produce human EPO protein.

Example 13

Transfer of Human Chromosome 14 Fragment (SC20) into Normal Human Fibroblast Cell (1) Transfer of SC20 into Normal Human Fibroblast Cell (HFL-1)
(1-1) Microcell Fusion (Plate Method) and Isolation of Drug Resistant Clone As a chromosome donor cell, mouse A9 cell (C11-SC20 cell, Tomizuka et al., Nature Genet. (USA), Vol. 16, p. 133-143, 1997) containing a human chromosome 14 fragment (SC20) was used. As a chromosome recipient cell, a normal human fibroblast cell, HFL-1 (obtained from the cellular material development laboratory of RIKEN, Accession No. RCB0521) was used. At first, microcells were prepared from about $10^7$ cells. Specifically, the C11-SC20 cells, which were cultured in twelve 25 cm²-centrifugation flasks (Nunc) up to a cell density corresponding to about 80 to 90% saturation, were further cultured in a culture solution (20% FBS, 800 μg/ml G418, DMEM) containing colcemid (0.05 μg/ml, Demecolcine, Wako Pure Chemical Industries, Ltd.) for 48 hours to induce micronuclei. After the medium was removed, each of the centrifugation flasks was filled with a pre-heated (37° C.) solution of cytochalasin B (10 μg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration using WINNEX-25 (Millipore) equipped with a filter (Whatman) of a pore size of 8 μm, 5 μm and 3 μm. The microcells purified were resuspended in 2 ml of DMEM supplemented with 50 μg/ml phytohemagglutinin-P (Difco). To 25 cm²-culture flasks (Falcon) in which HFL-1 cells were cultured up to 90% saturation, the purified micronucleus cells were added. After the cell mixture was allowed to stand still at 37° C. for 15 minutes, and cell fusion was performed for one minute in a solution prepared by dissolving PEG 1500 (final concentration of 45% (w/v), Roche Diagnostics) and DMSO (final concentration of 10% (w/v), Sigma) in DMEM and sterilizing by filtrating using a filter (Saltrius) of 0.22 μm in pore size. After the cells were cultured in DMEM medium containing 15% FBS for 48 hours, the cells were dispersed by trypsin treatment, and seeded in a single 48-well plastic tissue-culture plate (Falcon) coated with collagen I. Two days later, the medium was replaced with a selective medium (15% FBS, DMEM) containing G418 (300 μg/ml). After selective culturing was performed for about 3 weeks, formed drug resistant colonies were isolated and subjected to the following analysis. Microcell fusion was performed 3 times to obtain 21 G418 resistant colonies.

(1-2) Microcell Fusion (Suspension Method) and Isolation of Drug Resistant Clone Microcells were prepared and purified in the same manner as in Section (1-1) above and resuspended in 6 ml of DMEM. HFL-1 cells were cultured up to 90% saturation in a 175 cm²-culture flask (Falcon). After the cells were dispersed by trypsin treatment, they were washed with DMEM twice and then suspended in 7 ml of DMEM. The HFL-1 cell suspension was overlaid on the microcell suspension obtained above and centrifuged. After the supernatant was removed, the pellet was suspended by tapping. To the resultant suspension, 0.5 ml of PEG1500 (final concentration of 50% (w/v), Roche Diagnostics) was added and cell fusion was performed for 120 seconds. To the solution, 5 ml of DMEM was added at a rate of 1 ml/minute and further 5 ml of DMEM was added. After the solution was allowed to stand still at 37° C. for 10 minutes, it was centrifuged, resuspended in DMEM medium containing 15% FBS and seeded in two 48-well plastic tissue-culture plates (Falcon) coated with collagen I. Two days later, the medium was replaced with a selective medium (15% FBS, F12) containing G418 (300 µg/ml). After selective culturing was performed for about 3 weeks, formed drug resistant colonies were isolated and subjected to the following analysis. Microcell fusion was performed once to obtain 2 G418 resistant colonies.

(1-3) Confirmation of Transferred Chromosome
(1-3-1) PCR Analysis

The transferred chromosome was confirmed by PCR amplification of a neo gene present on SC20. The sequences of the primer oligonucleotides used herein are shown below:

```
                                             (SEQ ID No. 40)
    421F:  5'-TTT GCA TGT CTT TAG TTC TAT GAT GA-3';

(SEQ ID No. 41)
    778R:  5'-AGG TCG GTC TTG ACA AAA AGA AC-3'.
```

These primers were prepared based on the nucleotide sequence of plasmid vector pSTneoB (Kato et al., Cell Struct Funct, 12:575-580, 1987).

With respect to 12 clones of G418 resistant cells obtained in Sections (1-1) and (1-2) above, PCR amplification was performed by using 421F primer (SEQ ID No. 40) and 778R (SEQ ID No. 41) primer. It was predicted that a clone retaining a HAC vector having an insert might have a neo gene. As a result, it was confirmed that amplification was performed as predicted in all clones.

(1-3-2) Chromosome Analysis

Chromosome analysis was performed by Giemsa staining in accordance with the method described in Kuroki et al. (Cell engineering handbook, Yodosha, 1992). About 20 metaphase chromosomal images of 2 clones out of the G418 resistant HFL-1 cells were analyzed. A mini chromosome, which was smaller than endogenous chromosome 14 and not observed in the parent line HFL-1, was observed in the G418 resistant clone.

From the experiments (1-3-1) and (1-3-2), it was confirmed that the G418 resistant HFL-1 clones obtained above retain SC20.

(2) Transfer of SC20 into Normal Human Fibroblast Cell HUC-F2
(2-1) Microcell Fusion (Plate Method) and Isolation of Drug Resistant Clone As a chromosome donor cell, mouse A9 cell (C11-SC20 cell, Tomizuka et al., Nature Genet. (USA), Vol. 16, p. 133-143, 1997) containing a human chromosome 14 fragment (SC20) was used. As a chromosome recipient cell, a normal human fibroblast cell HUC-F2 (obtained from the cellular material development laboratory of RIKEN, Accession No. RCB0436) was used. At first, microcells were prepared from about $10^7$ cells. More specifically, the C11-SC20 cells, which were cultured in twelve 25 cm²-centrifugation flasks (Nunc) up to a cell density corresponding to about 80 to 90% saturation, were further cultured in a culture solution (20% FBS, 800 µg/ml G418, DMEM) containing colcemid (0.05 µg/ml, Demecolcine, Wako Pure Chemical Industries, Ltd.) for 48 hours to induce micronuclei. After the medium was removed, each of the centrifugation flasks was filled with a pre-heated (37° C.) solution of cytochalasin B (10 µg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration by use of SWINNEX-25 (Millipore) equipped with a filter (Whatman) of a pore size of 8 µm, 5 µm and 3 µm. The microcells purified were resuspended in 2 ml of DMEM supplemented with 50 µg/ml phytohemaggulutinin-P (Difco). To 25 cm²-culture flasks (Falcon) in which HUC-F2 cells were cultured up to 90% saturation, the purified micronucleus cells were added. After the cell mixture was allowed to stand still at 37° C. for 15 minutes, and cell fusion was performed for one minute in a solution prepared by dissolving PEG 1500 (final concentration of 45% (w/v), Roche Diagnostics) or PEG 1000 (final concentration of 45% (w/v), Sigma) and DMSO (final concentration of 10% (w/v), Sigma) in DMEM and sterilizing by filtrating using a filter (Saltrius) of 0.22 µm in pore size. After the cells were cultured in aMEM medium containing 10% FBS for 48 hours, the cells were dispersed by trypsin treatment, and seeded in a single 48-well plastic tissue-culture plate (Falcon) coated with collagen I. Two days later, the medium was replaced with a selective medium (10% FBS, αMEM) containing G418 (400 µg/ml). After selective culturing was performed for about 3 weeks, formed drug resistant colonies were isolated and subjected to the following analysis. Microcell fusion was performed 4 times to obtain 8 G418 resistant colonies.

(2-2) Microcell Fusion (Suspension Method) and Isolation of Drug Resistant Clone Microcells were prepared and purified in the same manner as in Section (1-1) above and resuspended in 6 ml of DMEM. HUC-F2 cells were cultured up to 90% saturation in a 175 cm²-culture flask (Falcon). After the cells were dispersed by trypsin treatment, they were washed with DMEM twice and then suspended in 7 ml of DMEM. The HUC-F2 cell suspension was overlaid on the microcell suspension obtained above and centrifuged. After the supernatant was removed, the pellet was suspended by tapping. To the resultant suspension, 0.5 ml of PEG1500 (final concentration of 50% (w/v), Roche Diagnostics) was added and cell fusion was performed for 120 seconds. To the solution, 5 ml of DMEM was added at a rate of 1 ml/minute and further 5 ml of DMEM was added. After the solution was allowed to stand still at 37° C. for 10 minutes, it was centrifuged. The pellet was resuspended in αMEM medium containing 10% FBS and seeded in two 48-well plastic tissue-culture plates (Falcon) coated with collagen I. Two days later, the medium was replaced with a selective medium (10% FBS, aMEM) containing G418 (400 µg/ml). After selective culturing was performed for about 3 weeks, formed drug resistant colonies were isolated and subjected to the following analysis. Microcell fusion was performed once to obtain 6 G418 resistant colonies.

(2-3) Confirmation of Transferred Chromosome

The transferred chromosome was confirmed by PCR amplification of a neo gene present on SC20. With respect to 7 clones of the G418 resistant cell obtained in Sections (2-1) and (2-2), PCR amplification was performed by using 421F primer (SEQ ID No. 40) and 778R primer (SEQ ID No. 41). It was predicted that an insert in a HAC vector might have a neo gene. As a result, it was confirmed that amplification was performed as predicted in all clones. From the experiment above, it was confirmed that the obtained G418 HUC-F2 clones retain SC20.

(3) Transfer of SC20 into Normal Human Fibroblast Cell, HF-19: Microcell Fusion and Isolation of Drug Resistant Clone As a chromosome donor cell, mouse A9 cell (C11-SC20 cell, Tomizuka et al., Nature Genet. (USA), Vol. 16, p. 133-

143, 1997) containing a human chromosome 14 fragment (SC20) was used. As a chromosome recipient cell, a normal human fibroblast cell, HF-19 (obtained from the cellular material development laboratory of RIKEN, Accession No. RCB0210) was used. At first, microcells were prepared from about $10^7$ cells. The C11-SC20 cells, which were cultured in twelve 25 cm$^2$-centrifugation flasks (Nunc) up to a cell density corresponding to about 80 to 90% saturation, were further cultured in a culture solution (20% FBS, 800 μg/ml G418, DMEM) containing colcemid (0.05 μg/ml, Demecolcine, Wako Pure Chemical Industries, Ltd.) for 48 hours to induce micronuclei. After the medium was removed, each of the centrifugation flasks was filled with a pre-heated (37° C.) solution of cytochalasin B (10 μg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration by use of SWINNEX-25 (Millipore) equipped with a filter (Whatman) of a pore size of 8 μm, 5 μm and 3 μm. The microcells purified were resuspended in 2 ml of DMEM supplemented with 50 μg/ml phytohemagguluti-nin-P (Difco). To 25 cm$^2$-culture flasks (Falcon) in which HF-19 cells were cultured up to 90% saturation, the purified micronucleus cells were added. After the cell mixture was allowed to stand still at 37° C. for 15 minutes, and cell fusion was performed for one minute in a solution prepared by dissolving PEG 1500 (final concentration of 45% (w/v), Roche Diagnostics) and DMSO (final concentration of 10% (w/v), Sigma) in DMEM and sterilizing by filtrating using a filter (Saltrius) of 0.22 μm in pore size. After the cells were cultured in αMEM medium containing 10% FBS for 48 hours, the cells were dispersed by trypsin treatment, and seeded in a 48-well plastic tissue-culture plate (Falcon) coated with collagen I. Two days later, the medium was replaced with a selective medium (10% FBS, aMEM) containing G418 (400 μg/ml). After selective culturing was performed for about 3 weeks, formed drug resistant colonies were isolated. Microcell fusion was performed once to obtain a single G418 resistant colony.

Example 14

Transfer of HAC Vector Derived from Human Chromosome 21 into Normal Human Fibroblast Cell (1) Microcell Fusion and Isolation of Drug Resistant Clone
(1-1) Microcell Fusion by Using a CHO Cell Retaining a HAC Vector Derived from Human Chromosome 21 as a Chromosome Donor Cell As a chromosome donor cell, a clone (H4E C10 cell) having a high micronucleus formation ability out of CHO cells obtained in Example 10 and retaining a HAC vector derived from human chromosome 21 containing a single copy of the human EPO gene, which was prepared by deleting a long-arm distal region and inserting a loxP sequence and thereafter deleting a short-arm distal region by telomere truncation, the human EPO gene being introduced by the site specific recombination reaction between the loxP sequences by transiently expressing Cre recombinant enzyme. As a chromosome recipient cell, normal human fibroblast cell HFL-1 (obtained from the cellular material development laboratory of RIKEN, Accession No. RCB0521) was used. At first, microcells were prepared from $10^8$ H4E C10 cells. More specifically, the H4E C10 cells, which were cultured in forty eight 25 cm$^2$-centrifugation flasks (Nunc) up to a cell density corresponding to about 60 to 70% saturation, were further cultured in a culture solution (20% FBS, 800 μg/ml G418, F12) containing colcemid (0.1 μg/ml, Demecolcine, Wako Pure Chemical Industries, Ltd.) for 4 days to induce micronuclei. After the medium was removed, each of the centrifugation flasks was filled with a pre-heated (37° C.) solution of cytochalasin B (10 μg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration by use of SWINNEX-25 (Millipore) equipped with a filter (Whatman) of a pore size of 8 μm, 5 μm and 3 μm The microcells purified were resuspended in 2 ml of DMEM supplemented with 50 μg/ml phytohemaggulutinin-P (Difco). To 25 cm$^2$-culture flasks (Falcon) in which HFL-1 cells were cultured up to 90% saturation, the purified micronucleus cells were added. After the cell mixture was allowed to stand still at 37° C. for 15 minutes, and cell fusion was performed for one minute in a solution prepared by dissolving PEG 1500 (final concentration of 45% (w/v), Roche Diagnostics) and DMSO (final concentration of 10% (w/v), Sigma) in DMEM and sterilizing by filtrating using a filter (Saltrius) of 0.22 μm in pore size. After the cells were cultured in DMEM medium containing 20% FBS for 48 hours, the cells were dispersed by trypsin treatment, and seeded in a single 48-well plastic tissue-culture plate (Falcon) coated with collagen I. Two days later, the medium was replaced with a selective medium (20% FBS, DMEM) containing G418 (300 μg/ml) or blasticidin (6 μg/ml). After selective culturing was performed for about 3 weeks, formed drug resistant colonies were isolated and subjected to the following analysis. Microcell fusion was performed 5 times to obtain 3 drug resistant colonies. The cells will be referred to as "HCΔE cells".

(1-2) Microcell Fusion by Using Mouse A9 Cell Retaining HAC Vector Derived from Human Chromosome 21 as a Chromosome Donor Cell Out of mouse A9 cells obtained in Example 12 and retaining a HAC vector derived from human chromosome 21 containing a single copy of the human EPO gene, which was prepared by deleting a long-arm distal region and inserting a loxP sequence, followed by deleting a short-arm distal region by telomere truncation, and transiently expressing Cre recombinant enzyme to introduce the human EPO gene by use of the site specific recombination reaction between the loxP sequences, clones (AΔ51 or AΔE5 cell) having a high micronucleus formation ability were used as a chromosome donor cell. As a chromosome recipient cell, normal human fibroblast cell HFL-1 (obtained from the cellular material development laboratory of RIKEN, Accession No. RCB0521) was used. At first, microcells were prepared from about $10^7$ cells. More specifically, AΔ51 or AΔE5 cells, which were cultured in twelve 25 cm$^2$-centrifugation flasks (Nunc) up to a cell density corresponding to about a 80 to 90% saturation, were further cultured in a culture solution (20% FBS, 600 μg/ml G418, DMEM) containing colcemid (0.1 μg/ml, Demecolcine, Wako Pure Chemical Industries, Ltd.) for 72 hours to induce micronuclei. After the medium was removed, each of the centrifugation flasks was filled with a pre-heated (37° C.) solution of cytochalasin B (10 μg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration by use of SWINNEX-25 (Millipore) equipped with a filter (Whatman) of a pore size of 8 μm, 5 μm and 3 μm The microcells purified were resuspended in 2 ml of DMEM supplemented with 50 μg/ml phytohemaggulutinin-P (Difco). To 25 cm$^2$-culture flasks (Falcon) in which HFL-1 cells were cultured up to 90% saturation, the purified micronucleus cells were added. After the cell mixture was allowed to stand still at 37° C. for 15 minutes, and cell fusion was performed for one minute in a solution prepared by dissolving PEG 1500 (final concentration of 45% (w/v), Roche Diagnostics) and DMSO (final concentration of 10% (w/v), Sigma) in DMEM and sterilizing by filtrating using a filter (Saltrius) of 0.22 μm in pore size. After the cells were cultured in DMEM medium containing 20% FBS for 48 hours, the cells were dispersed by trypsin treatment, and seeded in a single 48-well plastic tissue-culture plate (Falcon) coated with collagen I. Two days later, the medium was replaced with a selective medium (20% FBS, DMEM) containing G418 (300 μg/ml) or blasticidin (6 μg/ml). After selective culturing was performed for about 3 weeks, formed drug resistant colonies were isolated and subjected to the following analysis. Microcell fusion was performed 10 times to obtain 27 drug resistant colonies. The cells will be referred to as "HΔE cells".

(2) Confirmation of Transferred Chromosome

The transferred chromosome was confirmed by PCR amplification with reference to the presence or absence of a neo gene present on a HAC vector derived from human chromosome 21. The sequences of the primer oligonucleotides used for PCR amplification are shown below:

```
                                          (SEQ ID No. 42)
1291F:     5'-CTA CCC GTG ATA TTG CTG AAG AG-3';

(SEQ ID No. 43)
1667R:     5'-ATT TGC ACT GCC GGT AGA ACT-3'.
```

These primers were prepared based on the nucleotide sequence of plasmid vector pSTneoB (Kato et al., Cell Struct Funct, 12:575-580, 1987).

PCR amplification was performed by using 1291F primer (SEQ ID No. 42) and 1667R primer (SEQ ID No. 43). In the case where the HAC vector derived from human chromosome 21 was present, it was predicted to amplify a 0.4 kbp fragment containing a part of the neo gene. As a result, it was confirmed that amplification was performed as predicted in all of 5 HΔE cell clones.

From the above, it was confirmed that that HΔE cell retains the HAC vector derived from human chromosome 21.

(3) Expression of EPO Gene Inserted in HAC Vector Derived from Human Chromosome 21

Expression of the human EPO gene was determined by quantifying human EPO protein produced in the culture supernatant in accordance with the enzyme-linked immunosorbent assay (ELISA).

With respect to 3 blasticidin resistant HCΔE cell clones and 8 G418 or blasticidin resistant HΔE cell clones isolated, cells were seeded in a 48-well plastic tissue-culture plates (Falcon) containing 0.5 ml of DMEM medium supplemented with 20% FBS and containing 300 μg/ml G418 or 6 μg/ml blasticidin. After the cells were cultured for 2 days, 3 days or 4 days, the supernatant was recovered. The amount of human EPO contained in the culture supernatant was quantified without dilution by a human EPO ELISA kit (Quantikine IVD Human EPO Immunoassay, R&D system). The results are shown in Table 15.

TABLE 15

| Clone No. | Measurement value (mIU/ml) | Concentration of EPO in CM (pg/ml) |
| --- | --- | --- |
| HΔE51-1 | >200 | >1000 |
| HΔE51-2 | 46 | 230 |
| HΔE51-3 | 130 | 650 |
| HΔE51-4 | 62 | 310 |
| HΔE5-1 | >200 | >1000 |
| HΔE5-2 | >200 | >1000 |
| HΔE5-3 | >200 | >1000 |
| HΔE5-4 | >200 | >1000 |
| HCΔE1-1 | 30 | 150 |
| HCΔE1-2 | 57 | 285 |
| HCΔE3-1 | 46 | 230 |

In the clones of HΔE51-1, HΔE5-1, HΔE5-2, HΔE5-3, and HΔE5-4, the human EPO concentration in a culture supernatant was greater than a detection limit by the human EPO ELISA kit (Quantikine IVD Human EPO Immunoassay, R&D system).

From the above, it was confirmed that HCΔE cell and HΔE cell clones produce human EPO protein.

Example 15

Construction of Vector for Inserting EPO and Human Telomerase (hTERT) Genes into HAC Vector Derived from Human Chromosome 21

(1) Construction of hTERT Expression Plasmid pLN1-hTERT Containing a loxP Sequence A human telomerase (hTERT) gene has a code region of 3399 bp and contains a G/C rich sequence at the 5' region thereof. For the reason, it was predicted difficult to amplify the entire gene by designing the primers at the both end of the coding region. Therefore, the coding region was divided into 3 regions: 1 to 800 bp (hereinafter referred to as "5' hTERT"), 679 to 1993 bp (hereinafter referred to as "M-XhTRET") and 1952 to 3339 bp (hereinafter referred to as "3' hTRET". Please note that, the position in the nucleotide sequence was expressed by regarding "A" of initiation codon "ATG" as 1). After individual regions were amplified by PCR and cloned and these regions were ligated to each other. In this manner, cloning of the hTERT gene was performed. This method will be specifically described below.

(1-1) Cloning of 5' hTERT

The sequences of primer oligonucleotides used in construction of a plasmid vector are shown below.

```
hTERT Fw6:
                                          (SEQ ID No. 44)
5'-CTG CTG CGC ACG TGG GAA G-3' hTERT Rv6:
                                          (SEQ ID No. 45)
5'-GGT CTG GCA GGT GAC ACC AC-3' hTERT Fw1:
                                          (SEQ ID No. 46)
5'-GAA GAT CTT CAT CGA TCG GCC ACC ATG CCG CGC
GC-3' hTERT Rv7:
                                          (SEQ ID No. 47)
5'-TCA CTC GGT CCA CGC GTC CT-3'
```

These primers were prepared based on the nucleotide sequence (Accession No. NM003219) obtained from the GenBank.

Using 1 ng of HL-60cDNA (Marathon-Ready cDNA, CLONTECH) as a template, PCR amplification was performed in 50 µl of a reaction solution containing hTERT Fw6 (SEQ ID No. 44) and hTERT Rv6 (SEQ ID No. 45) each having a final concentration of 0.4 µM using 2.5 units of LA Taq (Takara Shuzo Co., Ltd.). As a thermal cycler, Gene-Amp9600 (Applied Biosystems) was used. The PCR amplification was performed by placing at 98° C. for 10 minutes, followed by repeating a cycle consisting of denaturation at 98° C. for 30 seconds, annealing and extension at 72° C. for 5 minutes three times, a cycle consisting of denaturation at 98° C. for 30 seconds, annealing and extension at 70° C. for 5 minutes, 2 times, and a cycle consisting of denaturation at 98° C. for 30 seconds, annealing and extension at 68° C. for 5 minutes, 35 times. Furthermore, using 2 µl of the resultant PCR product as a template, PCR amplification was performed by using hTERT Fw1 (SEQ ID No. 46) and hTERT Rv7 (SEQ ID No. 47) each having a final concentration of 0.4 µM by use of 2.5 units of LA Taq (Takara Shuzo Co., Ltd.) in 50 µl of a reaction solution. The PCR amplification was performed by placing at 98° C. for 10 minutes, followed by repeating a cycle consisting of denaturation at 98° C. for 30 seconds, annealing and extension at 72° C. for 5 minutes, three times; a cycle consisting of denaturation at 98° C. for 30 seconds, annealing and extension at 70° C. for 5 minutes, twice; and a cycle consisting of denaturation at 98° C. for 30 seconds, annealing and extension at 68° C. for 5 minutes, 35 times. As a result, a DNA fragment of about 0.8 kb was obtained.

The DNA fragment of about 0.8 kb was purified by QIAQUICK PCR Purification Kit (QIAGEN) and both ends thereof were digested with KOD DNA polymerase (Toyobo) to obtain blunt ends, and further digested with Bgl II (Takara Shuzo Co., Ltd.) to make the 5' end side cohesive. As a result, a DNA fragment for 5' hTERT insertion was obtained. After plasmid vector pLN1-EPO was digested with Xho I (Takara Shuzo Co., Ltd.), both ends thereof were digested with KOD DNA polymerase (Toyobo) to obtain blunt ends. The resultant fragment was further digested with BamH I (Takara Shuzo Co., Ltd.) to remove the human EPO gene. To the obtained BamH I-blunted end site, the DNA fragment for 5'hTERT insert was cloned. As a host *Escherichia coli*, XL-10 Gold (Stratagene) was used. The nucleotide sequence of the DNA fragment for 5' hTERT insert thus cloned was analyzed by a DNA sequencer (PRISM3700, Applied Biosystems) and confirmed to be identical to the corresponding portion of the nucleotide sequence obtained from the GenBank. From the above, the resultant plasmid vector was designated as pLN1-5'hTERT.

(1-2) Cloning of M-XhTERT

The sequences of primer oligonucleotides used in construction of a plasmid vector are shown below.

```
                              (SEQ ID No. 48)
hTERT Fw8-2:    5'-AGT GCC AGC CGA AGT CTG CC-3'

(SEQ ID No. 49)
hTERT 5'XhoIRv3: 5'-GCA GCT GAA CAG TGC CTT C-3'

(SEQ ID No. 50)
hTERT Fw8-1:    5'-AGG ACG CGT GGA CCG AGT GA-3'
```

These primers were prepared based on the nucleotide sequence (Accession No. NM003219) obtained from the GenBank.

Using 0.25 ng of HL-60 cDNA (Marathon-Ready cDNA, CLONTECH) as a template, PCR amplification was performed in 25 µl of a reaction solution containing hTERT Fw8-2 (SEQ ID No. 48) and hTERT 5'XhoIRv3 (SEQ ID No. 49), each having a final concentration of 0.4 µM, using 2.5 units of LA Taq (Takara Shuzo Co., Ltd.). The PCR amplification was performed by placing at 98° C. for 5 minutes, followed by repeating a cycle consisting of reactions at 98° C. for 15 seconds, at 55° C. for 30 seconds, and 72° C. for 90 seconds, 40 times. Furthermore, 1 µl of the PCR product as a template, PCR amplification was performed in 25 µl of a reaction solution containing hTERT Fw8-1 (SEQ ID No. 50) and hTERT 5'XhoIRv3 (SEQ ID No. 49), each having a final concentration of 0.4 µM, using 2.5 units of LA Taq (Takara Shuzo Co., Ltd.). As a thermal cycler, GeneAmp9700 (Applied Biosystems) was used. The PCR amplification was performed by placing at 98° C. for 5 minutes, followed by repeating a cycle consisting of denaturation at 98° C. for 15 seconds, annealing at 55° C. for 30 seconds, and extension at 72° C. for 90 seconds, 40 times. As a result, a DNA fragment of about 1.2 kb was obtained.

The DNA fragment of about 1.2 kb was purified by QIAQUICK PCR Purification Kit (QIAGEN) and both ends thereof were digested with Mlu I and Xho I (Takara Shuzo Co., Ltd.) to obtain cohesive ends, and cloned into a Mlu I-Xho I site of plasmid vector pLN1-EPO2. As a host *Escherichia coli*, XL-10 Gold (STRATAGENE) was used. The nucleotide sequence of the DNA fragment for M-XhTERT insert thus cloned was analyzed by a DNA sequencer (PRISM3700, Applied Biosystems) and confirmed as being identical to the corresponding portion of the nucleotide sequence obtained from the GenBank. From the above, the resultant plasmid vector was designated as pLN1-M-XhTERT.

(1-3) Cloning of 3'-hTERT

The sequences of primer oligonucleotides used in construction of a plasmid vector are shown below.

```
                              (SEQ ID No. 51)
AP1:    5'-CCA TCC TAA TAC GAC TCA CTA TAG GGC-3'
```

As this primer, one which was attached to Marathon-Ready cDNA (CLONTECH) was used.

```
hTERT 3'XhoIFw:
                              (SEQ ID No. 52)
5'-CCG AGC GTC TCA CCT CGA GGG TGA AGG CAC TGT
TC-3' hTERT 3'XhoIFw2:
                              (SEQ ID No. 53)
5'-ATG GAC TAC GTC GTG GGA GCC AGA-3' hTERT Rv1:
                              (SEQ ID No. 54)
5'-GTC GAC GCT AGC TCA GTC CAG GAT GGT CTT GAA
GT-3'
```

These primers were prepared based on the nucleotide sequence (Accession No. NM003219) obtained form the GenBank.

Using 0.1 ng of HL-60 cDNA (Marathon-Ready cDNA, CLONTECH) as a template, PCR amplification was performed in 25 µl of a reaction solution containing hTERT 3'XhoIFw2 (SEQ ID No. 53) and AP1 (SEQ ID No. 51), each having a final concentration of 0.3 µM, using 0.5 unit of KOD-Plus-(Toyobo). As the thermal cycler, GeneAmp9700 (Applied Biosystems) was used. The PCR amplification was performed by placing at 94° C. for 2 minutes, followed by repeating a cycle consisting of denaturation at 94° C. for 15 seconds, annealing at 60° C. for 30 seconds, and extension at 68° C. for 3 minutes, 30 times. Furthermore, using 1 µl of the PCR product as a template, PCR amplification was performed by using hTERT 3'XhoIFw (SEQ ID No. 52) and hTERT Rv1 (SEQ ID No. 54), each having a final concentration of 0.3 µM, by use of 0.5 unit of KOD-Plus-(Toyobo) in 25 µl of a reaction solution. The PCR amplification was performed by placing at 98° C. for 5 minutes, followed by repeating a cycle consisting of denaturation at 98° C. for 15 seconds, annealing at 55° C. for 30 seconds, and extension at 72° C. for 90 seconds, 40 times. As a result, a DNA fragment of about 1.4 kb was obtained.

The DNA fragment of about 1.2 kb was purified by QIAQUICK PCR Purification Kit (QIAGEN) and both ends thereof were digested with Xho I and Sal I (Takara Shuzo Co., Ltd.) to obtain cohesive ends, and cloned into an Xho I site of plasmid vector pLN1-EPO. As a host *Escherichia coli*, XL-10 Gold (STRATAGENE) was used. The nucleotide sequence of the DNA fragment of 3'-hTERT insert thus cloned was analyzed by a DNA sequencer (PRISM3700, Applied Biosystems) and confirmed as being identical to the corresponding portion of the nucleotide sequence obtained from the GenBank and confirmed as being inserted inversely to a transcription direction of CMV promoter on pLN1-EPO. The resultant plasmid vector was designated as pLN1-3' hTERT.

(1-4) Ligation of 5'hTERT, M-XhTRET and 3'hTRET

Using plasmid vector pLN1-3'hTERT obtained in the Section (1-3) above as a template, PCR amplification was performed in 50 µl of a reaction solution containing hTERT 3'XhoIFw (SEQ ID No. 52) and hTERT Rv1 (SEQ ID No. 54), each having a final concentration of 0.3 µM, using 0.5 units of KOD-Plus-(Toyobo). As the thermal cycler, GeneAmp9700 (Applied Biosystems) was used. The PCR amplification was performed by placing at 94° C. for 2 minutes, followed by repeating a cycle consisting of denaturation at 94° C. for 15 seconds, annealing at 60° C. for 30 seconds, and extension at 68° C. for 2 minutes, 30 times. As a result, a DNA fragment of about 1.4 kb was obtained.

The DNA fragment of about 1.4 kb was purified by QIAQUICK PCR Purification Kit (QIAGEN), sequenced by DNA sequencer (PRISM3700, ABI) and confirmed as being identical as the corresponding portion of the nucleotide sequence obtained from the GenBank. Next, the DNA fragment of about 1.4 kb was digested with Xho I and Sal I (Takara Shuzo Co., Ltd.) to obtain cohesive ends. Plasmid vector pLN1-M-XhTERT obtained in Section (1-2) above was cloned, together with the M-XhTERT region obtained by digested with Miu I and Xho I, into a region of the Mlu I-Xho I site of plasmid vector pLN1-EPO2 at which a region containing the human EPO gene was removed. As a host *E coli*, XL-10 Gold (STRATAGENE) was used.

The nucleotide sequence of the inserted DNA fragment in the obtained clone was analyzed by DNA sequencer (PRISM3700, Applied Biosystems). As a result, it was confirmed that the DNA insert had a point mutation caused by a nucleotide replacement in the M-XhTERET region, and had a 3'-hTERT region identical to the corresponding portion of the nucleotide sequence obtained from Genbank, and that the DNA insert was introduced in a forward direction against the transcription direction of CMV promoter on pLN1-EPO. The plasmid vector obtained above was digested with EcoR I and Xho Ito remove the M-XhTERT region. To the region devoid of the M-XhTERT region, CMV promoter, which was obtained by digesting pLN1-5'hTERT obtained in Section (1-1) with EcoR I and Miu I so as to have cohesive ends, and the 5'hTERT region were cloned together with the M-XhTERT region, which was obtained by digesting pLN1-M-XhTERT with Miu I and Xho I so as to obtain cohesive ends. As a host *Escherichia coli*, XL-10 Gold (STRATAGETE) was used. The plasmid vector thus obtained was designated as pLN1-hTERT.

(2) Construction of Plasmid pLN1-EPO-hTERT Expressing Human EPO and hTERT containing loxP Sequence.

A DNA fragment, which contained the CMV promoter obtained by digesting the plasmid vector pLN1-EPO2 prepared in Example 9(1) with EcoR I, and the human EPO gene, and the SV40 poly A additional unit, was cloned into the EcoR I site of the plasmid vector pLN1-hTERT prepared in Example 11. This plasmid was designated as pLN1-EPO-hTERT.

(3) Construction of Plasmid pLN1-EPO2-hTERT for Expressing 2-Copies of Human EPO and hTERT containing loxP Sequence A DNA fragment, which contained 2 copies of the sequence consisting of the CMV promoter obtained by digesting the plasmid vector pLN1-EPO2 prepared in Example 9(1) with EcoR I, the human EPO gene and the SV40 poly A additional unit, was cloned into the EcoR I site of the plasmid vector pLN1-hTERT prepared in Section (1) above. This plasmid was designated as pLN1-EPO2-hTERT.

(4) Construction of pLN1-EPO4-hTERT for Expressing 4-Copies of Human EPO and hTERT containing loxP Sequence.

A DNA fragment, which contained 4 copies of the sequence consisting of the CMV promoter obtained by digesting the plasmid vector pLN1-EPO4 prepared in Example 9(2) with EcoR I, the human EPO gene and the SV40 poly A additional unit, was cloned into the EcoR I site of the plasmid vector pLN1-hTERT prepared in Section (1) above such that the 4 copies were arranged next to each other in the transcription direction. This was designated as pLN1-EPO4-hTERT.

Example 16

Insertion of EPO and hTERT Genes into HAC Vector Derived from Human Chromosome 21

In the same manner as in the human EPO gene described in Example 7, human EPO gene and hTERT gene were inserted into a HAC vector derived from human chromosome 21. As described in Examples 1 to 4 and 6, a HAC vector derived from human chromosome 21 was prepared by deleting a long-arm distal region by telomere truncation, introducing a loxP site into a long-arm proximal region, and deleting a short-arm distal region by telomere truncation. On the other hand, EPO and hTERT expression plasmid containing a lox sequence was prepared. The EPO and hTERT expression plasmid was inserted in the artificial chromosome by site-specific recombination reaction between the loxP sequences by transiently expressing Cre recombinant enzyme. Recombinant fragments having the insert were screened based on whether G418 resistance was acquired or not (reconstitution of a neo gene expression unit by disruption of a promoter).

(1) Transfection and Isolation of G418 Resistant Clone

Mouse A9 cells (A9Δ12 cells) retaining the HAC vector derived from human chromosome 21 obtained in Example 11 were cultured in a single 6-well plastic tissue-culture plate (Falcon) containing a selective medium (10% FBS, DMEM) containing blasticidin (4 µg/ml) to a cell density corresponding to about 60 to 70% saturation. Transfection was performed in the presence of pLN1-EPO-hTERT vector prepared in Example 15 (2) and a Cre enzyme expression vector pBS185 (Lifetech) by use of Fugene 6 (Roche Diagnostics) in accordance with the protocol attached thereto. After culturing was performed for 48 hours, the obtained cells were dispersed with trypsin treatment. The cells from the 6 wells were collectively suspended in a selective medium (DMEM medium supplemented with 10% FBS) containing G418 (600 μg/ml) and seeded in five 48-well plastic tissue-culture plates (Falcon). In 2 to 3 weeks, resistant colonies were formed. The frequency of colony formation was 4 colonies per 5×10$^6$ A9Δ12 cells. The colonies were isolated and further cultured. As a result, a single colony was proliferated. The cells obtained above will be hereinafter referred to as A9ΔET1 cells.

(2) Confirmation of Transferred Chromosome
(2-1) PCR Analysis

A9ΔET1 cells were analyzed. PCR amplification was performed with respect to marker PRED65 and PRED3 genes, which were located in a long-arm proximal region of human chromosome 21 in the vicinity of a loxP site (see, Example 1, (3) and FIG. 2). It was predicted that the human EPO gene insert introduced by site-specific recombination between loxP sequences might have the PRED65 and PRED3 genes. As a result, amplification was performed as predicted. Next, PCR amplification was performed with respect to STS marker D21S275 located in a short-arm proximal region of human chromosome 21 (see Example 6 (3), FIG. 12). Since human chromosome 21 is devoid of a short-arm distal region at the proximal region of the short-arm, it was predicted that D21S275 marker might be present. As a result, it was confirmed that amplification was performed as predicted.

(2-2) Selective Culturing against Drug

Based on whether or not the drug resistant genes present on a HAC vector derived from human chromosome 21, more specifically, a hygromycin resistant gene (short-arm distal region) and blasticidin resistant gene function in the presence of selective drugs, the presence or absence of a region containing each of the drug resistant genes was confirmed to be present.

A9Δ1ET1 cells were cultured in each well of a 6-well culture plate (Falcon) containing a selective medium (10% FBS, DMEM) containing G418 (600 μg/ml) to a cell density corresponding to about 60 to 70% saturation. After rinsed with PBS (Gibco BRL) twice, cells were cultured in a solution containing hygromycin (700 μg/ml, Gibco BRL) alone, a solution containing blasticidin (4 μg/ml) alone, or a solution containing blasticidin, hygromycin, and G418 for one week. The results are shown in Table 16.

TABLE 16

| Name of clone | Brasticidin (Bsd) | Hygromycin (Hyg) |
|---|---|---|
| A9ΔET1 | R | R |

From the above, it was confirmed that A9ΔET1 cells had blasticidin resistance, hygromycin resistance, and G418 resistance.

(2-3) Confirmation of Recombinant having an Insert of Human EPO Gene

A recombinant having an insert, that is, whether or not an insert was introduced into a loxP sequence site on a HAC vector derived from human chromosome 21, was confirmed by PCR amplification where primers were constructed on a sequence derived from a human EPO gene donor vector and on a HAC vector so as to flank the lox P sequence site.

PCR amplification of A9ΔET1 cell was performed by use of Neo Rp2 primer (SEQ ID No. 38) and M13RV primer (SEQ. ID No. 39) derived from plasmid vector pBS226 shown in Example 9 (4). It was predicted that a recombinant having an insert might obtain a fragment of about 2.3 kbp, which includes a region from a portion containing a CMV promoter, human EPO gene, and SV40 poly A additional sequence derived from pLN1-EPO vector, to a loxP sequence, and a region from the loxP sequence to a part of a neo gene derived from pSF1. As a result, it was confirmed that amplification was performed as predicted.

From the above, it was confirmed that A9ΔET1 cell retains the HAC vector derived from human chromosome 21, in which a copy of the insert DNA containing the CMV promoter, human EPO gene and SV40 polyA additional sequence is introduced.

From the experiments (2-1) to (2-3), it was confirmed that A9ΔET1 cell retains a HAC vector derived from human chromosome 21 devoid of the long-arm and the short-arm.

Example 17

Transfer of HAC Vector Derived from Human Chromosome 21 Devoid of the Short-Arm into a Hamster Cell Line (1) Microcell Fusion and Isolation of Drug Resistant Clone As a chromosome donor cell, DT40 cell (DT40(#21)hyg4) retaining a HAC vector derived from human chromosome 21 obtained in Example 6 by deleting a long-arm distal region, inserting a loxP sequence and deleting a short-arm distal region was used. As a chromosome recipient cell, Chinese hamster ovary derived cell line, CHO-K1 (available from ATCC, Accession No. JCRB9018) was used. Preparation of microcells and fusion with the CHO cells were performed in the same manner as in Example 3 (1). Cell fusion was performed 4 times, 5 hygromycin resistant CHO clones were obtained after about 2 weeks from initiation of selective culturing.

(2) Confirmation of Transferred Chromosome
(2-1) PCR Method

The PCR method was performed to confirm the presence of a transferred chromosome. More specifically, the presence or absence of markers pCHB, D21S187, and D21S275 (Example 6 (3-1), FIG. 12) located at a short-arm proximal region of human chromosome 21 were detected. It was confirmed that D21S275 located at the proximal region from a deletion site was amplified in 2 out of 5 hygromycin resistant CHO cell clones (CHO#21hyg4 and CHO#21hyg8).

(2-2) PCR Method

The sequences flanking with a recombination target site were amplified (see Example 6, (3-3), FIG. 12). An amplified product was obtained only in 2 clones of CHO#21hyg4 and CHO#21hyg8. Also, it was confirmed that a partial fragment was generated as predicted from digestion with restriction enzyme Nsi I.

(2-3) Fluorescence in situ Hybridization (FISH)

FISH analysis was performed using a human specific probe Cot1 (Gibco BRL) in accordance with the method described in Matsubara et al. (FISH experimental protocol, Shujunsha, 1994). Two clones (CHO#21hyg4 and CHO#21hyg8) of the hygromycin resistant CHO clones were analyzed. As a result, truncated human chromosome 21 was detected in almost all the mitotic images observed. Based on relative comparison with the chromosome of the host CHO cell in size, it was confirmed that truncated human chromosome 21 was transferred into the CHO cell.

From the experiments of (1) and (2) above, it was confirmed that a hygromycin resistant CHO clone has a partial fragment (HAC vector) derived from human chromosome 21, obtained by deleting a long-arm distal region, inserting a loxP sequence, and deleting the short-arm distal region.

Example 18

Transfer of HAC Vector Derived from Human Chromosome 21 Devoid of a Short-Arm Distal Region into Human Cell Line and Confirmation of Stability (1) Microcell Fusion and Isolation of Drug Resistant Clone As a chromosome donor cell, CHO cells (CHO(#21)hyg4 and CHO(#21)hyg8) retaining a HAC vector derived from human chromosome 21 obtained in Example 17 by deleting a long-arm distal region, inserting a loxP sequence and deleting a short-arm distal region. As a chromosome recipient cell, human fibrosarcoma cell line HT1080 (obtained from ATCC, Accession No. CCL-121) was used. Preparation of microcells and fusion with the HT1080 cells were performed in the same manner as in Example 4 (1). Cell fusion was performed once in the case of CHO(#21)hyg4, with the result that 7 blasticidin resistant HT1080 clones in total were obtained. Cell fusion was performed twice in the case of CHO(#21)hyg8, with the result that 20 blasticidin resistant HT1080 clones were obtained.

(2) Confirmation of Transferred Chromosome (2-1) PCR Method

Whether a chromosome was transferred or not was confirmed by the PCR amplification of a blasticidin resistant gene (see Example 4, (2-1)) and a hygromycin resistant gene. The sequences of oligonucleotide primers used herein are shown below:

```
HygroF:   5'-GCGAAGAATCTCGTGCTTTC;  (SEQ ID No. 55)

HygroR:   5'-ATAGGTCAGGCTCTCGCTGA.  (SEQ ID No. 56)
```

It was confirmed that a blasticidin resistant gene was amplified in all blasticidin resistant HT1080 clones. On the other hand, it was confirmed that a hygromycin resistant gene was amplified in 5 out of 7 CHO(#21)hyg4 clones and 27 out of 30 CHO(#21)hyg8 clones.

(2-2) Chromosome Analysis

Figure 17:
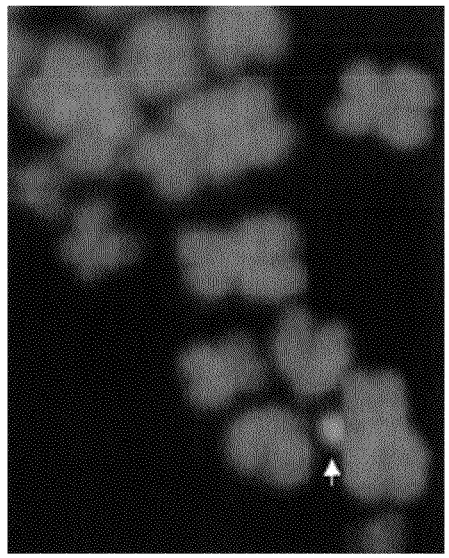
FIG. 17 is a photograph showing the results of FISH analysis indicating the retention of a human chromosome 21 fragment (arrow) in the blasticidin resistant HT1080 cell clone.

Chromosome was analyzed by FISH analysis using a human specific probe Cot1 (Gibco BRL) in accordance with the method described in Matsubara et al. (FISH experimental protocol, Shujunsha, 1994). Representative FISH images are shown in FIG. 17. In the case of blasticidin resistant clones, a chromosomal fragment, which was smaller than endogenous chromosome 21 and not observed in a parent HT1080 cell, was observed.

From the experiments (1) and (2) above, it was confirmed that blasticidin resistant HT1080 clone retains a human chromosome partial fragment (HAC vector) prepared by deleting a long-arm distal region, inserting a loxP sequence and deleting a short-arm distal region thereof.

(3) Long-Term Subculture under Nonselective Culture Conditions

To confirm the stability of human chromosome 21 where a long-arm distal region was deleted, and human chromosome 21 where a short-arm distal region was deleted in a cultured cell, long-term subculture was performed under nonselective culture conditions by using the human cell clones (HT1080 (#21)bsd79-1-1, 3, 6, 11, 14; HT1080(#21)bsd-H4-1, 3, 6; HT1080(#21)bsd-H8-4, 9, 2) used in Example 4. As the nonselective culture solution for the human cell clones, DMEM supplemented with 10% CS was used. A selective culture solution was prepared by adding 4 µg/ml blasticidin to the nonselective culture solution. For the human cell clones, $5.0 \times 10^5$ cells were seeded in a 10 cm-diameter dish. Three days later, the number of cells was determined and $5.0 \times 10^5$ cells were again seeded in a 10 cm-diameter dish. The human cell clones were collected at every cell population doubling level, that is, to 25, 50,100 levels, and chromosomal preparations were prepared.

(4) Chromosome Analysis

An artificial chromosome was detected in a human cell by Giemsa staining in accordance with the method described in Kuroki et al. (Cell engineering handbook, Yodosha, 1992). In about 20 metaphase chromosomal images, the presence or absence of a mini chromosome was observed to calculate a retention rate. Average retention rate of the mini chromosome of 5 clones was obtained. The results are shown in Table 17.

TABLE 17

Stability of #21HAC in HT1080 cell

| HAC | Cell population doubling level | Retention rate of HAC (%) | |
|---|---|---|---|
| | | non-selective with drug | selective with drug |
| #21ΔqHAC | 50 | 98 | 99 |
| | 100 | 95 | 97 |
| #21ΔpqHAC | 25 | 76 | 79 |
| | 50 | 85 | 88 |
| | 100 | 83 | 79 |

A human chromosome 21 partial fragment was stably retained in HT1080 cells on 100th time of cell division. Furthermore, when a chromosomal image during the metaphase was observed, 1 to 2 partial chromosome per cell were observed.

From the experiments (3) and (4) above, it was confirmed that a partial fragment of human chromosome 21 prepared by deleting a long-arm distal region and a partial fragment of human chromosome prepared by deleting a short-arm distal region can be stably retained in a HT1080 cell clone in non-selective culture conditions, and that the copy number of such chromosomes per cell are maintained.

Example 19

Insertion of GFP Gene into HAC Vector Derived from Human Chromosome 21 into Human Cell Clones (1) Transfection and Isolation of G418 Resistant Clone Human HT 1080 cell clones (HT1080(#21)bsd79-1-6, 14; HT1080(#21)bsd-H4-1, 6; HT1080(#21)bsd-H8-2) retaining a HAC vector derived from human chromosome 21 and prepared in Example 18 were treated with trypsin and seeded in 6-well cluster (Nunc) with a density of $4 \times 10^5$ cells per well and cultured for a day. Two µg of a GFP expression plasmid containing a loxP sequence and prepared in Example 5 (1) and 1 µg of Cre enzyme expression vector pBS 185 (Lifetech) were mixed with 7.5 µl of liposome solution (Lipofectamine2000, Invitrogen). The resultant solution was added to a medium and the medium was exchanged after 5 hours. After culturing was performed for one day, trypsinization was performed. The cells were suspended in DMEM medium supplemented with 10% CS and seeded in two 10 mm-dishes. Next day, the medium was replaced with a medium containing 400 µg/ml of G418 (GENETICIN, Sigma). In about 2 weeks, resistant colonies were formed. The frequency of colony formation was 3 to 14 colonies per $4 \times 10^5$ HT1080 cells. Colonies were isolated, proliferated and subjected to the following analysis.

(2) Expression of GFP Gene Inserted into HAC Vector Derived from Human Chromosome 21

Figure 18:
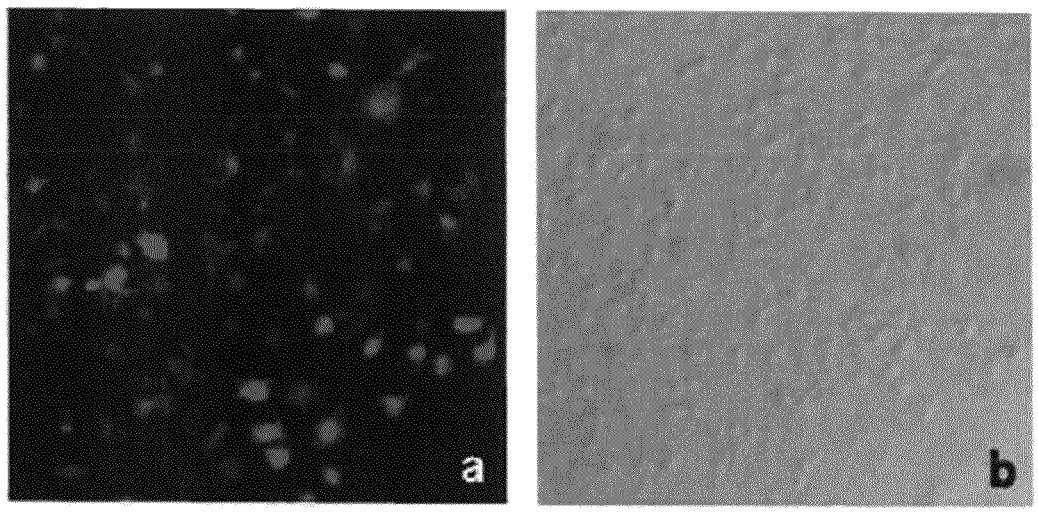
FIGS. 18a and 18b are fluorescence (FIG. 18a) and phase-contrast (FIG. 18b) microscope photographs showing GFP expression in the G418 resistant HT1080 clone.

The isolated G418 resistant HT1080 cell clones were observed by a fluorescent microscope. As a result, it was confirmed that GFP was expressed in 14 out of 21 clones in the case of 21ΔqHAC, and 28 out of 31 clones in the case of 21ΔpqHAC. A representative fluorescent microscopic image and an optical microscopic image are shown in FIGS. 18a and 18b.

(3) Confirmation of Homologous Recombinant

To confirm a homologous recombinant, sequences flanking with a recombinant target site were amplified by PCR. The sequences of primer oligonucleotides designing on pBS226 and pSF1 plasmids are shown below:

CMVneo689:  5'-GCCATCCACGCTGTTTTGAC (SEQ ID No. 57)

CMVneo910:  5'-GCATCAGAGCAGCCGATTGT (SEQ ID No. 58)

Despite expression of a GFP gene, PCR amplification was observed in all G418 resistant clones. Thus, all clones were conformed to be homologous recombinants From the experiments (1) to (3), it was confirmed that a gene can be inserted into a HAC vector derived from human chromosome 21 in a human cell clone, and that the gene having an insert can be expressed.

(4) Expression of GFP Gene after Long-Term Subculture

Seven clones were randomly picked up from G418 resistant HT1080 cell clones and subjected to subculture in the absence of a selective drug. A month (cell population doubling level: 30) after initiation of culturing, expression of a GFP gene was observed in each of the clones.

From the experiment (4), it was confirmed that a gene inserted in a HAC vector derived from human chromosome 21 can maintain the expression without being attenuated by positional effect of the insertion site. More specifically, it was found that the gene insertion site on the HAC vector was not a heterochromatin region.

Example 20

Transfer of HAC Vector Derived from Human Chromosome 21 into Mouse ES Cell Line and Confirmation of Stability (1) Microcell Fusion and Isolation of Drug-Resistant Clone As a chromosome donor cell, CHO cell clone (CHO(#21) ΔqGFP7-2) retaining a HAC vector derived from human chromosome 21, obtained in Example 5 by deleting a long-arm distal region and inserting a loxP sequence, with a GFP gene inserted; and CHO cell clone (CHO(#21)Hyg8) retaining a HAC vector derived from human chromosome 21 obtained in Example 17 by deleting a long-arm distal region, inserting a loxP sequence, and deleting a short-arm distal region were used. As a chromosome recipient cell, mouse ES cell line E14 (Hooper et al., Nature, 326:292, 1987) was used. E14 cells were cultured in accordance with the method described in (Shinichi Aizawa, biomanual series 8, gene targeting, Yodosha, 1995) by use of mouse embryo primary cultured cells (Invitrogen) treated with mitomycin C as nursing cells. First of all, microcells were prepared from about $10^8$ donor cells and suspended in 5 ml of DMEM in total. About $10^7$ E14 cells were washed with DMEM three times and suspended in 5 ml of DMEM, and thereafter, mixed with the microcells and subjected to centrifugation at 1250 rpm for 10 minutes. The supernatant was removed and the precipitate was properly loosened by tapping. To this, 0.5 ml of 1:1.4 PEG solution (dissolving 5 g of PEG 1000 (Wako Pure Chemical Industries, Ltd.) and 1 ml of DMSO (Sigma) dissolved in 6 ml of DMEM) was added and allowed to stand still at room temperature for 1.5 minutes. To the resultant mixture, 10 ml of DMEM was gently added. Immediately, the mixture was centrifuged at 1250 rpm, for 10 minutes. After the supernatant was removed, the precipitate was suspended in 30 ml of medium for ES cells and seeded in three 100 ml-diameter plastic tissue-culture plates (Falcon). After 24 hours, the medium was exchanged with a medium supplemented with 300 µg/ml of G418 (GENETICIN, Sigma) in the case where CHO cell clone, CHO(#21)ΔqGFP7-2 was used as the donor cell; and exchanged with a medium supplemented with 150 µg/ml of hygromycin (Wako Pure Chemical Industries, Ltd.) in the case where CHO cell clone, CHO(#21)Hyg8 was used as the donor cell. Everyday after that, medium was exchanged with a fresh one. Resistant colonies were formed in a week to 10 days. The frequency of colony formation was 2 to 5 colonies per $10^7$ E14 cells. Colonies were isolated, proliferated, suspended in 1 ml per $5 \times 10^7$ colonies of a preservation medium (a medium for ES cells+10% DMSO (Sigma)) and frozen at −80° C. Simultaneously, genome DNA was prepared from about $10^6$ cells of each of the resistant clones (Puregene DNA Isolation kit (Gentra System)).

(2) PCR Analysis

A transferred chromosome and a region contained in the chromosome were confirmed by PCR amplification. The following primer oligonucleotides were newly designed.

21p76957:  5'-ACACTTTTGACAAACACACCAG(SEQ ID No. 59)

21p77555:  5'-TCAACAATGAAAGGGGATGTC (SEQ ID No. 60)

These primers were prepared based on the nucleotide sequence (Accession No. AL163201) obtained from the GenBank. The oligonucleotide primers used in the analysis are shown in Table 18 below.

TABLE 18

| Name of markers | Oligonucleotides | SEQ ID Nos. | Examples |
|---|---|---|---|
| pCHB | | | 6(3-1) |
| D21S187 | | | 6(3-1) |
| | #21p76957/#21p77555 | 39/40 | Present Example |
| | HygroF/HygroR | 35/36 | 18(2-1) |
| | Hyg968/#21p96705 | 27/28 | 6(3-3) |
| | #21p91203/#21p91976 | 25/26 | 6(3-2) |
| | Spe31203/Bam36192 | 23/24 | 6(1) |
| D21S275 | | | 6(3-1) |
| | PRED65F/PRED65R | 3/4 | 1(3-1) |
| | PRED3F/PRED3R | 5/6 | 1(3-1) |
| | #21qEcoF/#21qEcoR | 9/10 | 2(1) |
| | Left455F/Left638R | 15/16 | 2(3-2) |
| | Right958F/Right1152R | 17/18 | 2(3-2) |
| | #21qBaF/#21qBaR | 11/12 | 2(1) |

The results above are shown in FIG. 19. The drug resistant clones obtained were deficient in a part of the region of the transferred chromosome.

(3) Fluorescence in situ Hybridization (FISH)

Figure 20:
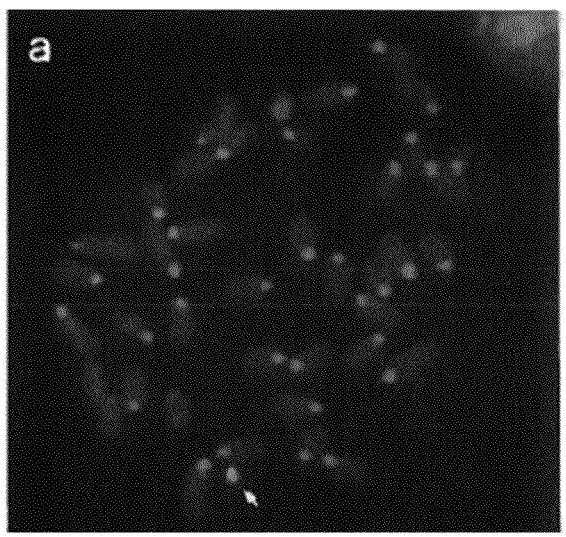
FIGS. 20a and 20b are photographs showing the results of FISH analysis indicating the retention of a human chromosome 21 fragment in the drug resistant E14 cell clone.
Figure 20:
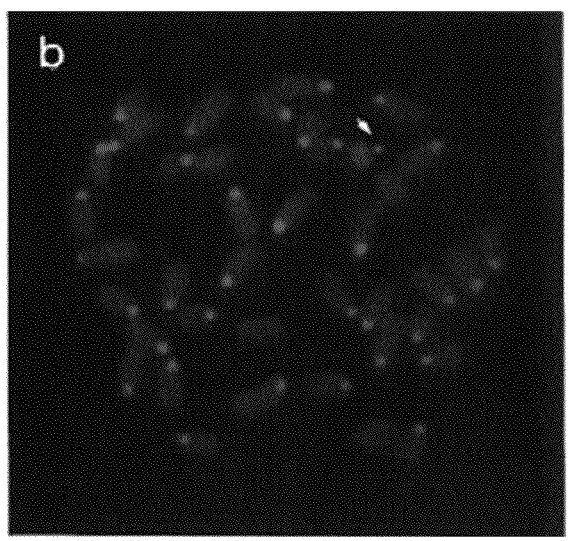

FISH analysis was performed using a human specific probe Cot1 (Gibco BRL) in accordance with the method described in Matsubara et al. (FISH experimental protocol, Shujunsha, 1994). As a result, truncated human chromosome 21 was detected in almost all the mitotic images observed. Representative FISH images are shown in FIGS. 20a and 20b. A human chromosome fragment was observed in one (E14(#21)neo1) out of five G418 resistant clones derived from CHO(#21)

ΔqGFP7-2, whereas it was observed in two of hygromycin resistant clones derived from CHO(#21)Hyg8. Of them, two human chromosome fragments were observed in E14(#21)Hyg1 and one human chromosome fragment was observed in E14(#21)Hyg2. The aforementioned 3 clones where a human chromosome was observed, was confirmed to have the normal number (40) of chromosomes which can be found in mouse.

From the results of (2) and (3) above, it was confirmed that G418 resistant or hygromycin resistant E14 clone retained a HAC vector derived from human chromosome 21.

(4) Long-Term Subculture Under Nonselective Culture Conditions

To confirm the stability of a HAC vector derived from human chromosome 21 in mouse ES cells, selective culture was performed under nonselective culture conditions. The aforementioned human cell clones E14(#21)neo1, E14(#21)Hyg1, E14(#21)Hyg2 prepared in Section (3) above were used. As the nonselective culture solution for the mouse ES cells, DMEM containing 18.2% FBS (Invitrogen), 3.5 g/l glucose (Sigma), 0.125 mM MEM nonessential amino acid (Invitrogen), 1000 U/ml LIF (ESGRO, Wako Pure Chemical Industries, Ltd.), and 0.1 mM 2-mercaptoethanol (Sigma) was used. $1 \times 10^7$ cells of mouse ES cell line were seeded on nursing cells in a 10 cm-diameter dish. Two days later, 1/15th of the cells was seeded on the nursing cells in a 10 cm-diameter dish. The cells were collected at 14, 28 and 42 days after initiation of culturing and chromosomal preparations were prepared.

(5) Chromosome Analysis

Detection of a HAC vector derived from human chromosome 21 in a mouse ES cell was performed by FISH analysis using a human specific probe Cot1 (Gibco BRL) in accordance with the method described in Matsubara et al. (FISH experimental protocol, Shujunsha, 1994). The presence or absence of a human chromosome fragment was checked in 200 metaphase images and a retention rate of the human chromosome was calculated. The results are shown in Table 19. Long-term subculture was performed in triplicate with respect to each clone and its retention rate is shown in average.

TABLE 19

| Cell clones | Cell population doubling level (Accumulated) | HAC retention rate % (2 copies/1 copy) |
|---|---|---|
| E14(#21)neo1 | 0 | 80(0/80) |
| | 25 | 57(0/57) |
| | 50 | 51(0/51) |
| | 75 | 48(0/48) |
| E14(#21)Hyg1 | 0 | 98(73/25) |
| | 25 | 95(60/35) |
| | 50 | 92(57/35) |
| | 75 | 89 |
| E14(#21)Hyg2 | 0 | 98(0/98) |
| | 25 | 96(0/96) |
| | 50 | 92(0/92) |
| | 75 | 89(0/89) |

A partial fragment prepared by deleting a long-arm distal region from human chromosome 21 tends to decrease with the progress of long-term subculture under nonselective conditions. In contrast, a partial fragment prepared by deleting both a long-arm distal region and a short-arm distal region from human chromosome 21, was stably maintained without decreasing even if cell divisions were occurred in excess of 75 times. Furthermore, in a clone where the copy number of chromosome fragments was 1 per cell at the time long-term subculture was initiated, the copy number did not increase. In a clone dominantly having 2 copies of fragments per cell at the time long-term subculture was initiated, the number of copies was likely to decrease slightly.

From the experiments of (4) and (5) above, it was clarified that a partial fragment prepared by deleting a long-arm distal region and a short-arm distal region from human chromosome 21 can be retained stably in a mouse ES cell line under nonselective culture conditions, and that the copy number of partial fragments per cell can be maintained.

Example 21

Transfer of HAC Vector Derived from Human Chromosome 21 into Human Stem Cell and Confirmation of Stability (1) Microcell Fusion and Isolation of Drug Resistant Clone As a chromosome donor cell, CHO cell clones (CHO(#21)hyg4 and CHO(#21)hyg 8) retaining a HAC vector derived from human chromosome 21 obtained in Example 17 by deleting a long-arm distal region, inserting a loxP sequence, and deleting a short-arm distal region. As a chromosome recipient cell, human bone marrow-derived mesenchymal stem cell line, hiMSC (obtained from Prof Junya Toguchida, Kyoto University, Okamoto et al., Biochem. Biophys. Res. Commun., 295: 354, 2002) which was established by a human hTERT gene and a human papilloma virus E6/E7 gene, was used. The hiMSC line was cultured by use of DMEM medium supplemented with 10% FBS. First of all, microcells were prepared from about $10^7$ CHO(#21)hyg4/8 cells. More specifically, CHO(#21)hyg4/8 cells, which were cultured in six 25 cm²-centrifugation flasks (Coasters) up to a cell density corresponding to about 60 to 70% saturation, were further cultured in a culture solution (10% FBS, 8 μg/ml blasticidin, F12) containing colcemid (0.075 μg/ml, Demecolcine, Wako Pure Chemical Industries, Ltd.) for 48 hours to induce micronuclei. After the medium was removed, each of the centrifugation flasks was filled with a pre-heated (37° C.) solution of cytochalasin B (10 μg/ml in DMEM, Sigma), inserted in an acrylic centrifugation vessel, and centrifuged (34° C., 8000 rpm) for one hour. Microcells were recovered by suspending them in a serum-free medium (DMEM) and purified by filtration. To a 6 cm-diameter dish (Falcon) in which hiMSC cells were cultured up to 80% saturation, the purified micronucleus cells were added. The cells were fused with a PEG solution. After 48 hours, the cells were dispersed by trypsin treatment, and cultured in a selective medium (10% CS, DMEM) containing blasticidin (8 μg/ml). After selective culturing was performed for about 2 weeks, formed drug resistant colonies were isolated and subjected to the following analysis. In the case of CHO(#21)hyg4, one clone of blasticidin resistant hiMSC was obtained. In the case of CHO(#21)hyg8, 4 clones of blasticidin resistant hiMSC were obtained.

(2) Confirmation of Transferred Chromosome (2-1) PCR Method

A transferred chromosome was confirmed by PCR amplification of a blasticidin resistant gene (see Example 4 (2-1)) and hygromycin resistant gene (see Example 18 (2-1)). Both of the blasticidin resistant gene and the hygromycin resistant gene were confirmed to be amplified in 5 blasticidin resistant HT1080 clones.

(2-2) Chromosome Analysis

Figure 21:
FIG. 21 is a photograph showing the results of FISH analysis indicating the retention of a human chromosome 21 fragment (arrow) in the drug resistant hiMSC cell clone.

Chromosome analysis was performed by the FISH method using a human specific probe Cot1 (Gibco BRL) in accordance with the method described in Matsubara et al. (FISH experimental protocol, Shujunsha, 1994). A representative FISH image is shown in FIG. 21. In the case of a blasticidin resistant clone, a chromosomal fragment, which is smaller than endogenous chromosome 21 and not observed in a parent hiMSC cell, was observed.

From the experiments (1) and (2) above, it was confirmed that the blasticidin resistant hiMSC clone retains a human chromosome 21 partial fragment (HAC vector) prepared by deleting a long-arm distal region, inserting a lox P sequence, and deleting a short-arm distal region.

(3) Long-Term Subculture Under Nonselective Culture Conditions

To confirm the stability of a HAC vector derived from human chromosome 21 in somatic stem cells having multipotency, long-term subculture was performed under nonselective culture conditions. The aforementioned human mesenchymal cell clones (hiMSC(#21)bsd-H4-1, hiMSC(#21) bsd-H8-1, 2, 3, 4) prepared in Sections (1) and (2) above were used. As the nonselective culture solution for the human cell clone, DMEM containing 10% FBS was used. The selective culture solution was prepared by adding 4 µg/ml blasticidin to the nonselective culture solution. Human cell clones ($5.0 \times 10^5$ cells) were seeded in a 10 cm-diameter dish. Three days later, the number of cells were determined and again $5.0 \times 10^5$ cells of human cell clone were seeded in a 10 cm-diameter dish. Cells were collected at the time points when the cell population doubling level reached 15, 40 and 90 from initiation of culturing and chromosome samples were prepared.

(4) Chromosome Analysis

Detection of a HAC vector derived from human chromosome 21 in human mesenchymal cells was performed by the FISH method in accordance with the method described in Matsubara et al. (FISH experimental protocol, Shujunsha, 1994) and using alphoid specific probe p11-4 (obtained from Prof. Hiroshi Masumoto, Nagoya University, Ikeno et al., Hum. Mol. Genet., 3: 1245, 1994) derived from human chromosome 21. The presence or absence of a fluorescent signal on a mini chromosome was checked in 50 metaphase images to calculate a retention rate. The results are shown in Table 20.

TABLE 20

Stability of #21HAC in hiMSC cell

| Cell clones | Selection with drug | Retention rate % |  |  |  |
|---|---|---|---|---|---|
|  |  | 0 PDL | 15 PDL | 40 PDL | 90 PDL |
| HiMSC(#21)-H4-1 | + | 96 | 92 | 94 | 88 |
|  | − |  | 82 | 77 | 65 |
| HiMSC(#21)-H8-1 | + | 100 | 98 | 98 | 95 |
|  | − |  | 75 | 73 | 84 |
| HiMSC(#21)-H8-2 | + | 87 | 82 | 82 | 80 |
|  | − |  | 80 | 77 | 80 |
| HiMSC(#21)-H8-3 | + | 100 | 89 | 94 | 90 |
|  | − |  | 87 | 88 | 80 |
| HiMSC(#21)-H8-4 | + | 89 | 87 | 88 | 90 |
|  | − |  | 75 | 77 | 80 |

A human chromosome 21 partial fragment was retained stably in the hiMSC cell on the 90th time of cell division. When a chromosome image during the metaphase was observed, a single copy of a partial chromosome fragment per cell was found.

From the sections (3) and (4) above, it was clarified that a HAC vector derived from human chromosome 21 can be retained in the hiMSC cell stably under nonselective culture conditions and the number of copies per cell can be maintained.

Example 22

Confirmation of Multipotency of Human Somatic Stem Cell Retaining HAC Vector Derived from Human Chromosome 21 Transferred, by in-vitro Induced Differentiation Induced differentiation of the human mesenchymal stem cells to which a HAC vector derived from human chromosome 21 prepared in Example 21 was transferred, was performed in accordance with the method of Okamoto et al. (Biochem. Biophys. Res. Commun., 295: 354, 2002) and then the differentiation potency of the stem cells into bone, cartilage, and adipose cells was confirmed. In this example, the human mesenchymal stem cell clone (hiMSC(#21)bsd-H8-1) described in Example 21 and its parent cell line (hiMSC) were used.

(1) Induced Differentiation into Bone Cells

The hiMSC cells were seeded with a density of $3 \times 10^3/cm^2$ and cultured in DMEM medium containing 10% FBS and supplemented with 100 nM dexamethasone (Sigma), 50 µM ascorbic acid 2-phosphate (Sigma), and 10 mM β-glycerophosphoric acid (Sigma) for 21 days. During the culture, the medium was exchanged with a fresh one every 2 days.

(2) Induced Differentiation into Cartilage Cells

First, $2.5 \times 10^5$ of hiMSC cells were collected in a 15 ml-polypropylene tube (Corning) and centrifuged at 800 rpm and room temperature for 5 minutes. The cell precipitation was resuspended in a high glucose DMEM medium supplemented with 10 ng/ml human TGF-β3(Invitrogen), 100 nM dexamethasone (Sigma), 6 µg/ml insulin (Roche), 100 µM ascorbic acid 2-phophate (Sigma), 1 mM sodium pyruvate (Sigma), 6 µg/ml transferrin (Sigma), 0.35 mM proline (Sigma), and 1.25 mg/ml bovine serum albumin (Invitrogen), followed by subjecting to centrifugation. Cells were cultured for 21 days in the state of cell aggregation. During the culture, the medium was exchanged with a fresh one every 2 days.

(3) Induced Differentiation into Adipose Cells

First, hiMSC cells were seeded with a density of $3 \times 10^3/cm^2$ in a culture dish. After cells were cultured up to confluency, culture for induction and maintenance were repeated three times. The induction culture was performed in an induction medium, DMEM containing 10% FBS and supplemented with 1 µM dexamethasone (Sigma), 0.2 mM indomethacin (Sigma), 10 µg/ml insulin (Sigma), and 0.5 mM 3-isobutyl-1-methylxanthine (Sigma), for 3 days. Maintenance culture was performed in DMEM medium containing 10% FBS supplemented with 10 µg/ml insulin (Roche) for 2 days.

(4) Tissue Staining

After culturing was performed for 21 days, the cells were washed with PBS twice and fixed with 10% formalin. In the case of bone cell differentiation, 5% silver nitrate (Nakarai) was used for staining In the case of adipose cell differentiation, 0.3% oil red O (Nakarai) was used in staining In the case of cartilage cell differentiation, the fixed cell aggregation was dehydrated with ethanol, washed with xylene, embedded in paraffin, and sliced into pieces. The cut pieces were stained with Alcian blue (Nakarai).

When the mesenchymal stem cell line, hiMSC(#21)bsd-H8-1, retaining a HAC vector derived from human chromosome 21 transferred therein was subjected to induced differentiation, it showed positive results to tissue staining specific to bone, cartilage and adipose cells, similarly to the case of its parent cells, hiMSC.

From the experimental results (1) to (4) above, it was confirmed that the mesenchymal stem cells retaining a HAC vector derived from human chromosome 21 transferred therein keep multipotency to bone, cartilage and adipose cells.

Example 23

Introduction of Human Chromosome 14 Fragment into ES Cell of Cynomolgus Monkey

As a chromosome donor cell, mouse A9 cell line (hereinafter referred to as "A9/SC20") carrying a human chromosome 14 fragment SC20 (Tomizuka et al., Proc. Natl. Acad. Sci. USA, 97, 722-727, 2000) was used. As a chromosome recipient cell, cynomolgus monkey ES cell line, CMK6.4 (Suemori et al., Dev. Dyn. 222, 273-279, 2001) was used. CMK6.4 cells were cultured in accordance with a method described in Suemori et al. (supra). The medium was composed of DMEM/F12 (Sigma D-6421) supplemented with 20% KSR (Knock out serum replacement, GIBCO BRL), nonessential amino acid solution (×100, Sigma, M7145) and L-glutamine solution (×100, Sigma, M7522). First, microcells were prepared from A9/SC20 cells cultured in twenty four 25 cm$^2$-flasks (Nunc 152094) to a 70 to 80% confluent, in accordance with the method reported by Shimizu et al. (Cell engineering handbook, Yodosha, 1992). The total amount of the obtained microcells was suspended in 5 ml of DMEM (Sigma, D-5796). After 1 to 5×10$^6$ of CMK6.4 cells were dispersed with a trypsin solution (0.25% trypsin, 20% KSR), they were washed with DMEM twice, suspended in 5 ml of DMEM, combined with the microcells, and centrifuged at 1500 rpm for 7 minutes, and then the supernatant was removed. A solution to be used for cell fusion, 1:1.4 PEG solution, was prepared by dissolving 1 g of PEG (Sigma) in 1.2 ml of DMEM and adding 0.2 ml DMSO (Sigma) to the resultant solution. The precipitate was loosened by tapping. To this, 1.0 ml of 1:1.4 PEG solution preincubated at 37° C. was added and the resultant solution was allowed to stand still at room temperature for 2 minutes, and then 10 ml of DMEM was gently added to the solution. Immediately, the mixture was centrifuged at 1,500 rpm for 7 minutes. After the supernatant was removed, the precipitate was suspended in 4 ml of a medium for ES cells and seeded in two 35 mm-diameter plastic tissue-culture plates in which G418 resistant nursing cells were previously seeded and incubated in a CO$_2$ incubator (37° C., 5% CO$_2$). After 24 hours, the medium was exchanged with a medium supplemented with 50 μg/ml G418. Following then, the medium was exchanged with a fresh one every day. In one week to 10 days, drug resistant colonies were formed. Drug resistant ES cell colonies were picked up, seeded in a 4-well plate in which G418 resistant nursing cells were previously seeded, and cultured for 10 days in the presence of 50 μg/ml G418. The resulting ES cell colonies survived were picked up again, seeded in a 4-well plate in which nursing cells were previously seeded, and cultured for a further 10 days under nonselective conditions. It was demonstrated that the ES cells proliferated was positive to alkali phosphatase staining (Suemori et al., supra) and maintained undifferentiated potency. Furthermore, genomic DNA was extracted in accordance with a standard method and whether or not the inserted chromosome is present was confirmed as follows.

Using genomic DNA of the drug resistance clone as a template, the presence of a Neo gene contained in the human chromosome 14 fragment (pSTneoB, Tomizuka et al., Nature Genet. 16, 133-143, 1997) was detected by the PCR method. The nucleotide sequences of primer oligonucleotides used herein are shown below. Using about 0.1 μg of genomic DNA as a template and Takara Ex Taq was used as Taq polymerase, PCR was performed by carrying out a cycle of a reaction at 94° C. for 5 minutes and repeating a cycle consisting of reactions at 94° C. for 15 seconds, 59° C. for 15 seconds, and 72° C. for 20 seconds, 35 times.

neoF:   TGAATGAACTGCAGGACGAG   (SEQ ID No. 61)

neoR:   ATACTTTCTCGGCAGGAGCA   (SEQ ID No. 62)

One clone of the obtained G418 resistant monkey ES cell clones was subjected to PCR analysis. As a result, a specific amplification product indicative of the presence of the Neo gene (PSTneoB), was detected. From these experiments, it was demonstrated that human chromosome 14 fragment SC20 was transferred to the cynomolgus monkey ES cell line by the microcell method. It is known that the characteristics of the ES cells of primates including cynomolgus monkey, Rhesus monkey, and human are very similar to each other (Suemori et al., Experimental Medicine, Vol. 21, No. 8, p 46-51, 2003, Yodosha). Therefore, this results show that a human chromosome and human artificial chromosome (HAC) labeled with a drug resistance marker can be introduced into a primate ES cell including a cynomolgus monkey ES cell by the method described in this Example.

Example 24

Confirmation of Differentiation Potency of Mouse ES Cell Clone Retaining HAC Vector Derived from Human Chromosome 21 Transferred therein An attempt was made to differentiate the mouse ES cells, which was prepared in Example 20 by transferring a HAC vector derived from human chromosome 21 having a GFP gene insert thereto, into nerve cells and the differentiation potency to the nerve cells was determined. As the mouse ES cells, mouse ES cell line E14 (#21) neol described in Example 20, was used.

(1) Preparative Isolation of GFP-Expressing Cells

E14(#21) neol cells were seeded on mouse embryo primary culture cells (Invitrogen) treated with mitomycin C in a 100 mm-diameter plastic tissue-culture plate and cultured in DMEM containing 20% FBS and supplemented with 2 mM L-glutaminic acid (Invitrogen), 0.2 mM 2-mercaptoethanol (Sigma), 1 mM sodium pyruvate (Invitrogen), 0.1 mM MEM nonessential amino acid, and 1,000 U/ml LIF (Wako Pure Chemical Industries, Ltd.) The cells were dispersed by treating them with 0.1% trypsin and 0.04% EDTA and collected in a medium, washed with PBS twice, suspended in PBS so as to obtain a density of 1×10$^6$ cells/ml, and subjected to a cell sorter (EPICS ELITE, Beckman coulter) to select GFP-expressing cells.

(2) Induced Differentiation into Nerve Cell

Figure 22:
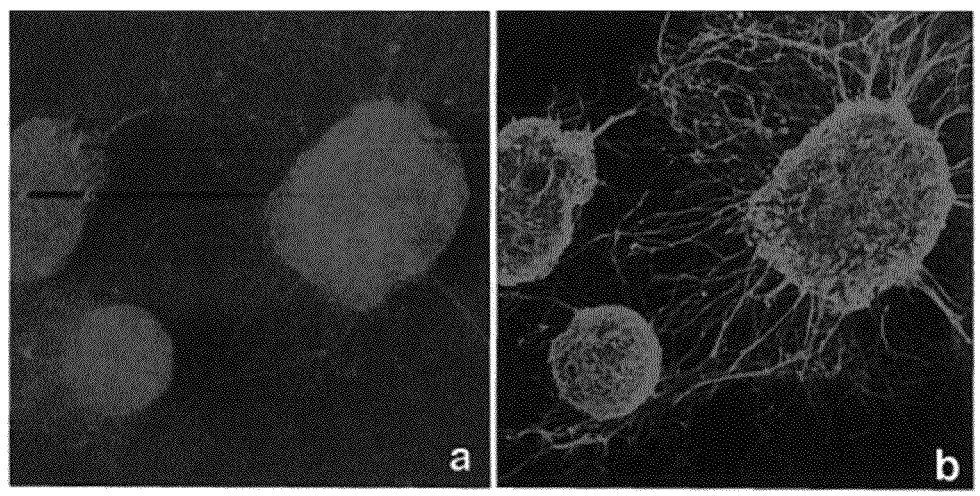
FIGS. 22a and 22b are fluorescence microscope photographs showing GFP expression (FIG. 22a) and staining with anti-beta tubulin antibody (FIG. 22b) when ES cells retaining HAC were induced to differentiate into nerve cells in vitro.

PA 6 cells derived from the mouse bone marrow serving as nursing cells for use in induced differentiation were cultured in a medium of αMEM (Invitrogen) containing 10% FBS and supplemented with 2 mM L-glutaminic acid (Invitrogen). 1×10$^3$ cells of GFP-expressing ES cells selected in Section (1) were suspended in a medium for inducing differentiation containing neither blood serum nor LIF and then seeded on PA6 cells in a slide chamber (Nunc). The induced differentiation medium was prepared by adding, to G-MEM (Invitrogen) containing 10% knockout serum replacement (Invitrogen), 2 mM L-glutaminic acid (Invitrogen), 0.2 mM 2-mercaptoethanol (Sigma), 1 mM sodium pyruvate (Invitrogen), and 0.1 mM MEM nonessential amino acid. After the cells were cultured for 10 days, they were fixed with 4% paraformaldehyde, immunostained with an antibody (TUJI, Berkeley Antibody Company) against β tubulin that expressed specifically in the nerve cells, and subjected to observation by a confocus fluorescent microscope. The cells extended neuritis presenting the morphology of nerve cells. It was therefore confirmed that the cells stained with an anti-β-tubulin antibody expressed GFP. Representative images observed by a confocus fluorescent microscope are shown in FIGS. 22a and 22b.

From the experiments (1) and (2), it was confirmed that the ES cells retaining a HAC vector derived from human chromosome 21 transferred therein keep a differentiation potency into the nerve cells.

INDUSTRIAL APPLICABILITY

A human artificial chromosome (HAC) vector is provided by the present invention. Since the HAC vector is reduced in size and an unnecessary gene is deleted therefrom, it can be present stably in a cell. The HAC vector of the present invention is prepared based on a human chromosome. Therefore, a large foreign DNA can be inserted by the HAC vector. Furthermore, the HAC vector of the present invention has a recognition site for a site-specific recombinant enzyme. Therefore, a foreign DNA can be inserted simply as a cassette. Since the site where a foreign DNA is introduced can be appropriately designed, the HAC vector is free from positional effect. By use of the HAC vector of the present invention, a large foreign DNA can be introduced into a cell and expressed therein. Therefore, the HAC vector of the present invention can be used in producing a desired protein by highly expressing a gene encoding the protein, in-vivo functional analysis of a gene or protein unknown in action and cloning of a large DNA. Hence, the HAC vector is useful in the fields relevant to gene engineering.

Free Text for Sequencing Listing
SEQ. ID Nos. 1 to 62: Synthetic oligonucleotides

The invention claimed is:

1. A human artificial chromosome vector comprising a fragment of human chromosome 21, wherein said human artificial chromosome vector possesses a whole long arm region from the centromere to AL163204, exists as a monomer and is stably transmitted as a single copy, wherein the fragment of chromosome 21 is about 2-16 Mb, wherein:
   i) a distal region of the long arm of human chromosome 21 is deleted within the AL163204 region; or
   ii) a distal region of the long arm of human chromosome 21 is deleted within the AL163204 region and a distal region of the short arm of human chromosome 21 is deleted at AL163201,
   and wherein an expression cassette comprising a recognition site for a site-specific recombination enzyme is inserted into a proximal region of the long arm and/or a proximal region of the short arm of human chromosome 21.

2. The human artificial chromosome vector according to claim 1, wherein the site-specific recombination enzyme is Cre enzyme.

3. The human artificial chromosome vector according to claim 1 or 2, wherein the recognition site for the site-specific recombination enzyme is the loxP sequence.

4. The human artificial chromosome vector according to claim 1, wherein the recognition site for the site-specific recombination enzyme is inserted into AL163203 in the proximal region of the long arm of human chromosome 21.

5. The human artificial chromosome vector according to claim 1, wherein the deletion of the distal region of the long arm and/or the distal region of the short arm is by substitution with an artificial telomere sequence.

* * * * *